United States Patent
Nauerth et al.

(10) Patent No.: US 11,320,431 B2
(45) Date of Patent: May 3, 2022

(54) COMBINATION OF REVERSIBLE AND IRREVERSIBLE CELL LABELING FOR ANALIZING RECEPTOR-LIGAND $K_{off}$ RATE

(71) Applicants: TECHNISCHE UNIVERSITAET MUENCHEN, Munich (DE); JUNO THERAPEUTICS GMBH, Munich (DE)

(72) Inventors: Magdalena Nauerth, Munich (DE); Dirk Busch, Schliersee (DE); Lothar Germeroth, Goettingen (DE)

(73) Assignees: TECHNISCHE UNIVERSITAET MUENCHEN, Munich (DE); JUNO THERAPEUTICS GMBH, Munich (DE)

( * ) Notice: Subject to any disclaimer, the term of this patent is extended or adjusted under 35 U.S.C. 154(b) by 251 days.

(21) Appl. No.: 16/314,126

(22) PCT Filed: Jun. 27, 2017

(86) PCT No.: PCT/EP2017/065755
§ 371 (c)(1),
(2) Date: Dec. 28, 2018

(87) PCT Pub. No.: WO2018/001985
PCT Pub. Date: Jan. 4, 2018

(65) Prior Publication Data
US 2019/0227061 A1 Jul. 25, 2019

(30) Foreign Application Priority Data

Jun. 28, 2016 (EP) .................................... 16176537

(51) Int. Cl.
*G01N 33/557* (2006.01)
*G01N 33/566* (2006.01)
(Continued)

(52) U.S. Cl.
CPC ..... *G01N 33/557* (2013.01); *C07K 14/70539* (2013.01); *C12N 5/0636* (2013.01);
(Continued)

(58) Field of Classification Search
CPC .......... C07K 14/70539; C07K 2319/22; C12N 5/0636; G01N 33/566
See application file for complete search history.

(56) References Cited

U.S. PATENT DOCUMENTS

| 4,851,341 A | 7/1989 | Hopp et al. |
| 5,506,121 A | 4/1996 | Skerra et al. |

(Continued)

FOREIGN PATENT DOCUMENTS

| EP | 0700430 B1 | 4/2005 |
| JP | 2004525354 A | 8/2004 |

(Continued)

OTHER PUBLICATIONS

Laugel J. Biological Chem. 2007 Vo. 282, p. 23799-23810 (Year: 2007).*

(Continued)

*Primary Examiner* — Changhwa J Cheu
(74) *Attorney, Agent, or Firm* — Acuity Law Group, PC; Michael A. Whittaker

(57) ABSTRACT

The invention relates to a method of determining the dissociation rate constant ($k_{off}$) of a receptor molecule R on a target cell using a combination of reversible and irreversible cell labeling. The invention further relates to a cell comprising such a receptor molecule R, wherein the cell has bound to it such a combination of cell labeling. The invention further relates to a kit and an apparatus useful in performing the methods of the invention. The invention further relates to a method of isolation a high-avidity T cell.

19 Claims, 29 Drawing Sheets

Specification includes a Sequence Listing.

(51) Int. Cl.
- *G01N 33/543* (2006.01)
- *G01N 33/50* (2006.01)
- *C07K 14/74* (2006.01)
- *C12Q 1/04* (2006.01)
- *C12N 5/0783* (2010.01)

(52) U.S. Cl.
CPC ............ *C12Q 1/04* (2013.01); *G01N 33/502* (2013.01); *G01N 33/543* (2013.01); *G01N 33/566* (2013.01); *C07K 2319/22* (2013.01); *G01N 2458/00* (2013.01)

(56) References Cited

U.S. PATENT DOCUMENTS

| | | |
|---|---|---|
| 5,985,658 A | 11/1999 | Colinas et al. |
| 6,103,493 A | 8/2000 | Skerra et al. |
| 6,352,694 B1 | 3/2002 | June et al. |
| 7,776,562 B2 | 8/2010 | Busch et al. |
| 7,981,632 B2 | 7/2011 | Schmidt |
| 8,298,782 B2 | 10/2012 | Busch et al. |
| 2011/0070605 A1 | 3/2011 | Busch et al. |

FOREIGN PATENT DOCUMENTS

| | | |
|---|---|---|
| JP | 2005500257 A | 1/2005 |
| JP | 2009522546 A | 6/2009 |
| JP | 2014511494 A | 5/2014 |
| JP | 2014529361 A | 11/2014 |
| WO | 02054065 A2 | 7/2002 |
| WO | 02072631 A2 | 9/2002 |
| WO | 02077018 A1 | 10/2002 |
| WO | 2007084232 A1 | 7/2007 |
| WO | 2012120506 A2 | 9/2012 |
| WO | 2013/011011 A2 | 1/2013 |

OTHER PUBLICATIONS

Holm et al. Biochimica & Biophysica Acta 2014 vol. 1844, p. 512-519 (Year: 2014).*

International Search Report and Written Opinion issued in PCT/EP2017/065755 dated Oct. 6, 2017 (18 pages).

Hebeisen et al., "Identification of Rare High-Avidity, Tumor-Reactive cos+ T Cells by Monomeric TCR-Ligand Off-Rates Measurements on Living Cells", Cancer Research, vol. 75, No. 10, May 15, 2015 (May 15, 2015), pp. 1983-1991.

Nauerth et al., "CR-ligand koff rate correlates with the protective capacity of antigen-specific CD8+ T cells for adoptive transfer", Science Translational Medicine, AAAS—American Association for the Advancement of Science, US, vol. 5, No. 192, Jul. 3, 2013 (Jul. 3, 2013), pp. 70-79.

Nauerth et al., "Supplementary Materials for TCR-Ligand koff RateCorrelates with the Protective Capacity of Antigen-Specific CD8+ T Cells for Adoptive Transfer", Science Translational Medicine,vol. 5, No. 192, Jul. 3, 2013 (Jul. 3, 2013), pp. 192ra87-192ra87.

Hombrink et al., "Mixed functional characteristics correlating with TCR-ligand k off -rate of MHC-tetramer reactive T cells within the naive T-cell repertoire", European Journal of Immunology, vo 1 • 43. No. 11, Nov. 25, 2013 (Nov. 25, 2013), pp. 3038-3050.

Weissbrich et al., "Adoptive Immunotherapy", Oncoimmunology, Vo.. 2, No. 10, Oct. 1, 2013, p. E26199.

Nauerth, Magdalena "Development of a novel TCR avidity assay for human CD8+ T cells", May 6, 2012 (May 6, 2012), XP055308572, Retrieved from the Internet: URL:http://mediatum.ub.tum.de/doc/1097838/ 1097838.pdf p. 42-p. 87.

Knabel et al., Reversible MHC multimer staining for functional isolation of T-cell populations and effective adoptive transfer11, Nature Medicine, Nature Publishing Group, New York, NY, US, vol. 8, No. 6, Jun. 1, 2002 (Jun. 1, 2002), pp. 631-637.

Schroeder, Tim "Mach Zellen angeln", Faszination Forschung : Das Wissenschaftsmagazin, Monchen Tum, DE, Jun. 30, 2010 (Jun. 30, 2010), pp. 28-37.

Stemberger et al., "Novel Serial Positive Enrichment Technology Enables Clinical Multiparameter Cell Sorting", PLOS ONE, vol. 7, No. 4, Apr. 24, 2012 (Apr. 24, 2012), p. e35798.

Busch et al., Coordinate Regulation of Complex T Cell Populations Responding to Bacterial Infection. Immunity. Mar. 1998;8(3):353-362.

Hadrup et al., Parallel detection of antigen-specific T-cell responses by multidimensional encoding of MHC multimers. Nat Methods. Jul. 2009;6(7):520-526.

Huang et al., Facile Synthesis of Multivalent Nitrilotriacetic Acid (NTA) and NTA Conjugates for Analytical and Drug Delivery Applications. Bioconjug Chem. Nov.-Dec. 2006;17(6):1592-1600.

Ill et al. Design and construction of a hybrid immunoglobulin domain with properties of both heavy and light chain variable regions. Protein Eng. Aug. 1997;10(8):949-957.

Lata et al., High-Affinity Adaptors for Switchable Recognition of Histidine-Tagged Proteins. J Am Chem Soc. Jul. 27, 2005;127(29):10205-10215.

Martin et al. The affinity-selection of a minibody polypeptide inhibitor of human interleukin-6. EMBO J. Nov. 15, 1994;13(22):5303-5309.

Nauerth et al., TCR-Ligand koff Rate Correlates with the Protective Capacity of Antigen-Specific CD8+ T Cells for Adoptive Transfer. Sci Transl Med. Jul. 3, 2013;5(192):192ra87.

Noguchi et al., Preparation and Properties of the Immunoconjugate Composed of Anti-Human Colon Cancer Monoclonal Antibody and Mitomycin C-dextran Conjugate. Bioconjug Chem. Mar.-Apr. 1992;3(2):132-137.

Silverman et al., Multivalent avimer proteins evolved by exon shuffling of a family of human receptor domains. Nat Biotechnol. Dec. 2005;23(12):1556-61.

Traunecker et al, Janusin: new molecular design for bispecific reagents. Int J Cancer Suppl. 1992;7:51-52.

Traunecker et al., Bispecific single chain molecules (Janusins) target cytotoxic lymphocytes on HIV infected cells. EMBO J. Dec. 1991;10(12):3655-3659.

Office Action issued by the JPO in Japanese Patent Application No. 2018-569087 dated Jul. 5, 2021—incl Engl lang transl (14 pages total).

* cited by examiner

A

B

D)

E)

A)

MHC

Streptactin

Clone 1A7
B8 IE1K$_{199-207}$

B)

Clone 5A6
B8 IE1$_{88-96}$

C)

Clone 4H4
B8 IE1$_{88-96}$

D)

A)

B)

A)

B)

C)

D)

E)

F)

A)

B)

sorted cells (reversible multimer only)

C)

double staining with reversible and non-reversible multimer

D)

a.

b.

c.

a. (cont'd)

b. (cont'd)

c. (cont'd)

US 11,320,431 B2

COMBINATION OF REVERSIBLE AND IRREVERSIBLE CELL LABELING FOR ANALIZING RECEPTOR-LIGAND $K_{off}$ RATE

CROSS-REFERENCE TO RELATED APPLICATIONS

The present invention is filed under 35 U.S.C. § 371 as the U.S. national phase of International Application No. PCT/EP2017/065755, filed Jun. 27, 2017, which designated the U.S. and claims the right of priority of European patent application No. 16176537.5, filed with the European Patent Office on Jun. 28, 2016. The entire disclosures of the above-identified priority applications are hereby fully incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 28, 2018, is named SCH-4900-US_SeqListing.txt and is 4 kilobytes in size.

FIELD OF THE INVENTION

The invention relates to a method of determining the dissociation rate constant ($k_{off}$) of a receptor molecule R on a target cell using a combination of reversible and irreversible cell labeling. The invention further relates to a cell comprising such a receptor molecule R, wherein the cell has bound to it such a combination of cell labeling. The invention further relates to a kit and an apparatus useful in performing the methods of the invention. The invention further relates to a method of isolation a high-avidity T cell.

BACKGROUND

The importance of cellular adaptive immunity in the control of viral and some bacterial infections has been convincingly demonstrated by depletion or adoptive transfer experiments, as well as in genetic mouse models. Thereby, antigen-specific CD8+ T cells seem to play a dominant role for protection against intracellular pathogens. Also in certain cancers, the presence of functional CD8+ T cells could be associated with the induction of tumor regression. Different immunotherapeutic approaches therefore aim at the reconstitution of a functional CD8+ T cell response in patients. If antigen-specific T cells are still present but silenced by the micromilieu, application of 'checkpoint inhibitors' can serve to re-activate the efficacy of existing T cells. However, if endogenous antigen-specific T cells are lacking or existing cells carry T cell receptors (TCRs) with weak antigen recognition, adoptive T cell transfer of more potent T cells might represent a promising approach to restore a protective antigen specific CD8+ T cell response. Research over the last decades has indicated that not only the quantity but also the quality of prevalent or adoptively transferred T cells correlates with the success of T cell based immunotherapies. Thus, it is of high interest in the field to characterize the functional capacity of defined antigen-specific T cell populations for both diagnostic as well as therapeutic applications.

An important parameter to describe T cell functionality is referred to as 'T cell avidity', which is commonly assessed on the functional level, e.g. as cytokine production after antigen-specific stimulation. T cells with high functional avidity could be shown to be superior in clearing viral infections or inducing tumor regression. A major part of T cell avidity is hard-wired within the TCR and can be assessed as structural avidity, which is the binding strength of the TCR to its cognate ligand, the peptide major histocompatibility complex (pMHC).

Nauerth et al., 2013, Science Translational Medicine, 5(192):192ra87, reported on the so-called 'TCR-ligand $k_{off}$-rate assay', to quantify an important component of structural TCR avidity. This assay is based on reversible multimers, so called Streptamers. Recombinantly expressed pMHCs can be multimerized on a Streptactin backbone over a short Streptag sequence, which is fused to the C-term of the pMHCs. These multimeric complexes can stably bind to TCRs expressed on the surface of living T cells. With the addition of biotin, however, the multimeric complex is disrupted, leaving monomeric TCR-pMHC complexes on the T cell surface. This monomeric binding is not stable and the pMHCs dissociate from the TCRs with kinetics depending on the TCR-pMHC binding strength. If the pMHCs are fluorescently labelled, their dissociation can be monitored by the decay of the fluorescent dye. In contrast to other methods assessing structural avidity, the TCR-ligand $k_{off}$-rate assay enables measurement of the dissociation of truly monomeric pMHCs bound to TCRs expressed on the surface of living T cells. Using the $k_{off}$-rate assay with the help of fluorescence microscopy, the inventors could demonstrate a clear correlation between the TCR-pMHC binding half-life time ($t_{1/2}$) and the functionality of corresponding T cells. T cells with a slow $t_{1/2}$ showed not only higher functional avidity in vitro, but also a higher protective capacity against infection in vivo.

Monitoring the fluorescence decay by real-time microscopy offers the possibility to accurately analyze the TCR-ligand $k_{off}$-rates on the single cell level. Unfortunately, the assay setup is quite labour intensive and requires specific instrumentation. Hebeisen et al. 2015, Cancer Res, 75(10): 1983-91 proposed to combine $k_{off}$-rate measurements with previous sorting or cloning of analyzed T cells. However, this is not only a time consuming procedure, it also bears the risk to bias obtained results as in vitro expansions protocols often change the composition of complex T cell populations.

It is thus object of the invention to provide means and methods that at least partially overcomes these drawbacks

SUMMARY OF THE INVENTION

The present invention relates to a method of determining the dissociation rate constant ($k_{off}$) of a receptor molecule R on a target cell and a first receptor binding site B1, comprising detecting a first detectable label attached to the target cell and a second detectable label attached to the target cell, wherein the cell has been contacted with (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; and wherein said first detectable label is bound or capable of binding to said first receptor binding reagent; and wherein said second detectable label is essentially irreversibly attached to said receptor molecule R, wherein the first detectable label and the second detectable label are different from each other.

The invention further encompasses that the cell may have further been contacted with (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; and wherein said second detectable label is bound to said second multivalent binding complex.

The invention also encompasses that the cell may have further been contacted with (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein said second detectable label is bound to said multimeric receptor binding reagent M2.

The invention also encompasses that the cell may have further been contacted with (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2.

The invention further encompasses a cell comprising at least three receptor molecules R, wherein the cell has bound to at least two receptor molecules R (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; and wherein a first detectable label is bound to said first receptor binding reagent; and wherein a second detectable label is essentially irreversibly attached to at least one receptor molecule R.

The invention further encompasses that the cell may have further bound to at least two receptor molecules R (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; and wherein said second detectable label is bound to said second multivalent binding complex.

The invention also encompasses that the cell may have further bound to at least two receptor molecules R (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said cell via said at least two receptor molecules R, wherein said second detectable label is bound to said multimeric receptor binding reagent M2.

The invention also encompasses that the cell may have further bound to a receptor molecule R (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2

The invention further encompasses a reagent kit for determining the dissociation rate constant ($k_{off}$) of a receptor molecule R on a target cell and a first receptor binding site B1, wherein the kit comprises (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; wherein said first detectable label is bound or capable of binding to said first receptor binding reagent.

The kit further comprises (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; wherein a second detectable label is bound to said second multivalent binding complex; or (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein a second detectable label is bound to said multimeric receptor binding reagent M2; or (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein a second detectable label is bound to said irreversible receptor binding reagent I2; and wherein the first detectable label is not the second detectable label.

The present invention further encompasses an apparatus comprising a first container containing a target cell comprising a receptor molecule R, and (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) are capable of forming a first multivalent binding complex that binds to said target cell, the first multivalent binding complex comprising at least two of said first receptor binding reagents bound to one said first multimerization reagent; and wherein said first detectable label is bound or capable of binding to said first receptor binding reagent; and wherein said second detectable label is essentially irreversibly attached to said receptor molecule R wherein the first detectable label is not the second detectable label; and a second container containing a fluid comprising (a) a competition reagent CR, wherein the competition reagent CR is capable of competing with first binding partner C1 for the binding to the first binding site Z1 on the first multimerization reagent; or (b) a metal chelating reagent, wherein the metal chelating reagent is preferably EDTA or EGTA, wherein the first container and a second container are connected such that a fluid can be transferred from the second container to the first container.

The first container of the apparatus may further contain (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stably binding of the second binding partner C2 of the second receptor binding reagent, wherein the second receptor binding reagent (iii) and the second multimerization reagent (iv) are capable of forming a second multivalent binding complex that binds to said target cell, the second multivalent binding complex comprising at least two of second receptor binding reagents bound to one said second multimerization reagent; and wherein said second detectable label is bound to said second multivalent binding complex.

The first container of the apparatus may further contain (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein said second detectable label is bound to said multimeric receptor binding reagent M2.

The first container of the apparatus may further contain (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2.

The invention further encompasses a method of isolating a high-avidity T cell comprising (a) determining the dissociation rate constant ($k_{off}$) of a T cell in a sample obtained from a subject using a method of the invention described herein and (b) isolating said T cell from a sample obtained from said subject.

BRIEF DESCRIPTION OF THE DRAWINGS

FIG. 1A shows a schematic depiction of a first multimerization reagent (25) comprising at least two first binding sites Z1 (26) and optionally a third detectable label (93); a second multimerization reagent (35) comprising at least two second binding sites Z2 (36) and a second detectable label; a first receptor binding reagent (20) comprising a first receptor binding site B1 (71), a first detectable label (91), and a first binding partner C1 (81); a second receptor binding reagent (30) comprising a second receptor binding site B2 (72) and a second binding partner C2 (82); a multimeric receptor binding reagent M2 (40) comprising at least two second receptor binding sites B2 (72) and a second detectable label (92); an irreversible receptor binding reagent I2 (50) comprising an irreversible receptor binding site B3 (73) and a second detectable label (92); and a target cell (10) comprising at least one receptor molecule R (11).

FIG. 1B illustrates the principle of dissociation rate constant ($k_{off}$) determination using a first multimerization reagent (25) and a second multimerization reagent (35). The target cell (10) has bound to at least two receptor molecules R (11) the first receptor binding site B1 (71) of a first receptor binding reagent (20). The first receptor binding reagent (20) comprises a first receptor binding site B1 (71), a first detectable label (91) and a first binding partner C1 (81). At least two first receptor binding reagents (20) are reversibly bound to a first multimerization reagent (25) via the first binding partner C1 (81) comprised in the first receptor binding reagents (20) and the first binding site Z1 (26) comprised in the first multimerization reagent (25). The first multimerization reagent (25) optionally comprises a third detectable label (93). Furthermore, the target cell (10) has bound to at least two receptor molecules R (11) the second receptor binding site B2 (72) of a second receptor binding reagent (30). At least two second receptor binding reagents (30) are stably bound to a second multimerization reagent (35) via the second binding partner C1 (82) comprised in the second receptor binding reagents (30) and the second binding site Z2 (36) comprised in the second multimerization reagent (35). The second multimerization reagent (35) comprises a second detectable label (92). Alternatively, the second detectable label can be comprised in the second receptor binding agent (30) in addition to or instead of being comprised in the second multimerization reagent (not shown in the Figure). Upon contacting the complex with a competition reagent CR (60), the competition reagent CR (60) competes with the first binding partner C1 (81) comprised in the first receptor binding reagent (20) for the first binding site Z1 (26) comprised in the first multimerization reagent (25). Due to binding of the competition reagent CR (60) to the first binding site Z1 (26) comprised in the first multimerization reagent (25), the binding between the first receptor binding reagent (20) and the first multimerization reagent (25) is disrupted and the first multimerization reagent (25), and eventually the first receptor binding reagent (20), detach from the target cell (10).

FIG. 1C shows the principle of dissociation rate constant ($k_{off}$) determination using a first multimerization reagent (25) and a multimeric receptor binding reagent M2 (40). The target cell (10) has bound to at least two receptor molecules R (11) the first receptor binding site B1 (71) of a first receptor binding reagent (20). The first receptor binding reagent (20) comprises a first receptor binding site B1 (71), a first detectable label (91) and a first binding partner C1 (81). At least two first receptor binding reagents (20) are reversibly bound to a first multimerization reagent (25) via the first binding partner C1 (81) comprised in the first receptor binding reagents (20) and the first binding site Z1 (26) comprised in the first multimerization reagent (25). The first multimerization reagent (25) optionally comprises a third detectable label (93). Furthermore, the target cell (10) has bound to at least two receptor molecules R (11) the second receptor binding site B2 (72) of a multimeric receptor binding reagent M2 (40). The multimeric receptor binding reagent M2 (40) comprises a second detectable label (92). Upon contacting the complex with a competition reagent CR (60), the competition reagent CR (60) competes with the first binding partner C1 (81) comprised in the first receptor binding reagent (20) for the first binding site Z1 (26) comprised in the first multimerization reagent (25). Due to binding of the competition reagent CR (60) to the first binding site Z1 (26) comprised in the first multimerization reagent (25), the binding between the first receptor binding reagent (20) and the first multimerization reagent (25) is disrupted and the first multimerization reagent (25), and eventually the first receptor binding reagent (20), detach from the target cell (10).

FIG. 1D shows the principle of dissociation rate constant ($k_{off}$) determination using a first multimerization reagent (25) and an irreversible receptor binding reagent I2 (50). The target cell (10) has bound to at least two receptor molecules R (11) the first receptor binding site B1 (71) of a first receptor binding reagent (20). The first receptor binding reagent (20) comprises a first receptor binding site B1 (71), a first detectable label (91) and a first binding partner C1 (81). At least two first receptor binding reagents (20) are reversibly bound to a first multimerization reagent (25) via the first binding partner C1 (81) comprised in the first receptor binding reagents (20) and the first binding site Z1 (26) comprised in the first multimerization reagent (25). The first multimerization reagent (25) optionally comprises a third detectable label (93). Furthermore, the target cell (10) has bound to a receptor molecule R (11) the irreversible receptor binding reagent I2 (50). The irreversible receptor binding reagent I2 (50) comprises a second detectable label (92). Upon contacting the complex with a competition reagent CR (60), the competition reagent CR (60) competes with the first binding partner C1 (81) comprised in the first receptor binding reagent (20) for the first binding site Z1 (26) comprised in the first multimerization reagent (25). Due to binding of the competition reagent CR (60) to the first binding site Z1 (26) comprised in the first multimerization reagent (25), the binding between the first receptor binding reagent (20) and the first multimerization reagent (25) is disrupted and the first multimerization reagent (25), and eventually the first receptor binding reagent (20), detach from the target cell (10).

FIG. 2A is a schematic depiction of an exemplary setup on a flow cytometer. FIG. 2B is an exemplary depiction of a sample temperature controller with FACS tube for the $k_{off}$-rate assay. FIG. 2C shows an exemplary gating strategy of the flow based $k_{off}$-rate assay with T cell clones: T cell clones expressing the 2C TCR were stained with reversible multimers (comprising Streptactin APC and SIYRYYGL(SEQ ID NO: 10)-H2Kb-Alexa488) and Propidium Iodide (PI) for live/dead discrimination. Stained cell were analyzed on a Cyan Lx, 2 mM D-biotin was added after 30 s and dissociation was observed for 10 min. Samples were gated on living lymphocytes and dissociation of Streptactin-APC and MHC-Alexa488 from these cells were observed. FIG. 2D shows a reduction of data to visualize dissociation kinetics: APC and Alexa488 Fluorescence intensity of living lymphocytes was plotted over the computed time of analysis in FlowJo. The computed time was divided in 200 gates, and mean fluorescence intensity (MFI) of all cells contained in one gate was calculated. MFI values of APC (left axis) and Alexa488 (right axis) were plotted over time of analysis in Graph Pad Prism (top graph). Data points for analysis were selected and fitted with an exponential decay (bottom graph). FIG. 2E is a direct analysis of dissociation kinetics of all cells: Fluorescence values of all living lymphocytes are directly exported to Graph Pad Prism. Data points for analysis are selected and are fitted with an exponential decay.

FIG. 3A to FIG. 3C show $k_{off}$-rate assays of human CMV-specific T cell clones: T cell clones were stained with specific reversible multimers (comprising Streptactin APC and MHC-Alexa488) and Propidium Iodide (PI) for live/dead discrimination. $K_{off}$-rate assay was performed on a Cyan Lx. Fluorescence values of Alexa 488 and APC staining of living cells are plotted over the time of analysis, data points for analysis are selected as described and fitted with an exponential decay. FIG. 3D shows a comparison of the TCR-pMHC binding half-life times assessed on the microscope and on the flow cytometer.

FIG. 4A is a schematic representation of the staining of a CD8+ T cell with a reversible and a non-reversible multimer (top left) and the dissociation of the reversible multimer after the addition of D-biotin (bottom right). FIG. 4B shows that T cells derived from Human CMV-specific T cell clones were stained with specific reversible multimer (comprising Streptactin APC and HLA-B8 IE188-96-Alexa488), Propidium Iodide (PI) for live/dead discrimination and with the specific, non-reversible multimer (comprising Streptavidin BV421 and unlabeled B8 IE188-96 molecules). Dot plot of the double staining (Streptactin APC and Streptavidin BV421, gated on living, CD8+ lymphocytes) of a human CMV-specific T cell clone before addition of D-biotin (left). Staining intensities of the backbone of the non-reversible multimer (Streptavidin BV421) and of the backbone (Streptactin APC) and the pMHC molecules (Alexa488) of the reversible multimer over time of analysis with addition of D-biotin after 30 s.

FIG. 5A depicts titration of incubation time and concentration of the non-reversible multimer staining: PBMCs from a CMV positive (B7 pp65) donor were incubated with the specific reversible multimer (comprising Streptactin APC and HLA-B7 pp65-Alexa488), antibodies against CD8 PE-Cy and Propidium Iodide (PI) for live/dead discrimination. After washing, samples were incubated with the specific non-reversible multimer, with incubation time and dilution of the multimer indicated above the dot plots (see also Material and Methods). Dot plots show CD8 Pe-Cy7 and Streptavidin BV421 staining of CD8+ living lymphocytes. FIG. 5B and FIG. 5C show histograms of the staining of the non-reversible multimer (Streptavidin BV421) and the reversible multimer (MHC Alexa 488 and Streptactin APC) of the gates depicted in FIG. 5A). FIG. 5D shows TCR-pMHC $k_{off}$-rates of B7pp65 specific T cells contained in the samples described in A). FIG. 5E and FIG. 5F shows the results of two CMV-specific T cell clones (specific for HLA B8 IE188-96) that were either stained with the reversible multimer alone or in combination with the non-reversible multimer conjugated with BV421 or with PE. All samples were stained with Propidium Iodide (PI) for live/dead discrimination. $K_{off}$-rates were measured from living lymphocytes.

PBMCs from a CMV positive donor (specific for HLA B7 pp65) were stained with the specific reversible multimer (comprising Streptactin APC and MHC-Alexa488), antibodies against CD8 and Propidium Iodide (PI) for live/dead discrimination. Cells were split in two samples. FACS sorting for living CD8+ Streptactin APC+ lymphocytes was performed on a MoFlo (Beckman Coulter) with one sample. The other sample was additionally stained with the non-reversible multimer (comprising Streptavidin PE). FIG. 6A shows dot plots of the Streptavidin PE and the CD8 eF450 staining of living lymphocytes (left picture) and the MHC Alexa488 and Streptactin staining of Streptavidin+ cells of the double stained sample (right picture). FIG. 6B shows $k_{off}$-rate assays with reversible multimer stained B7pp65 specific T cells while FIG. 6C shows $k_{off}$-rate assays with double stained B7pp65 specific T cells. Fluorescence values of Alexa 488 and APC staining of the analyzed cells are plotted over the time of analysis, data points for analysis are selected as described and fitted with an exponential decay. FIG. 6D shows a comparison of the TCR-pMHC binding half-life times of the sorted and the double stained sample.

PBMCs were isolated by Ficoll gradient centrifugation from fresh blood of a healthy donor. Boolean gating on single living CD19-CD8+ non-reversible pMHC-PE+ T cells. Data of Streptactin APC and reversible pMHC-Alexa488 over time were exported to GraphPad PRISM to fit an exponential decay curve to determine the $k_{off}$ rate.

Figure 8:
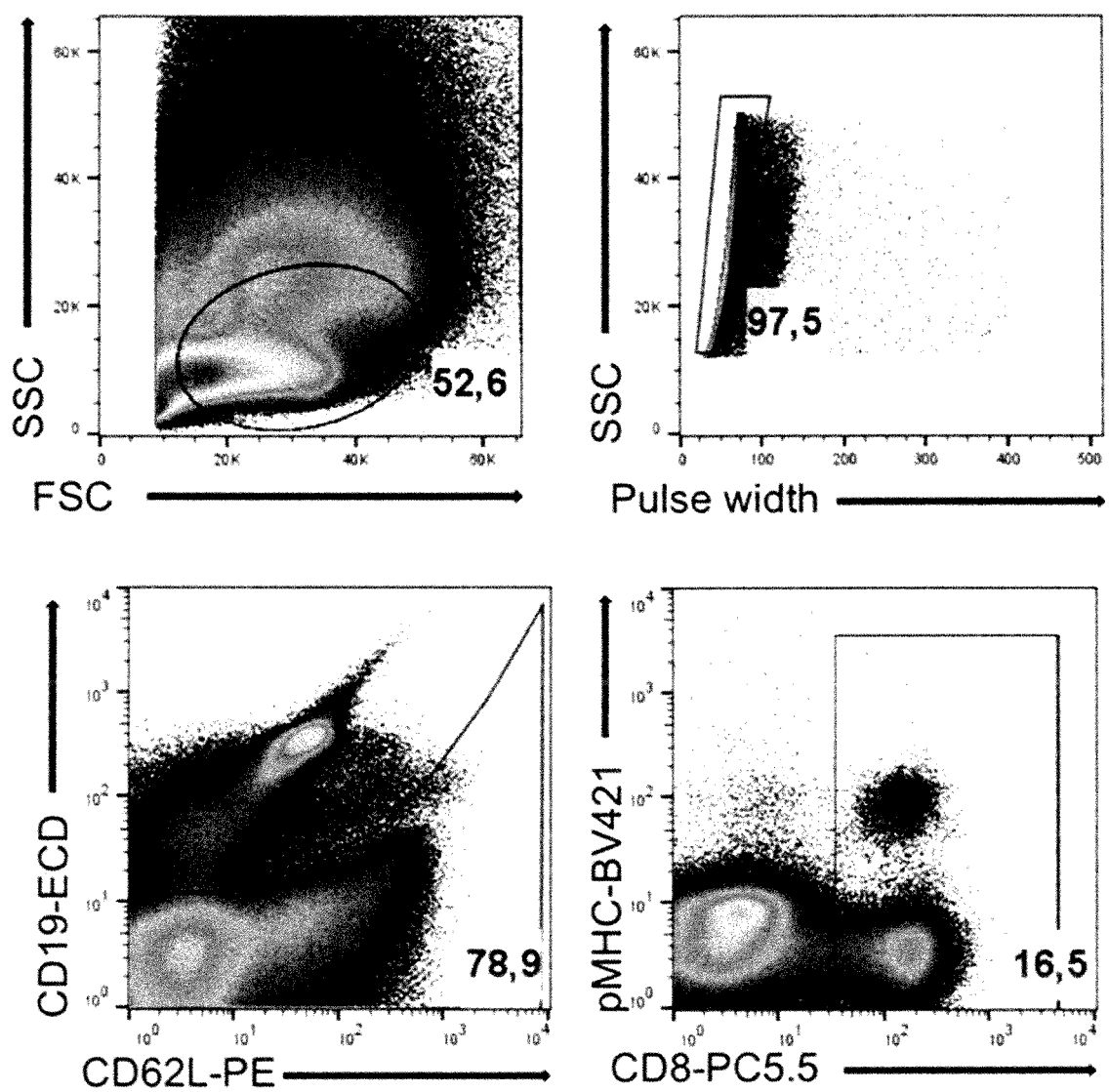
Figure 8:
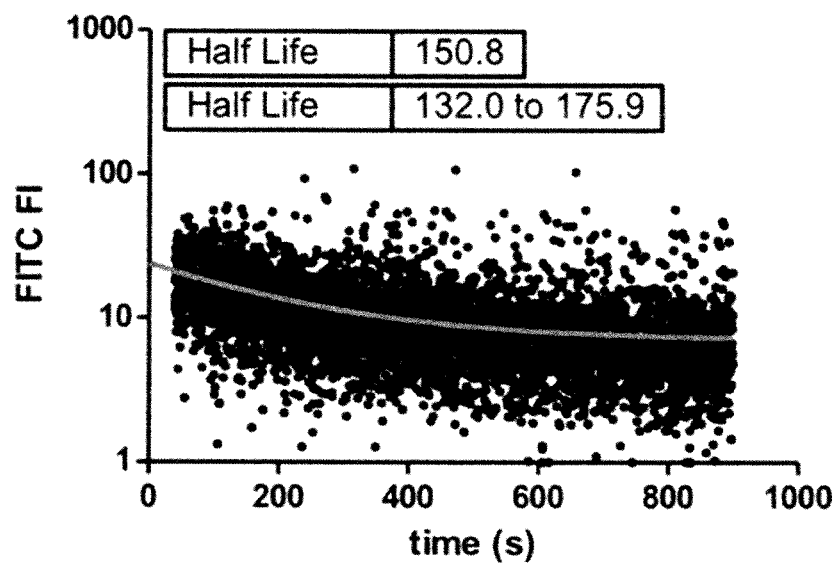

FIG. 8: Ex Vivo $k_{off}$ Rate Measurement of an Oligo Clonal HLA*02 01/CMVpp65 Specific CD8 T Cell Population (Donor HZ961).

$k_{off}$ rate measurement of cryopreserved PBMCs isolated by Ficoll gradient centrifugation from fresh blood of a healthy donor. Boolean gating on single living CD19-CD8+ non-reversible pMHC-PE+ T cells. Data of Streptactin APC and reversible pMHC-Alexa488 over time were exported to GraphPad PRISM to fit an exponential decay curve to determine the $k_{off}$ rate.

Figure 9:
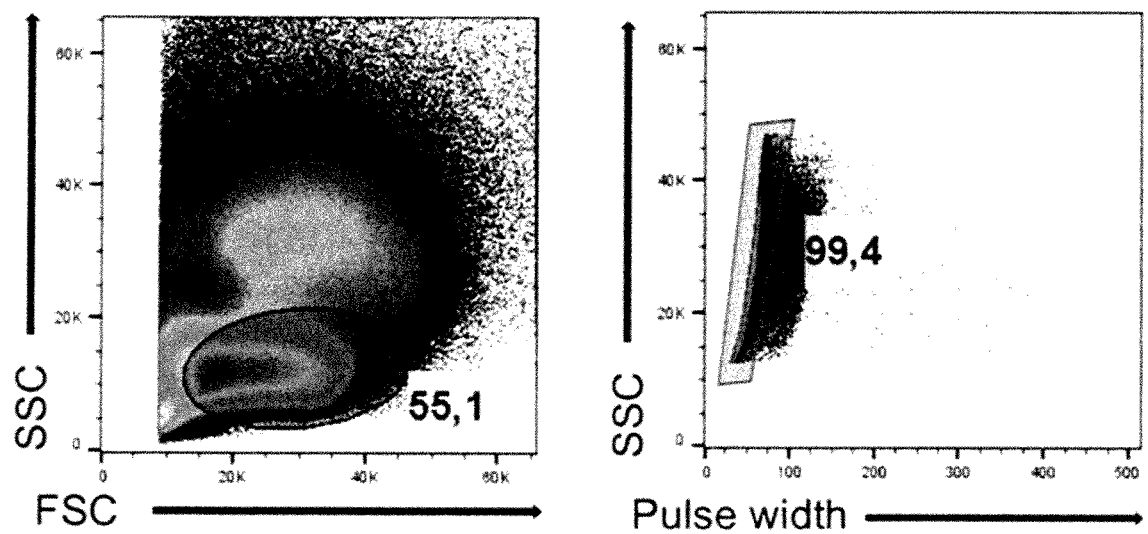
Figure 9:
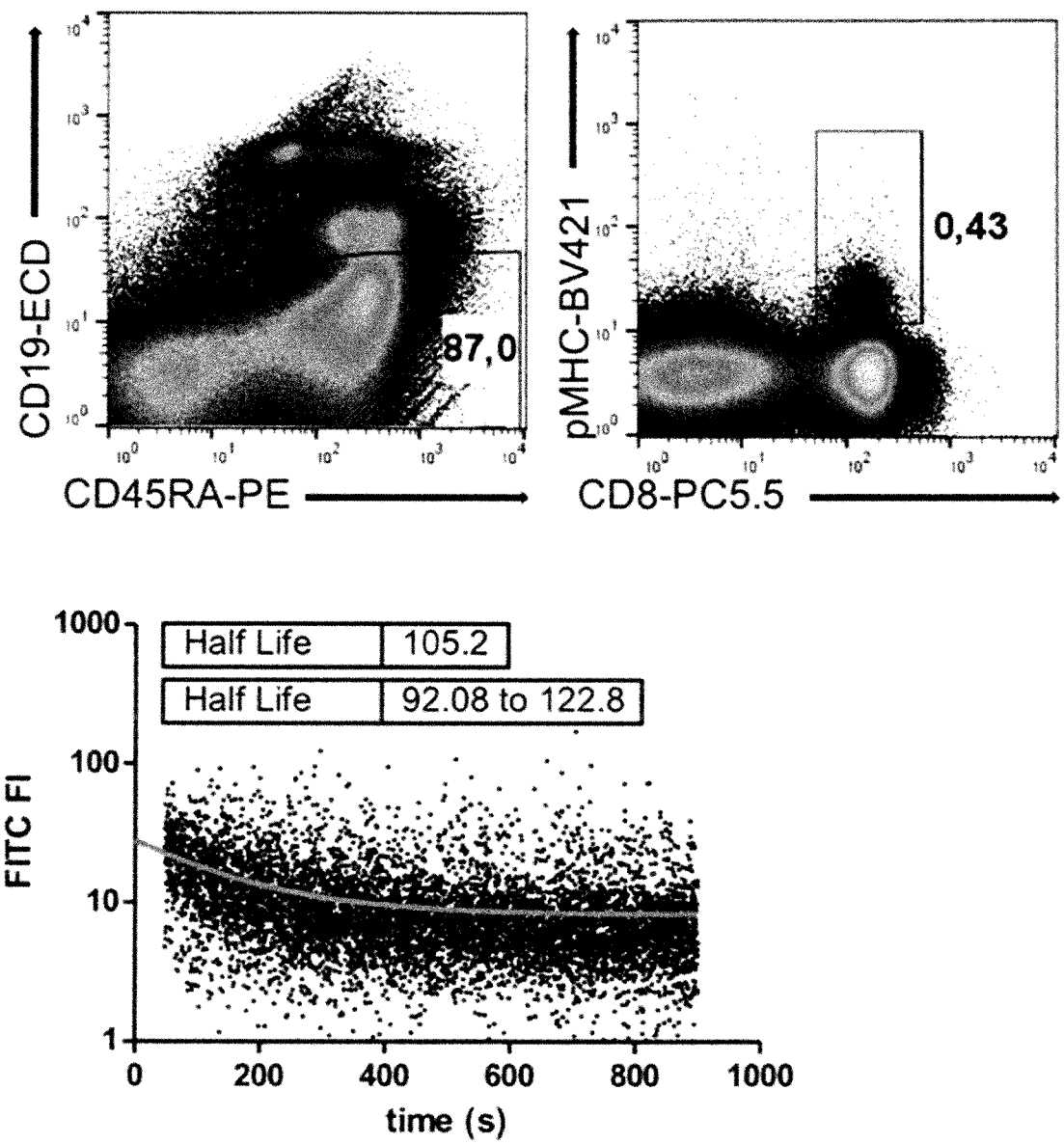

FIG. 9: Ex Vivo $k_{off}$ Rate Measurement of an Oligo Clonal HLA*02 01/CMVpp65 Specific CD8 T Cell Population (Donor HZ510).

$k_{off}$ rate measurement of cryopreserved PBMCs isolated by Ficoll gradient centrifugation from fresh blood of a healthy donor. Boolean gating on single living CD19-CD8+ non-reversible pMHC-PE+ T cells. Data of Streptactin APC and reversible pMHC-Alexa488 over time were exported to GraphPad PRISM to fit an exponential decay curve to determine the $k_{off}$ rate.

Figure 10:
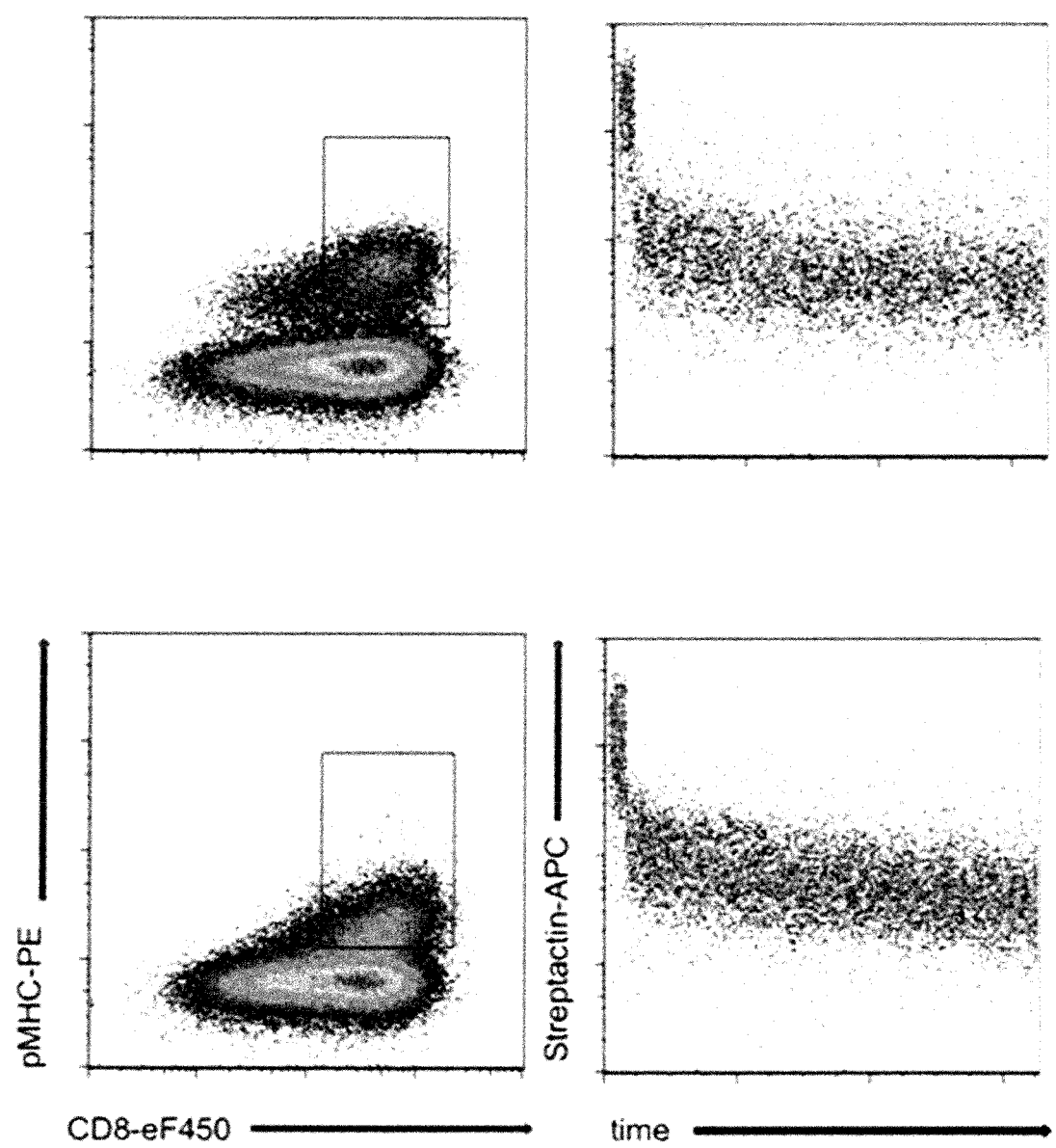
Figure 10:
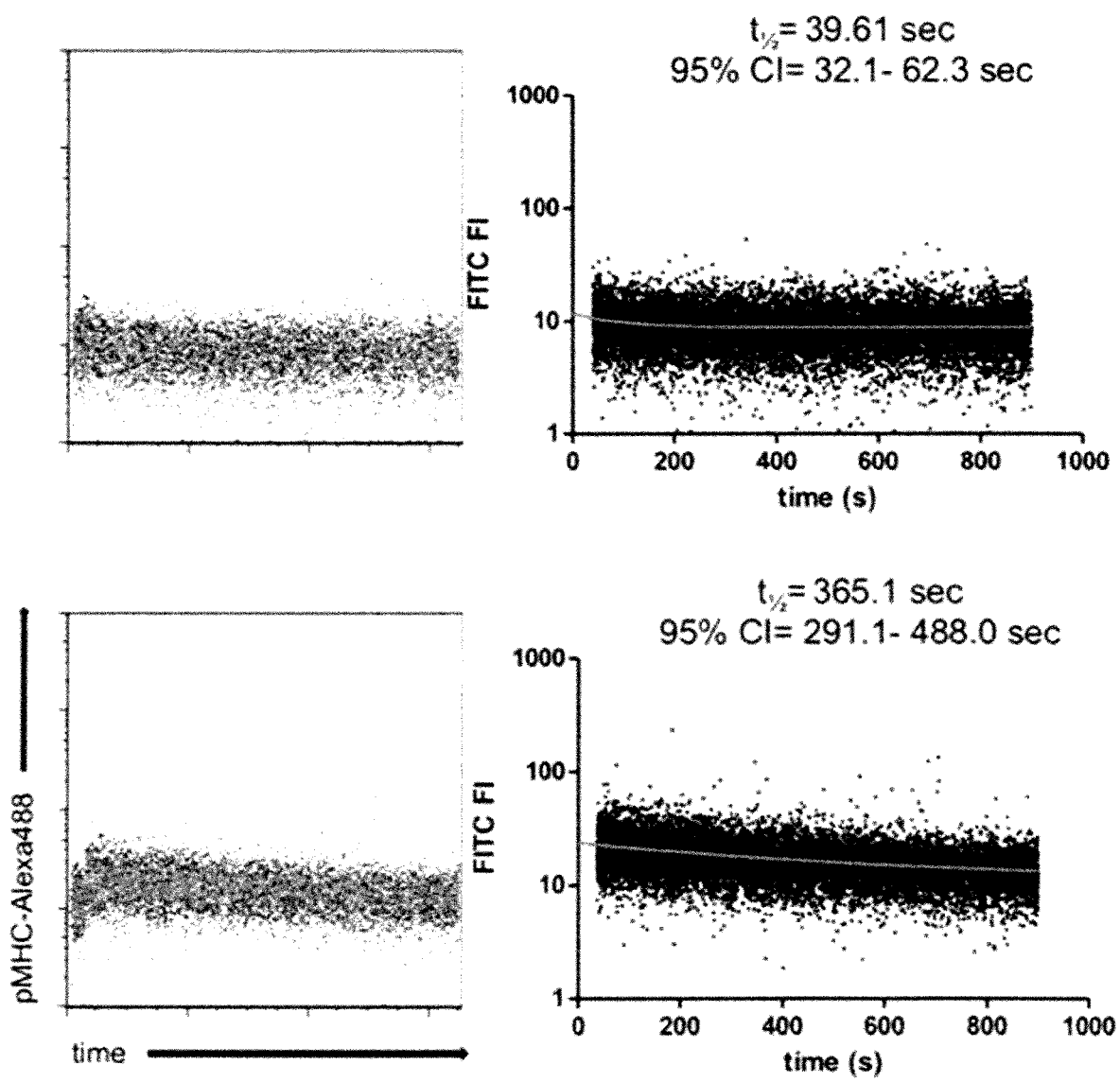

FIG. 10: Functional Characterization of Isolated TCRs Using $k_{off}$ Rate Measurement on CD8+ J76 Tumor Cells.

Two HLA*02 01/CMVpp65 specific TCRs were isolated using single clone PCR. To analyze their structural avidity, TCRs were transduced into CD8+ J76 tumor cells lacking an endogenous TCR. Boolean gating on single living CD8+ non-reversible pMHC-PE+ T cells. Data of Streptactin APC and reversible pMHC-Alexa488 over time were exported to GraphPad PRISM to fit an exponential decay curve to determine the $k_{off}$ rate.

Figure 11:
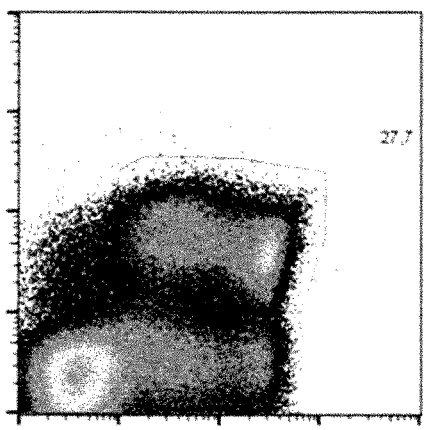
Figure 11:
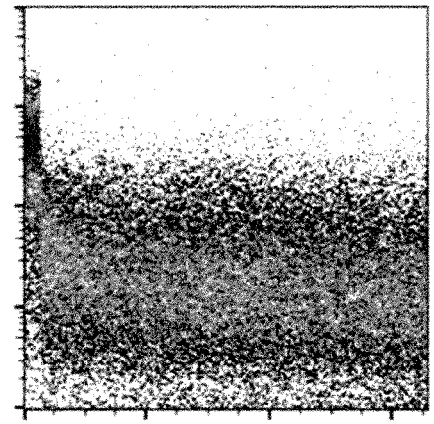
Figure 11:
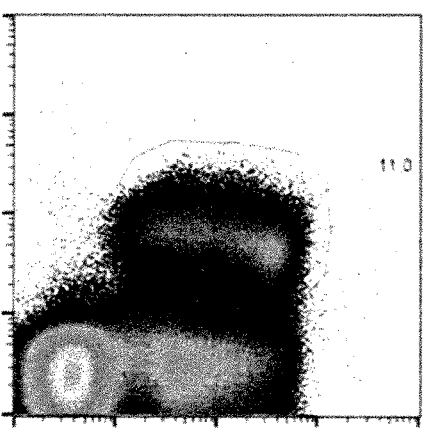
Figure 11:
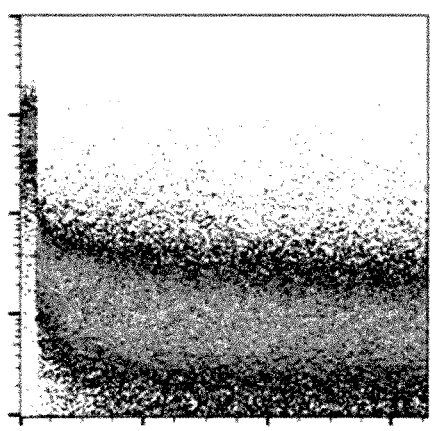
Figure 11:
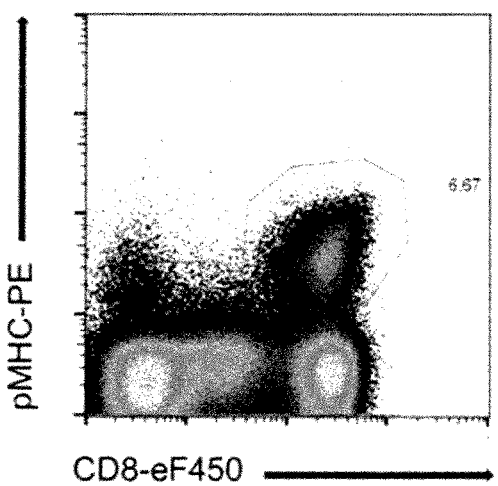
Figure 11:
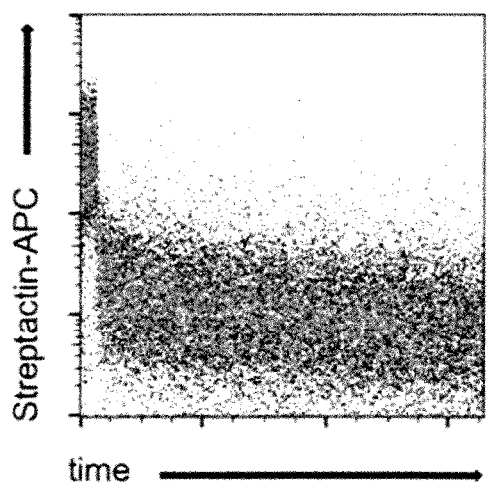
Figure 11:
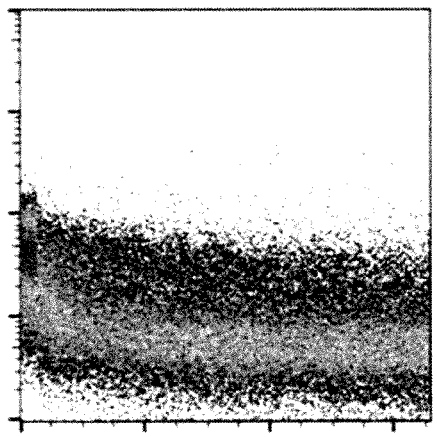
Figure 11:
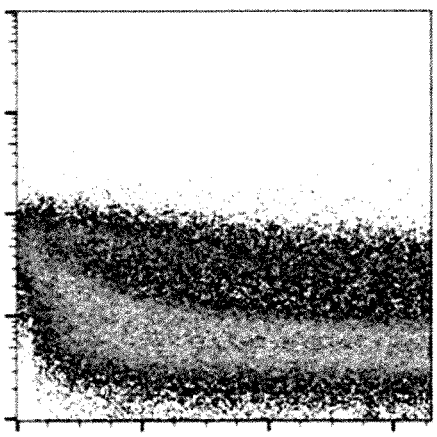
Figure 11:
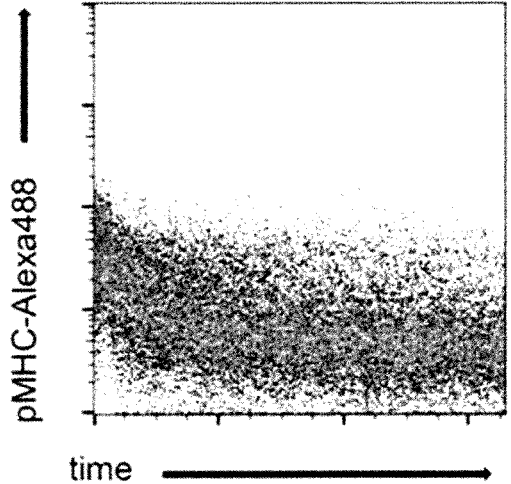

FIG. 11: $k_{off}$ Rate Measurement in a Murine Model System for High and Low Avidity TCR pMHC Interaction.

Row a.: SIIQFEKL:H2kb (SEQ ID NO:14), row b.: SIYNFEKL:H2kb (SEQ ID NO: 15); row c.: SIINFEKL:H2kb (SEQ ID NO: 15).

DETAILED DESCRIPTION

For some applications, e.g. the measurement of homogenous populations like T cell clones or transduced T cells, single cell resolution is not necessary and a method allowing fast screening of $k_{off}$-rate values using commonly available instrumentation would be desirable. The inventors of the present application therefore aimed to transfer the principle of the reversible multimer based $k_{off}$-rate assay to applications guided by conventional flow cytometry. The inventors have surprisingly demonstrated that $k_{off}$-rate kinetics can indeed be acquired with high sensitivity by flow cytometry; thereby, the procedure generates highly reliable dissociation measurements with values comparable to a microscopy guided assay. The inventors have further surprisingly demonstrated that this procedure may be transferred to the analysis of antigen-specific T cell populations directly ex vivo. These results could not have been expected before, because in vivo antigen specific T cell populations are often quite small and the presence of additional (unspecific) cells limits the tracking of staining kinetics, like it is necessary for $k_{off}$-rate measurements. Hebeisen et al. 2015, Cancer Res, 75(10):1983-91 proposed to combine $k_{off}$-rate measurements with previous sorting or cloning of analyzed T cells. However, the present inventors have recognized that this is not only a time consuming procedure, it also bears the risk to bias obtained results as in vitro expansions protocols often change the composition of complex T cell populations. Therefore, the inventors envisioned a direct assessment of $k_{off}$-rate values without cell sorting and in vitro cell expansion by double staining of antigen-specific T cells with reversible and non-reversible specific MHC multimers. Staining with non-reversible multimers allows to stably identify the antigen-specific target population while observing the dissociation of the reversible multimers. Importantly, the inventors of the present application were able to demonstrate that the dissociation kinetics of the pMHCs are not influenced by additional staining with non-reversible multimers. Hence, multimer double staining in combination with flow cytometry-guided TCR-ligand $k_{off}$-rate measurement can be used for analyzing even very small antigen-specific T cell populations directly ex vivo.

The present invention therefore encompasses a method of determining the dissociation rate constant ($k_{off}$) of a receptor molecule R on a target cell and a first receptor binding site B1, comprising detecting a first detectable label attached to the target cell and a second detectable label attached to the target cell. While the first detectable label may be reversibly bound to the cell, the second detectable label may be essentially irreversibly bound to the cell. For this purpose, the cell has been contacted with (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and a first multimerization reagent, the first multimerization reagent comprising at least two first binding sites Z1 for the reversible binding of the first binding partner C1 of the first receptor binding reagent. The first multimerization reagent preferably comprises at least 3, preferably at least 3, preferably 4-20, preferably 4-8, preferably 4 first binding sites Z1. The first receptor binding reagent (i) and the first multimerization reagent (ii) form a first multivalent binding complex that binds to said target cell, the first multivalent binding complex comprising at least two of said first receptor binding reagents bound to one said first multimerization reagent. The first multivalent complex preferably comprises at least 3, preferably at least 4, preferably 4-20, preferably 4-8, preferably 4 first receptor binding reagents bound to one said first multimerization reagent. It is understood that the first detectable label is bound or capable of binding to said first receptor binding reagent. It is further understood that said second detectable label is essentially irreversibly attached to said receptor molecule R. It is also understood that the first detectable label and the second detectable label are different from each other, meaning that they are not the same compound. The first multimerization reagent optionally further comprises a third detectable label. It is understood that each of the first, second, and third detectable label are preferably different from each other and can preferably be distinguished from each other.

In this context, it is noted that the formation of a complex (C) between a receptor binding reagent B and its receptor R, e.g. a cell surface receptor molecule can be described by a two-state process noted $$C \rightleftharpoons B+R$$

The corresponding dissociation $K_d$ constant is defined as $$K_d = \frac{[B]+[R]}{[C]}$$

wherein [B], [R], and [C] are the equilibrium molar concentrations of the receptor, the receptor binding reagent (ligand) and the respective complex at a given temperature and pressure. The dissociation $K_d$ constant can also be expressed as the ratio of the constant of the on-rate ($k_{on}$) for the speed of association/formation (also called association rate constant) of the complex and the constant of the off-rate ($k_{off}$) for the dissociation of the complex (also called dissociation rate constant) with $$K_d = \frac{k_{off}}{k_{on}}$$

In the present application, the values of the thermodynamic and kinetic constants $K_d$, $k_{on}$ and $k_{off}$ refer to their determination at a temperature of 4° C. and atmospheric pressure of 1.013 bar.

As used herein, "reversible", when used in the context of a monovalent binding complex, may be expressed in terms of the $k_{off}$ rate for the binding between two binding partners, e.g. the binding between a receptor molecule R and its binding partner B. The $k_{off}$ rate for reversible binding may be about $0.5 \times 10^{-4}$ sec$^{-1}$ or greater, about $1 \times 10^{-4}$ sec$^{-1}$ or greater, about $2 \times 10^{-4}$ sec$^{-1}$ or greater, about $3 \times 10^{-4}$ sec$^{-1}$ or greater, about $4 \times 10^{-4}$ sec$^{-1}$ of greater, about $5 \times 10^{-4}$ sec$^{-1}$ or greater, about $1 \times 10^{-3}$ sec$^{-1}$ or greater, about $1.5 \times 10^{-3}$ sec$^{-1}$ or greater, about $2 \times 10^{-3}$ sec$^{-1}$ or greater, about $3 \times 10^{-3}$ sec$^{-1}$ or greater, about $4 \times 10^{-3}$ sec$^{-1}$, about $5 \times 10^{-3}$ sec$^{-1}$ or greater, about $1 \times 10^{-2}$ sec$^{-1}$ or greater, or about $5 \times 10^{-1}$ sec$^{-1}$ or greater. The respective $K_D$ value of such a reversible binding complex may be in the range of about $1 \times 10^{-10}$ M or greater, about $1 \times 10^{-9}$ M or greater, about $1 \times 10^{-8}$ M or greater, about $1 \times 10^{-7}$ M or greater, about $1 \times 10^{-6}$ M or greater, about $1 \times 10^{-5}$ M or greater, about $1 \times 10^{-4}$ M or greater, about $1 \times 10^{-3}$ M or greater. In contrast thereto, "irreversible" or "essentially irreversible", which is used synonymously and interchangeable, may also be expressed in terms of a $k_{off}$ rate. The $k_{off}$ rate for an (essentially) irreversible binding, e.g. between a receptor molecule R and its binding partner B, may be about $1 \times 10^{-5}$ sec$^{-1}$ or lower, about $1 \times 10^{-6}$ sec$^{-1}$ or lower, about $1 \times 10^{-7}$ sec$^{-1}$ or lower, about $1 \times 10^{-8}$ sec$^{-1}$ or lower, about $1 \times 10^{-9}$ sec$^{-1}$ or lower, about $1 \times 10^{-10}$ sec$^{-1}$ or lower. The respective $K_D$ value of such a irreversible binding complex may be in the range of about $2 \times 10^{-10}$ M or less, about $1 \times 10^{-11}$ M or less, or about $1 \times 10^{-12}$ M or less, about $1 \times 10^{-13}$ M or less, or about $1 \times 10^{-14}$ M or less. It may be in the range of $2 \times 10^{-10}$ M to about $10^{-15}$ M. The term "about" when used herein in relation to the $k_{off}$ rate, the $k_{on}$ rate or the $K_d$ is meant to include an error margin of ±0.1%, ±0.2%, ±0.3%, ±0.4%, ±0.5%, ±0.7±0.9, %±1.0, %, ±1.2%, ±1.4%, ±1.6%, ±1.8%, ±2.0%, ±2.2%, ±2.4,%, ±2.6%, ±2.8%, ±3.0%, ±3.5%, ±4.0.%, ±4.5%, ±5.0%, ±6.0%, ±7.0%±, 8.0%, ±9.0%±, 10.0%, ±15.0%, or ±20.0%. However, since a receptor molecule R may be typically present in two or more copies on the surface of a target cell, an avidity effect may have to be considered if a reagent that binds to the cell comprises two or more binding sites B. In such a case, although the binding between a single receptor R and a single binding site B may be reversible, the binding of a cell comprising multiple R and a reagent comprising multiple binding sites B may be essentially irreversible. For such a multivalent binding, an apparent $k_{off}$-value may be defined, wherein the apparent $k_{off}$ value is the $k_{off}$ value that may apparently be measured, if assumed that the binding is monovalent. As discussed, due to the avidity effect, binding of a cell comprising two or more receptors R and a reagent, e.g. a multimeric reagent, comprising more than one binding sites B may be essentially irreversible, e.g. the apparent $k_{off}$ value may be in the range as defined for an irreversible binding. However, it is possible to reversibly multimerize multiple binding reagents that each comprise a binding site B. For this purpose, a multimerization reagent may be used that comprise at least two binding sites Z. The binding reagent comprises, further to the binding site B, a binding partner C, which may bind to the binding site Z on the multimerization reagent. Here, the binding between C and Z is reversible, and it can preferably be disrupted, e.g. by adding reagents that compete with C for the binding site Z and may displace C from the C:Z complex. Hence, a reversible multimer that has two or more binding reagents bound to it, each comprising a binding site B, may bind to a cell comprising two or more receptors R with a high avidity and an apparent $k_{off}$ value which would normally indicate essentially irreversible binding as long as it is in the form of a multimer. The binding to the cell may still be reversible, if the multimerization itself can be reversed as described herein and the monovalent binding of the binding site B with the receptor R is reversible. Such reversible binding by a reversible multimer is e.g. described in U.S. Pat. No. 7,776,562, International Patent application WO 02/054065, or International Patent application WO 2013/011011.

As used herein, "detectable label" refers to detectable entities that can be used for the detection of a stained cell in flow cytometry. Preferably, the label does not negatively affect the characteristics of the cells to be stained or isolated. Examples of labels are fluorescent labels such as phycoerythrin, allophycocyanin (APC), Brilliant Violet 421, Alexa Fluor 488, coumarin or rhodamines to name only a few. The label may be bound to the receptor binding reagent and/or the multimerization reagent. When applicable, a first detectable label is preferably bound to a receptor binding reagent, while an optional third detectable label is preferably bound to a multimerization reagent. The label may be a direct label, i.e. a label bound to one of the members of the multivalent binding complex as specified above. In such a case, the label might, for example, be covalently coupled (conjugated) to either the receptor binding reagent or the multimerization reagent. Alternatively, the label may be an indirect label, i.e. a label which is bound to a further reagent which in turn is capable of binding to one of the members of the multivalent binding complex as specified above. Such a label may be added before, during or after the multivalent binding complex has been formed. An example for such an indirect label is a bis-, tris-, or tetrakis-NTA containing fluorescent dye as described by Lata et al., J. Am. Chem. Soc. 2005, 127, 10205-10215 or Huang et al., Bioconjugate Chem. 2006, 17, 1592-1600. Said label is capable of binding non-covalently (via metal chelation) to an oligohistidine tag. Thus, in this example, the receptor binding reagent and/or the multimerization reagent may carry an oligohistidine tag (for example, a Fab fragment as receptor binding reagent that has an oligohistidine tag such as a hexa-histidine tag fused to the C-terminus of the CH1 or the CL-domain or a streptavidin mutein such as the commercially available Strep-Tactin® mutein (IBA GmbH, Göttingen, Germany) as multimerization reagent that has an oligohistidine tag fused to the N- or C-terminus of one of its subunits can be used), thereby being enabled to non-covalently bind such a NTA based fluorescent dye compound described by Lata et al, supra or Huang et al, supra. Such a non-covalently binding label needs not necessarily be bound to its target (receptor binding reagent and/or the multimerization reagent) before the multivalent binding complex is formed but can also be added to the sample when the multivalent binding complex forms or after the multivalent binding complex has been formed. Such a non-covalently binding label can also be added after the multivalent binding complex is bound to the target cells. Instead of the NTA comprising fluorescent dye:oligohistidine tag binding pair described above, also any other specific binding pair such as, for example, digoxigenin and an anti digoxigenin antibody or antibody fragment carrying the fluorescent or other label can be used for indirect labeling. In such a case, the receptor binding reagent and/or the multimerization reagent is conjugated to/coupled with digoxigenin and an anti digoxigenin antibody or antibody fragment carrying the chosen label binds (via digoxigenin) to the multimerization reagent or the receptor binding reagent. The invention encompasses that the first detectable label or the second detectable label may both be a fluorescent dye. An optional third detectable label may also be a fluorescent dye. It is preferred that the first detectable label is a first fluorescent dye and the second detectable label is a second fluorescent dye, wherein the emission signal of the first fluorescent dye can preferably be distinguished from the emission signal of the second fluorescent dye. An optional third detectable label may also be a fluorescent dye that can preferably be distinguished from both the first and the second fluorescent dye. As an illustrative example, the first detectable label may be Alexa Fluor 488 (Alexa488), while the second detectable label may be Brilliant Violet 421 (BV421). The optional third detectable label may be allophycocyanin (APC).

As discussed, the target cell has a second detectable label attached to it, wherein the second detectable label is essentially irreversibly attached to the receptor molecule R. It is understood that there are multiple possibilities for essentially irreversibly attaching such said second label to a one or more receptor molecule(s) R. The invention thus envisions, as one possibility, that the second detectable label is attached to the cell via an irreversible multimer. For this purpose, the cell may have further been contacted with (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent. The second multimerization reagent preferably comprises at least 3, preferably at least 3, preferably 4-20, preferably 4-8, preferably 4 second binding sites Z2. The stable binding between the second binding partner C2 and the second binding site Z2 may be an essentially irreversible binding as defined herein. Hence, the dissociation rate constant ($k_{off}$) for the binding between said second binding partner C2 and said second binding sites Z2 can, for example, be in the range as defined herein for an essentially irreversible binding. Here, the second receptor binding reagent (iii) and the second multimerization reagent (iv) form a second multivalent binding complex that binds to said target cell, the second multivalent binding complex comprising at least two of second receptor binding reagents bound to one said second multimerization reagent, and said second detectable label is bound to said second multivalent binding complex. Alternatively, the binding between the second binding partner C2 and the second binding site Z2 may be a reversible binding, and the second binding partner C2 and the second binding site Z2 may be any pair of compounds that are defined for C1 and Z1, with the proviso that the bond between C2 and Z2 cannot disrupted by the same method, by which the bond between C1 and Z1 can be disrupted. As an illustrative example, C1 may be a streptavidin binding affinity peptide and Z1 may be streptavidin mutein such as streptactin, while C2 may be an oligohistidine tag and Z2 is a compound that comprises a divalent cation. If biotin is added to these complexes, the bond between C1 and Z1 will be disrupted, while the bond between C2 and Z2 will stay intact. Hence, although the bond C2 and Z2 can generally be disrupted (e.g. by contacting the complex with a metal-chelating agent, such as EDTA), it can still serve as an irreversible multimer in the methods of the invention, as long as the bond between C2 and Z2 is not disrupted by the same means or methods, by which the bond between C1 and Z1 can be disrupted. Consequently, the binding between Z2 and C2 is preferably irreversible, or preferably not disruptable by the means that may disrupt the binding between Z1 and C1. The second multivalent complex preferably comprises at least 3, preferably at least 4, preferably 4-20, preferably 4-8, preferably 4 second receptor binding reagents bound to one said second multimerization reagent. Hence, it is preferably possible to selectively disrupt the binding between Z1 and C1 while the binding between Z2 and C2 stays intact. Hence, it may be possible to selectively reverse the attachment of the first detectable label to the cell, while the second detectable label will remain attached to the cell. It is further understood that B1 and B2 may be the same or different. It is preferred that B1 and B2 are the same.

Another possibility for essentially irreversibly attaching a second detectable label to the target cell may be using a binding reagent that comprises multiple B2 binding sites. Hence, it is encompassed that the method of the invention may comprise that the cell has further been contacted with (iii') a multimeric receptor binding reagent M2, wherein the multimeric second receptor binding reagent comprising at least two second receptor binding sites B2, preferably at least 3, preferably at least 4, preferably 4-20, preferably 4-8, preferably 4 receptor binding sites B2, wherein the second receptor binding site B2 specifically binds to said receptor molecule R, wherein the multimeric receptor binding reagent M2 essentially irreversibly binds to said target cell via said receptor molecule R, and wherein said second detectable label is bound to said multimeric receptor binding reagent M2. Here the apparent dissociation rate constant ($k_{off}$) for the binding between said multimeric receptor binding reagent M2 and said target cell can, for example, be about $1 \times 10^{-5}$ sec$^{-1}$ or lower, about $1 \times 10^{-6}$ sec$^{-1}$ or lower, about $1 \times 10^{-7}$ sec$^{-1}$ or lower, about $1 \times 10^{-8}$ sec$^{-1}$ or lower, about $1 \times 10^{-9}$ sec$^{-1}$ or lower, about $1 \times 10^{-10}$ sec$^{-1}$ or lower. Here again, it is understood that B1 and B2 may be the same or different, preferably the same.

Essentially irreversibly attaching a second detectable label to the target cell may also be achieved by using an agent that irreversibly binds to a receptor R. The invention thus encompasses that the method of the invention may comprise that the cell has further been contacted with (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, and wherein said second detectable label is bound to said irreversible receptor binding reagent I2. It is understood, that for binding to R, I2 may comprise an irreversible binding site B3, that essentially irreversibly binds to R and that is preferably different from B1. Here the dissociation rate constant ($k_{off}$) for the binding between said irreversible binding site B3 and said receptor molecule R can, for example, be about $1 \times 10^{-5}$ sec$^{-1}$ or lower, about $1 \times 10^{-6}$ sec$^{-1}$ or lower, about $1 \times 10^{-7}$ sec$^{-1}$ or lower, about $1 \times 10^{-8}$ sec$^{-1}$ or lower, about $1 \times 10^{-9}$ sec$^{-1}$ or lower, about $1 \times 10^{-10}$ sec$^{-1}$ or lower.

In the method of the invention, virtually any said target cell can be used that has at least one common receptor molecule that can be used for $k_{off}$ rate measurement. In order to achieve an avidity effect, the receptor molecule is typically present in two or more copies on the surface of the target cell. In typical embodiments the target cell is a eukaryotic or prokaryotic cell, preferably a mammalian cell. The mammalian cell may be a lymphocyte or a stem cell. Hence, the target cell may be a T cell, a T helper cell, a B cell or a natural killer cell, such as a CMV-specific a CMV-specific CD8+ T-lymphocyte, a cytotoxic T-cell a, memory T-cell and a regulatory T-cell. Likewise, the at least one common (specific) receptor which defines the target cell population may be any receptor for which a $k_{off}$ rate of the binding to a given binding site B1 can be determined. For example, the receptor may be a receptor defining a population or subpopulation of immune cells, e.g. a population or subpopulation of T cells, T helper cells, for example, CD4+ T-helper cells, B cells or natural killer cells. Examples of T cells include cells such as CMV-specific CD8+ T-lymphocytes, cytotoxic T cells, memory T cells and regulatory T cells (Treg). The receptor molecule R may be any receptor present on the target cell. However, it is preferred that the receptor is an antigen-specific receptor, such as e.g. a T cell receptor or a B cell receptor. The receptor may preferably be a T cell receptor while the target cell may preferably be a CD8+ T cell. In this context, it is noted that the term "target cells" as used herein encompasses all biological entities/vesicles in which a membrane (which can also be a lipid bilayer) separates the interior from the outside environment and which comprise specific receptor molecules on the surface of the biological entity. Examples of such entities include, but are not limited to, a cell, a virus, a liposome, an organelle such as mitochondria, chloroplasts, a cell nucleus or a lysosome.

In the methods of the invention, the first receptor binding site B1 of the receptor binding reagent which specifically binds to said receptor molecule R can for example be an MHC molecule. The use of MHC molecules as first receptor binding site B1 allow the characterization of a $k_{off}$ rate of a T cell receptor of an antigen-specific subpopulation of T cells directly ex vivo. It is noted that the term "MHC molecule" includes MHC molecules that are conjugated with a peptide. The first receptor binding site B1 may also be an antibody or a divalent antibody fragment such as an (Fab)$_2$'-fragment, divalent single-chain Fv fragment. It might also be a bivalent proteinaceous artificial binding molecule such as a dimeric lipocalin mutein that is also known as "duocalin". In other embodiments the receptor binding reagent may have a single binding site B1, i.e., may be monovalent. Examples of monovalent receptor binding reagents include, but are not limited to, a monovalent antibody fragment or a proteinaceous binding molecule with antibody-like binding properties, such as a lipocalin mutein.

As discussed herein, the bond between the first binding partner C1 and the first binding site Z1 should be reversible, i.e. the bond should be capable of being disrupted under conditions suitable for carrying out the claimed method. The dissociation rate constant ($k_{off}$) for the binding between said first binding partner C1 and said first binding sites Z1 can, for example, be as defined herein for a reversible binding, e.g. in the range of about $5\times10^{-4}$ sec$^{-1}$. Also the $k_{off}$ of this bond can be determined by any suitable means, for example, by fluorescence titration, equilibrium dialysis or surface plasmon resonance. The dissociation/removal of the staining of the multimerization reagent from the cells results in the removal of the dissociated receptor binding reagent, and thus of the whole multivalent binding complex including the detectable label from the previously stained cell.

According to the invention, the receptor binding reagent may be selected such that it comprises at least one first binding partner C1 and the first multimerization reagent comprises at least two first binding sites Z1, at least three or at least four first binding sites Z1 for the first binding partner C1. Alternatively, it is possible to use two different (kinds of) receptor binding reagents.

According to the invention, the partners can be chosen from the following group: (a) said first binding partner C1 comprises a streptavidin or avidin binding peptide and said first multimerization reagent comprises streptavidin, or avidin, or a streptavidin analog, or an avidin analog that reversibly binds to said streptavidin or avidin binding peptide; or (b) said first binding partner C1 comprises a biotin analog that reversibly binds to streptavidin or avidin and said first multimerisation reagent comprises streptavidin, or avidin, or a streptavidin analog, or an avidin analog that reversibly binds to said biotin analog. Said first binding partner C1 may comprise the streptavidin-binding peptide Trp-Ser-His-Pro-Gln-Phe-Glu-Lys (SEQ ID NO: 01) and said multimerization reagent comprises the streptavidin analog having the amino acid sequence Val$^{44}$-Thr$^{45}$-Ala$^{46}$-Arg$^{47}$ (SEQ ID NO: 02) at positions 44 to 47 of the wild-type streptavidin sequence or the streptavidin analog having the amino acid sequence Ile$^{44}$-Gly$^{45}$-Ala$^{46}$-Arg$^{47}$ (SEQ ID NO: 03) at positions 44 to 47 of the wild-type streptavidin sequence. Both these muteins are described in U.S. Pat. No. 6,103,493, for example, and are commercially available under the trademark Strep-Tactin® from IBA GmbH, Göttingen, Germany. The streptavidin binding peptides might, for example, be single peptides such as the "Strep-tag®" described in U.S. Pat. No. 5,506,121, for example, or streptavidin binding peptides having a sequential arrangement of two or more individual binding modules as described in International Patent Publication WO 02/077018. Examples of streptavidin binding peptides having a sequential arrangement of two or more individual binding modules include the di-tag3 sequence (WSHPQFEKGGGSGGGSGGGSWSHPQFEK; SEQ ID NO: 11), the di-tag2 sequence Trp-Ser-His-Pro-Gln-Phe-Glu-Lys-(GlyGlyGlySer)$_2$-Trp-Ser-His-Pro-Gln-Phe-Glu-Lys (SEQ ID NO: 12) that are described in International Patent Application WO02/077018 or U.S. Pat. No. 7,981,632 or the sequence WSHPQFEKGGGSGGGSGG-SAWSHPQFEK (SEQ ID NO: 13, also known as Twin-Strep-tag®).

The present invention also encompasses that the binding between the first binding partner C1 and said at least 2 first binding sites Z1 of said multimerization reagent may occur in the presence of a divalent cation. In an illustrative example, the first binding partner C1 comprises a calmodulin binding peptide and the multimerization reagent comprises multimeric calmodulin as described in U.S. Pat. No. 5,985,658, for example. Alternatively, the first binding partner C1 may comprise a FLAG peptide and said first multimerization reagent may comprise an antibody binding to the FLAG peptide, e.g. the FLAG peptide, which binds to the monoclonal antibody 4E11 as described in U.S. Pat. No. 4,851,341. In yet another illustrative example, the first binding partner C1 comprises an oligohistidine tag and the first multimerization reagent comprises an antibody or a transition metal ion binding the oligohistidine tag. The disruption of all these binding complexes may be accomplished by metal ion chelation, e.g. calcium chelation, e.g. by addition of EDTA or EGTA. Calmodulin, antibodies such as 4E11 or chelated metal ions or free chelators may be multimerized by conventional methods, e.g. by biotinylation and complexation with streptavidin or avidin or multimers thereof or by the introduction of carboxyl residues into a polysaccharide, e.g. dextran, essentially as described in Noguchi, A., Takahashi, T., Yamaguchi, T., Kitamura, K., Takakura, Y., Hashida, M. & Sezaki, H. (1992). "Preparation and properties of the immunoconjugate composed of anti-human colon cancer monoclonal antibody and mitomycin C dextran conjugate. Bioconjugate Chemistry 3, 132-137" in a first step and coupling of calmodulin or antibodies or chelated metal ions or free chelators via primary amino groups to the carboxyl groups in the polysaccharide, e.g. dextran, backbone using conventional carbodiimide chemistry in a second step.

In the method of the invention, it is also possible that the multimerization reagent is an oligomer or a polymer of streptavidin or avidin or of any analog of streptavidin or avidin. The oligomer or polymer may be crosslinked by a polysaccharide. Oligomers or polymers of streptavidin or of avidin or of analogs of streptavidin or of avidin may be prepared by the introduction of carboxyl residues into a polysaccharide, e.g. dextran, essentially as described in "Noguchi, A., Takahashi, T., Yamaguchi, T., Kitamura, K., Takakura, Y., Hashida, M. & Sezaki, H. (1992). Preparation and properties of the immunoconjugate composed of anti-human colon cancer monoclonal antibody and mitomycin C dextran conjugate. Bioconjugate Chemistry 3, 132-137" in a first step. Then streptavidin or avidin or analogs thereof may be coupled via primary amino groups of internal lysine residue and/or the free N-terminus to the carboxyl groups in the dextran backbone using conventional carbodiimide chemistry in a second step. However, cross-linked oligomers or polymers of streptavidin or avidin or of any analog of streptavidin or avidin may also be obtained by crosslinking via bifunctional linkers such as glutardialdehyde or by other methods described in the literature.

The invention further encompasses that the first binding partner C1 may comprise an antigen and the multimerization reagent may comprise an antibody or antibody fragment against said antigen. The antigen may, for example, be an epitope tag. Examples of suitable epitope tags include, but are not limited to, FLAG-tag (sequence: DYKDDDDK, SEQ ID NO: 04), Myc-tag (sequence: EQKLISEEDL, SEQ ID NO: 05), HA-tag (sequence: YPYDVPDYA, SEQ ID NO: 06), VSV-G-tag (sequence: YTDIEMNRLGK, SEQ ID NO: 07), HSV-tag (sequence: QPELAPEDPED, SEQ ID NO: 08), and V5-tag (sequence: GKPIPNPLLGLDST, SEQ ID NO: 09). The antigen may also be a protein, for example, the first binding partner C1 may comprise maltose binding protein (MBP), chitin binding protein (CBP) or thioredoxin as an antigen. In these cases, the complex formed between the at least two first binding sites Z1 of the multimerization reagent (antibody) and the antigen can be disrupted by adding the free antigen, i.e. the free peptide such as a Myc-tag or the HA-tag (epitope tag) or the free protein (such as MBP or CBP). In this context, it is noted that in case the FLAG-tag is used as first binding partner C1 and the first multimerization reagent comprises an antibody or antibody fragment binding the FLAG tag, it is also possible of disrupting this reversible bond by addition of the free FLAG peptide.

The invention also encompasses that the first binding partner C1 may comprise glutathione S-transferase (GST) and said first multimerization reagent may comprise glutathione as first binding site Z1 or wherein said first binding partner C1 may comprise a glutathione and said first multimerization reagent may comprises glutathione S-transferase as first binding site Z1. Here, the bond between the GST and glutathione can be dissociated by addition of excess glutathione. The free glutathione may competitively displace the glutathione comprised in C1 or Z1 that is bound to GST, allowing the first receptor binding agent to dissociate from the first multimerization reagent.

The invention also encompasses that the first binding partner C1 may comprise an immunoglobulin Fc portion and said first multimerization reagent may comprise a protein selected from the group consisting of protein A, protein G, protein a/g, and protein L, or wherein said first binding partner C1 as first binding site Z1 comprises a protein selected from the group consisting of protein A, protein G, protein a/g, and protein L and said first multimerization reagent comprises an immunoglobulin Fc portion as first binding site Z1. The bond between the immunoglobulin Fc portion and the protein A, protein G, protein a/g, or protein L may e.g. be disrupted by applying an acidic pH.

The invention further contemplates that the second receptor binding site B2 comprised in the second receptor binding reagent or comprised in the multimeric receptor binding reagent M2 can generally be any compound that is defined herein for the first receptor binding reagent B1. It is preferred that B2 is a MHC molecule. It is further encompassed that the second receptor binding site B2 may preferably be the same as the first receptor binding site B1. The second receptor binding site B2 may also be an antibody, a divalent antibody fragment, a monovalent antibody fragment, and a proteinaceous binding molecule with antibody-like binding. Examples for a divalent antibody fragment comprise, but are not limited to divalent antibody fragment is an (Fab)$_2$'-fragment, or a divalent single-chain Fv fragment. Examples of monovalent antibody fragments include, but are not limited to an Fab fragment, an Fv fragment, a single domain antibody, and a single-chain Fv fragment (scFv).

Examples of proteinaceous binding molecules with antibody-like binding properties that can be used as receptor binding reagent that specifically binds the receptor molecule include, but are not limited to, an aptamer, a mutein based on a polypeptide of the lipocalin family, a glubody, a protein based on the ankyrin scaffold, a protein based on the crystalline scaffold, an adnectin, an avimer, a EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, a adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

The invention further encompasses that the irreversible receptor binding site B3 comprised in the irreversible receptor binding reagent I2 may be an antibody, an divalent antibody fragment, a monovalent antibody fragment, and a proteinaceous binding molecule with antibody-like binding. It is understood that the irreversible receptor binding site B3 is preferably not the same compound as the first receptor binding site B1.

The invention further encompasses that the second binding partner C2 may comprise biotin or a biotin analog and said second multimerization reagent may comprise a streptavidin analog or an avidin analog as second binding site Z2 that essentially irreversibly binds to biotin or said biotin analog. As an illustrative example, the second binding partner C2 may be biotin and the second binding site Z2 may be streptavidin. At the same time, the first binding partner B1 may comprise a streptavidin-binding peptide as set forth in SEQ ID NO: 01 while the first binding site Z1 of the first multimerization reagent may comprise the streptavidin analog having the amino acid sequence Val$^{44}$-Thr$^{45}$-Ala$^{46}$-Arg$^{47}$ (SEQ ID NO: 02) at positions 44 to 47 of the streptavidin wild type sequence or the streptavidin analog having the amino acid sequence Ile$^{44}$-Gly$^{45}$-Ala$^{46}$-Arg$^{47}$ (SEQ ID NO: 03) at these sequence positions 44 to 47. Here, when contacting the multimeric complexes with excess free biotin, the streptavidin-binding peptide comprised in C1 is displaced from the first binding site Z1, while the biotin comprised in C2 remains bound to the second binding site Z2. The first multimerization reagent may thus dissociate from the target cell thus allowing measurement of the $k_{off}$ rate of receptor and the first receptor binding site B1, while the second multimerization reagent stays attached to the target cell.

Alternatively, the second binding partner C2 and the second binding site Z2 may be any pair of compounds that are defined for C1 and Z1, with the proviso that the bond between C2 and Z2 cannot disrupted by the same method, by which the bond between C1 and Z1 can be disrupted. As an illustrative example, C1 may be a strep-tag and Z1 may be streptactin, while C2 may be an oligohistidine tag and Z2 is a compound that comprises a divalent cation. If biotin is added to these complexes, the bond between C1 and Z1 will be disrupted, while the bond between C2 and Z2 will stay intact. Hence, although the bond C2 and Z2 can generally be disrupted (e.g. by contacting the complex with a metal-chelating agent, such as EDTA), it can still serve as an irreversible multimer in the methods of the invention, as long as the bond between C2 and Z2 is not disrupted by the same means or methods, by which the bond between C1 and Z1 can be disrupted.

The methods of the invention may comprise a step of contacting the target cell that comprises a receptor molecule R with a first receptor binding reagent and said first multimerization reagent. Contacting these three components with each other can be conducted in any order. As an illustrative example, the first receptor binding agent may first be contacted with the first multimerization reagent to allow the formation of complexes of first receptor binding agent and first multimerization reagent and then contacting the two compounds with the target cell. As another illustrative example, the cell can be contacted first with the first receptor binding reagent, while the first multimerization reagent is subsequently be contacted with the cell and the first receptor binding reagent. As a further illustrative example, all three components may be contacted with each other simultaneously.

The method of the present invention may further comprise the step of contacting the target cell with a second receptor binding agent and a second multimerization reagent. Again, contacting these three components can be conducted in any order and the illustrative examples given for contacting the target cell with the first receptor binding reagent and the first multimerization reagent apply mutatis mutandis. Alternatively, the method of the present invention may further comprise the step of contacting the target cell with a multimeric receptor binding agent as described herein, or contacting the target cell with an irreversible receptor binding reagent as described herein. The step of contacting the target cell with the first receptor binding reagent and the first multimerization reagent may preferably be performed prior to contacting the cell with the second receptor binding agent and the second multimerization reagent or the multimeric receptor binding reagent or the irreversible receptor binding reagent. Optionally, a washing step can be conducted between these two steps.

The methods of the present invention may further comprise a step of disrupting the binding between the first receptor binding reagent and the first multimerization reagent. It is understood that this step may be carried out after the cell has been contacted with the first receptor binding reagent and the first multimerization reagent as well as the second receptor binding agent and the second multimerization reagent or the multimeric receptor binding reagent or the irreversible receptor binding reagent. Disruption of the binding between the first receptor binding reagent and the first multimerization reagent can be conducted by any suitable method known to the skilled person or described herein. For example, the binding can be disrupted by contacting the bound complex with a competition reagent CR. Here, the competition reagent CR may be capable to compete with first binding partner C1 for the binding to the first binding site Z1 on the first multimerization reagent. Suitable competition reagents are described herein and depend on the type of what first binding partner C1 is comprised in the first receptor binding reagent and what first binding site Z1 is comprised in the first multimerization reagent. As an illustrative example, where the first binding partner C1 is a streptavidin binding peptide and the first multimerization reagent may be a streptavidin mutein such as Strep-tactin®, the competition reagent CR may biotin or a biotin analog.

The binding between the first receptor binding reagent and the first multimerization reagent may also be conducted by metal ion chelation, e.g. by contacting the complex with a metal-chelating agent, such as EDTA or EGTA. This type of disrupting the binding reagent and the first multimerization reagent may also be conducted by metal ion chelation may for example be conducted if the first binding partner C1 is a oligohistidine tag and the first binding site Z1 comprises a divalent cation. Another method of disrupting the binding between the first receptor binding reagent and the first multimerization reagent is by pH shift. This method may for example be conducted if the first binding site Z1 comprises an immunoglobulin Fc region and the first binding site Z1 comprises a protein A.

In a preferred embodiment, the target cell is a T cell, preferably a CD8+ T cell; the receptor R is a T cell receptor; the first receptor binding site B1 and the second receptor binding site B2 are the same and are both a MHC molecule; the first binding partner C1 comprises a streptavidin binding peptide and the first multimerization reagent comprises streptactin; the second binding partner comprises a biotin and the second multimerization reagent comprises streptavidin, a first detectable label (e.g. Alexa 488) is bound to the first receptor binding reagent, a second detectable (e.g. BV421) label is preferably bound to the second multimerization reagent; a third detectable label (e.g. APC) is preferably attached to the first multimerization reagent. It is understood that first, second, and the optional third detectable label can be distinguished from each other. Here, biotin can be used as a competition reagent CR for disrupting the reversible binding between C1 and Z1 of the steptactin.

The methods of the present invention may further comprise the step of detecting the first detectable label attached to the target cell and detecting the second detectable label attached to the target cell. Here, detecting both detectable labels may preferably be conducted after the step of disrupting the binding between the first receptor binding reagent and the first multimerization reagent. In cases where the first multimerization reagent comprises a third detectable label, the methods of the present invention may further comprise detecting the third detectable label. In addition, the methods of the present invention may comprise detecting (a) further detectable label(s). As an illustrative example, the target cell may be additionally stained with a CD8 antibody with a further detectable label, such as e.g. eF450. The target cell may also be stained with a dye that allows for discrimination between viable and dead cell. An illustrative example for such a dye is propidium iodide, which is an intercalating agent and a fluorescent molecule that is membrane impermeant and generally excluded from viable cells and which can thus be used for identifying dead cells.

It is contemplated by the invention that the detection of the detectable labels may be conducted by a flow cytometry based analysis. Flow cytometry based analysis is typically combined with optical detection to identify and classify cells and allows speed combined with high sensitivity and specificity. It allows a simultaneous multiparametric analysis of the physical and chemical characteristics of single cells flowing through an optical or electronic detection device. These specific physical and chemical characteristics may comprise the specific light scattering and/or fluorescent characteristics of each cell.

The present invention encompasses the use of two detectable labels that are directly or indirectly bound to a receptor molecule R. While the first detectable label is reversibly bound to the cell, binding of the second detectable label to the target cell/receptor molecule R is essentially irreversible. Thus, detection of a signal of the second detectable label may be indicative for the presence of the receptor molecule R on the target cell. While the presence of the second detectable label may be indicative for the presence of the receptor molecule R on the target cell, the presence or absence of the first detectable label on said cell may be indicative for the non-dissociation or the dissociation of the first receptor binding site B1 from the receptor molecule. Here, presence of the first detectable label is indicative for the non-dissociation of the first receptor binding site while the absence is indicative for the dissociation of the same. It is understood that the reduction of detection events of the first detectable label on a cell on which the second detectable signal is detected may be indicative for the kinetic of dissociation of the first receptor binding site B1 from the receptor molecule R. Such dissociation may follow the kinetic of an exponential decay. In analyzing the number of detection events for the first detectable label on a cell, where the second detectable label is present, the dissociation rate constant ($k_{off}$) for the binding of the receptor molecule R and the first receptor binding site B1 may be obtained by standard methods that are familiar to the skilled person (e.g. curve fitting).

The methods of the invention may generally allow for the determination of any $k_{off}$ values of the binding of a receptor molecule R on a target cell and a first receptor binding site B1. However, the method is preferably applied for a binding of a receptor molecule R on a target cell and a first receptor binding site B1, where the $k_{off}$ value is suspected to be within a range of about $10^0$ $sec^{-1}$ to about $10^{-4}$ $sec^{-1}$, preferably within a range of $10^{-1}$ $sec^{-1}$ to about $10^{-3}$ $sec^{-1}$.

The methods of the invention can be carried out at any suitable temperature. Typically, the contacting of the mixture containing the target cell with any of the first receptor binding reagent, the first multimerization reagent, the second receptor binding reagent, the second multimerization reagent, the multimeric receptor binding reagent M2 or the irreversible receptor binding reagent I2 and later the disruption of the binding between the first receptor binding reagent and the first multimerization reagent and also the detection of the any one of the first detectable label, the second detectable label or the third detectable label may be carried out at such temperatures, at which substantially no activation and/or no signaling events occur, which might result in an alteration of the target cell, e.g. the T cell phenotype, in case a T cell is to be stained or isolated. The methods of the present invention or each individual step of the methods of the invention may thus be preferably carried out at a temperature of ≤15° C. or carried out at a temperature of ≤4° C.

The invention further encompasses that the target cell may be comprised in a sample. The sample may comprise the target cell and a plurality of other cells. The sample may comprise a population of cells (e.g. CD8+ T cells) and the target cell may be a subpopulation thereof (e.g. CD8+ T cells specific for a certain antigen).

The sample may be from any suitable source, typically all sample of a body tissue or a body fluid such as blood. The sample may thus be peripheral blood sample. In the latter case, the sample might for example, be a population of peripheral blood mononuclear cells (PBMC) that can be obtained by standard isolation methods such as Ficoll gradient of blood cells. The cell population comprised in the sample may however also be in purified form and might have been isolated using a reversible cell staining/isolation technology as described patent in U.S. Pat. Nos. 7,776,562, 8,298,782, International Patent application WO02/054065 or International Patent Application WO2013/011011. Alternatively, the population of cells can also be obtained by cell sorting via negative magnetic immunoadherence as described in U.S. Pat. No. 6,352,694 B1 or European Patent EP 0 700 430 B1. If an isolation method described here is used in basic research, the sample might be cells of in vitro cell culture experiments. The sample will typically have been prepared in form of a fluid, such as a solution or dispersion.

The sample may be obtained from a subject. A "subject" as used herein, refers to a human or non-human animal, generally a mammal. A subject may be a mammalian species such as a rabbit, a mouse, a rat, a guinea pig, a hamster, a dog, a cat, a pig, a cow, a goat, a sheep, a horse, a monkey, an ape or, preferably, a human. While a subject is typically a living organism, the sample may also be taken post-mortem.

The present invention also encompasses a cell comprising at least three receptor molecules R, wherein the cell has bound to at least two receptor molecules R (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and a first multimerization reagent, the first multimerization reagent comprising at least two first binding sites Z1 for the reversible binding of the first binding partner C1 of the first receptor binding reagent. The first receptor binding reagent (i) and the first multimerization reagent (ii) form a first multivalent binding complex that binds to said cell, the first multivalent binding complex comprising at least two of said first receptor binding reagents bound to one said first multimerization reagent. It is understood that the first detectable label is bound or capable of binding to said first receptor binding reagent. The cell thus has a first detectable label attached to it. Further, the cell has a second detectable label attached to it. While the first detectable label may be reversibly bound to the cell, the second detectable label may be essentially irreversibly attached to the cell. It is also understood that the first detectable label and the second detectable label are different from each other, meaning that they are not the same compound. The first multimerization reagent optionally further comprises a third detectable label. It is understood that each of the first, second, and third detectable label are preferably different from each other and can preferably be distinguished from each other. Such a cell is especially useful for determining the dissociation rate constant ($k_{off}$) of the receptor molecule R and the first receptor binding site B, which can be performed according to the methods of the invention.

As discussed, the cell has a second detectable label attached to it, wherein the second detectable label is essentially irreversibly attached to the receptor molecule R. It is understood that there are multiple possibilities for essentially irreversibly attaching such said second label to a one or more receptor molecule(s) R. The invention thus encompasses, as one possibility, that the second detectable label is attached to the cell via an irreversible multimer according to the invention. Hence, the cell may have further bound to at least two receptor molecules R (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; and wherein said second detectable label is bound to said second multivalent binding complex.

Alternatively, the cell may have attached to it a multimeric receptor binding reagent M2 according to the invention. Hence, the cell may have further bound to at least two receptor molecules R (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said cell via said at least two receptor molecules R, wherein said second detectable label is bound to said multimeric receptor binding reagent M2.

As another alternative, the cell may have attached to it an irreversible receptor binding reagent I2 according to the invention. Hence, the cell may have further bound to a receptor molecule R (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2

It is understood that the cell may be any target cell according to the invention. Likewise, the receptor molecule R may be any receptor molecule R according to the invention.

The invention further encompasses a kit suitable for conducting the methods of the invention. The kit may thus comprise (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) are capable of forming a first multivalent binding complex that is capable of binding to said target cell, wherein the first multivalent binding complex may comprise at least two of said first receptor binding reagents bound to one said first multimerization reagent, wherein a first detectable label is bound or capable of binding to said first receptor binding reagent.

The kit may further comprise (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) are capable of forming a second multivalent binding complex that is capable of binding to said target cell, the second multivalent binding complex comprising at least two of second receptor binding reagents bound to one said second multimerization reagent; wherein a second detectable label is bound to or capable of binding to said second multivalent binding complex.

Alternatively, the kit may further comprise (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 is capable of essentially irreversibly binding to said target cell via said receptor molecule R, wherein a second detectable label is bound to said multimeric receptor binding reagent M2.

Alternatively, the kit may further comprise (iii") an irreversible receptor binding reagent I2, wherein the irreversible receptor binding reagent I2 specifically binds to said receptor molecule R, wherein the irreversible receptor binding reagent I2 is capable of essentially irreversibly binding to said receptor molecule R, wherein a second detectable label is bound to said irreversible receptor binding reagent I2.

The kit may further comprise a competition reagent CR, wherein the competition reagent CR is capable of competing with first binding partner C1 for the binding to the first binding site Z1 on the first multimerization reagent. The kit may further comprise a metal chelating reagent, wherein the metal chelating reagent is preferably of EDTA or EGTA.

The invention further encompasses an apparatus. Such an apparatus comprises a first container containing a target cell comprising a receptor molecule R, and (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) are capable of forming a first multivalent binding complex that binds to said target cell, the first multivalent binding complex comprising at least two of said first receptor binding reagents bound to one said first multimerization reagent; and wherein a first detectable label is bound or capable of binding to said first receptor binding reagent; and wherein a second detectable label is essentially irreversibly attached to said receptor molecule R, wherein the first detectable label is not the second detectable label.

The apparatus further comprises a second container containing a fluid comprising a competition reagent CR, wherein the competition reagent CR is capable of competing with first binding partner C1 for the binding to the first binding site Z1 on the first multimerization reagent or a metal chelating reagent, wherein the metal chelating reagent is preferably EDTA or EGTA. The first container and a second container are connected such that a fluid can be transferred from the second container to the first container.

The first container of the apparatus may further contain (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) are capable of forming a second multivalent binding complex that binds to said target cell, the second multivalent binding complex comprising at least two of second receptor binding reagents bound to one said second multimerization reagent; and wherein said second detectable label is bound to said second multivalent binding complex.

Alternatively, the first container of the apparatus may further contain (iii') a multimeric receptor binding reagent M2, wherein the multimeric second receptor binding reagent M2 comprises at least two second receptor binding sites B2, wherein the second receptor binding site B2 specifically binds to said receptor molecule R, wherein the multimeric receptor binding reagent M2 is capable of essentially irreversibly binding to said target cell via said receptor molecule R, wherein said second detectable label is bound to said multimeric receptor binding reagent M2.

Alternatively, the first container of the apparatus may further contain (iii") an irreversible receptor binding reagent I2, wherein the irreversible receptor binding reagent I2 specifically binds to said receptor molecule R, wherein the irreversible receptor binding reagent I2 is capable of essentially irreversibly binding to said receptor molecule R, wherein said second detectable label is bound to said irreversible receptor binding reagent I2.

The apparatus may further comprise a device for controlling the temperature of the first container. Said device may comprise an isolation layer that at least partially surrounds the first container. The apparatus may further comprise a thermometer which is capable of determining the temperature within the first container. The device may further comprise a cooling element. Such a cooling element may be an air cooler. The cooling element may allow for electronic control of the temperature of or within the first container.

The first container may for example be a sample tube. Typical sample tubes may consist of plastic, such as polyethylene, polycarbonate, polystyrol or polypropylene, glass, or metal, such as steel. The tube may have a cylindrical shape and a round, flat or conical base. The volume of the first container may typically have a volume in the range of microliters to liters, typically about 0.01 mL to about 1000 mL, preferably about 0.05 mL to about 500 mL, about 0.1 mL to about 200 mL, about 0.5 mL to about 100 mL, about 1 mL to about 50 mL, about 1 mL to about 25 mL, including about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25 mL, including any number in between.

The second container may be a syringe. Any syringe can be comprised within the apparatus of the invention. It can be made of any material that is typical for a syringe, including plastic, such as polyethylene, polycarbonate, polystyrol or polypropylene, glass, or metal, such as steel, or mixtures thereof. The syringe may be suitable for manual operation or may be suitable for electronically controlled operation.

The apparatus of the invention may be comprised in an apparatus for flow cytometry. The first container of the apparatus may be connected with a sample inlet of an apparatus for flow cytometry.

The first container and the second container may be connected via a cannula or a tubing. A cannula may typically be a syringe needle and may for example be made of metal, such as copper, or (stainless) steel. A tubing may be of any material that is typically used for a tubing. It may e.g. consist of silicon, gum, pelytetrafluoroethylene (PTFE), polyvinyl chloride (PVC), copper, or (stainless) steel, just to name a few. The cannula or tubing may have an inner diameter of about 0.1 to about 20 mm, typically about 0.2 to about 10 mm, about 0.5 to about 5 mm, including about 0.5 mm, about 0.6 mm, about 0.7 mm, about 0.8 mm, about 0.9 mm, about 1 mm, about 1.2 about 1.5 mm, about 2 mm, about 3 mm, about 4 mm, or about 5 mm.

A valve may be arranged within the connection between said first container and said second container. Such a valve may preferably a three way valve. The three way valve may be connected to a third container. The third container may contain a reagent that is capable of disrupting the binding between the first binding partner C1 and the first binding site Z1 comprised in the compounds that are contained in the first container. By using a three-way valve, the second container/syringe may be loaded and unloaded without detaching or disconnecting the second container/syringe from the first container.

The invention also encompasses a method of isolating a high-avidity T cell. This method may comprise a first step, in which the dissociation rate constant ($k_{off}$) of a T cell in a sample obtained from a subject is determined according to the methods of the invention. Hereby, a high-avidity T cell may be identified. A "high-avidity T cell" may be defined by the $k_{off}$ value of the T cell receptor when binding to a given antigen. The T cell may be of "high avidity", if the $k_{off}$ value is equal or below a given threshold value. The threshold value may depend on the purpose, for which the high-avidity T cell will be isolated for. Typically, the threshold value is in the range of about $10^{-1}$ sec$^{-1}$ to about $10^{-3}$ sec$^{-1}$, preferably, the threshold value may be in the range of about $5\times10^{-2}$ sec$^{-1}$ to about $2\times10^{-3}$ sec$^{-1}$, preferably about $2\times10^{-2}$ sec$^{-1}$ to about $5\times10^{-3}$ sec$^{-1}$, preferably about $1\times10^{-2}$ sec$^{-1}$.

The method may then comprise a further step of isolating said T cell or population of T cells from a sample obtained from the same subject. Isolation of said T cell (population) can be performed by any method know in the art, for example by using a reversible cell staining/isolation technology as described patent in U.S. Pat. Nos. 7,776,562, 8,298,782, International Patent application WO02/054065 or International Patent Application WO2013/011011. The sample, out of which the T cell (population) is isolated in the second step may be the same sample as in the first step or may be another sample obtained from the same subject.

The present invention is further characterized by the following items

Item 1. A method of determining the dissociation rate constant ($k_{off}$) of a receptor molecule R on a target cell and a first receptor binding site B1, comprising detecting a first detectable label attached to the target cell and a second detectable label attached to the target cell, wherein the cell has been contacted with (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; and wherein said first detectable label is bound or capable of binding to said first receptor binding reagent; and wherein said second detectable label is essentially irreversibly attached to said receptor molecule R, wherein the first detectable label and the second detectable label are different from each other.

Item 2. The method of item 1, wherein the cell has further been contacted with (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; and wherein said second detectable label is bound to said second multivalent binding complex.

Item 3. The method of item 1, wherein the cell has further been contacted with (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein said second detectable label is bound to said multimeric receptor binding reagent M2.

Item 4. The method of item 1, wherein the cell has further been contacted with (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2.

Item 5. The method of any one of the preceding items, wherein said receptor molecule R is a T cell receptor (TCR).

Item 6. The method of any one of the preceding items, wherein said first receptor binding site B1 is a MHC molecule.

Item 7. The method of any one of the preceding items, wherein (a) said first binding partner C1 comprises a streptavidin or avidin binding peptide and said first multimerization reagent comprises streptavidin, or avidin, or a streptavidin analog, or an avidin analog that reversibly binds to said streptavidin or avidin binding peptide; or (b) said first binding partner C1 comprises a biotin analog that reversibly binds to streptavidin or avidin and said first multimerisation reagent comprises streptavidin, or avidin, or a streptavidin analog, or an avidin analog that reversibly binds to said biotin analog.

Item 8. The method of item 7, wherein said first binding partner C1 comprises the streptavidin-binding peptide Trp-Ser-His-Pro-Gln-Phe-Glu-Lys (SEQ ID NO: 01) and said multimerization reagent comprises the streptavidin analog Val$^{44}$-Thr$^{45}$-Ala$^{46}$-Arg$^{47}$ (SEQ ID NO: 02) or the streptavidin analog Ile$^{44}$-Gly$^{45}$-Ala$^{46}$-Arg$^{47}$ (SEQ ID NO: 03).

Item 9. The method of any one of items 1 to 6, wherein the binding between said first binding partner C1 and said first binding site Z1 of said first multimerization reagent occurs in the presence of a divalent cation.

Item 10. The method of item 9, wherein a. said first binding partner C1 comprises a calmodulin binding peptide and the said first multimerization reagent comprises calmodulin, or b. said first binding partner C1 comprises an oligohistidine tag and said first multimerization reagent comprises a metal ion bound to a metal chelating agent.

Item 11. The method of any one of items 1 to 6, wherein said first binding partner C1 comprises an antigen and said first multimerization reagent comprises an antibody against said antigen.

Item 12. The method of item 11, wherein the antigen is an epitope tag.

Item 13. The method of item 18, where the epitope tag is selected from the group consisting of FLAG-tag (sequence: DYKDDDDK, SEQ ID NO: 04), Myc-tag (sequence: EQKLISEEDL, SEQ ID NO: 05), HA-tag (sequence: YPYDVPDYA, SEQ ID NO: 06), VSV-G-tag (sequence: YTDIEMNRLGK, SEQ ID NO: 07), HSV-tag (sequence: QPELAPEDPED, SEQ ID NO: 08), and V5-tag (sequence: GKPIPNPLLGLDST, SEQ ID NO: 09).

Item 14. The method of item 11, wherein said antigen comprises a protein.

Item 15. The method of item 14, wherein the protein is selected from the group of the maltose binding protein (MBP), chitin binding protein (CBP) and thioredoxin.

Item 16. The method of any one of items 1 to 6, wherein said first binding partner C1 comprises glutathione S-transferase and said first multimerization reagent comprises glutathione or wherein said first binding partner C1 comprises a glutathione and said first multimerization reagent comprises glutathione S-transferase.

Item 17. The method of any one of items 1 to 6, wherein said first binding partner C1 comprises an immunoglobulin Fc portion and said first multimerization reagent comprises a protein selected from the group consisting of protein A, protein G, protein a/g, and protein L, or wherein said first binding partner C1 comprises a protein selected from the group consisting of protein A, protein G, protein a/g, and protein L and said first multimerization reagent comprises an immunoglobulin Fc portion.

Item 18. The method of any one of items 2, 3 and 5 to 17, wherein the second receptor binding site B2 is a MHC molecule.

Item 19. The method of any one of items 2, 3 and 5 to 18, wherein the first receptor binding site B1 and the second receptor binding site B2 are the same.

Item 20. The method of any one of items 2 to 17, wherein the second receptor binding site B2 or irreversible receptor binding reagent I2 is selected from the group consisting of an antibody, an divalent antibody fragment, a monovalent antibody fragment, and a proteinaceous binding molecule with antibody-like binding.

Item 21. The method of item 20, wherein the divalent antibody fragment is an (Fab)$_2$'-fragment, or a divalent single-chain Fv fragment.

Item 22. The method of item 20, wherein the monovalent antibody fragment is selected from the group consisting of a Fab fragment, an Fv fragment, and a single-chain Fv fragment (scFv).

Item 23. The method of item 20, wherein the proteinaceous binding molecule with antibody-like binding properties is selected from the group of an aptamer, a mutein based on a polypeptide of the lipocalin family, a glubody, a protein based on the ankyrin scaffold, a protein based on the crystalline scaffold, an adnectin, and an avimer.

Item 24. The method of any one of items 2 and 5 to 23, wherein said second binding partner C2 comprises biotin or a biotin analog and said second multimerization reagent comprises a streptavidin analog or an avidin analog that essentially irreversibly binds to biotin or said biotin analog.

Item 25. The method of any one of the preceding items, wherein said target cell is a mammalian cell.

Item 26. The method of item 24, wherein said mammalian cell is a lymphocyte or a stem cell.

Item 27. The method of item 25, wherein the lymphocyte is a T cell, a T-helper cell, a B cell or a natural killer cell.

Item 28. The method of item 26, wherein the T-cell is selected from the group of a CMV-specific CD8+ T-lymphocyte, a cytotoxic T-cell a, memory T-cell and a regulatory T-cell.

Item 29. The method of any one of the preceding items, wherein the first detectable label is a fluorescent dye.

Item 30. The method of any one of the preceding items, wherein the second detectable label is a fluorescent dye.

Item 31. The method of any one of the preceding items, wherein each of the first detectable label is a first fluorescent dye and the second detectable label is a second fluorescent dye, wherein the emission signal of the first fluorescent dye can preferably be distinguished from the emission signal of the second fluorescent dye.

Item 32. The method any one of items 2 to 31, comprising (a) contacting said target cell comprising said receptor molecule R with (i) said first receptor binding reagent and (ii) said first multimerization reagent and (b) contacting said target cell with (iii) said second receptor binding reagent and (iv) said second multimerization reagent, or contacting said target cell with (iii') said multimeric receptor binding reagent; or contacting said target cell with (iii") said irreversible receptor binding reagent.

Item 33. The method item 32, wherein (a) is performed prior to (b).

Item 34. The method of item 33, further comprising after (a) and prior to (b) a washing step.

Item 35. The method of any one of items 32 to 34, further comprising (c) disrupting the binding between (i) the first receptor binding reagent and (ii) the first multimerization reagent.

Item 36. The method of item 35, wherein the binding between (i) the first receptor binding reagent and (ii) the first multimerization reagent is disrupted by contacting (i) and (ii) with a competition reagent CR, wherein the competition reagent CR is capable of competing with first binding partner C1 for the binding to the first binding site Z1 on the first multimerization reagent.

Item 37. The method of item 36, wherein the first binding partner C1 is a streptavidin binding peptide and the competition reagent CR is biotin or a biotin analog.

Item 38. The method of item 36 or 37, wherein the first multimerization reagent comprises a streptavidin or a streptavidin analog.

Item 39. The method of item 35, wherein the binding between (i) the first receptor binding reagent and (ii) the first multimerization reagent is disrupted by metal ion chelation.

Item 40. The method of item 39, wherein the metal chelation is accomplished by addition of EDTA or EGTA.

Item 41. The method of item 35, wherein the binding between (i) the first receptor binding reagent and (ii) the first multimerization reagent is disrupted by pH shift.

Item 42. The method of any one of items 32 to 41, further comprising (d) detecting the first detectable label attached to the target cell and detecting the second detectable label attached to the target cell.

Item 43. The method of item 42, wherein the first detectable label is a first fluorescent dye and the second detectable label is a second fluorescent dye, wherein the emission signal of the first fluorescent dye can preferably be distinguished from the emission signal of the second fluorescent dye.

Item 44. The method of item 43, wherein the detection of the first detectable label and the second detectable label is by flow cytometry.

Item 45. The method of item 44, wherein the detection of second detectable signal is indicative for the presence of the receptor molecule R on the target cell.

Item 46. The method of item 45, wherein the detection of the first detectable label on a cell on which the second detectable signal is detected is indicative for the non-dissociation of the of the first receptor binding site B1 from the receptor molecule R at the time of detecting the first detectable label.

Item 47. The method of item 45, wherein the non-detection of the first detectable label on a cell on which the second detectable signal is detected is indicative for the dissociation of the of the first receptor binding site B1 from the receptor molecule R at the time of detecting the first detectable label.

Item 48. The method of any one of items 45 to 47, wherein the reduction of detection events of the first detectable label on a cell on which the second detectable signal is detected is indicative for the kinetic of dissociation of the first receptor binding site B1 from the receptor molecule R.

Item 49. The method of any one of the preceding items, wherein the dissociation rate constant ($k_{off}$) for the reversible binding between said binding site Z1 and said partner C1 is in the range of $0.5 \times 10^{-4}$ sec$^{-1}$ or greater.

Item 50. The method of any one of items 2, and 5 to 48, wherein the dissociation rate constant ($k_{off}$) for the binding between said binding site Z2 and said partner C2 is in the range of $1 \times 10^{-5}$ sec$^{-1}$ or less.

Item 51. The method of any one of items 3 and 5 to 48, wherein the dissociation rate constant ($k_{off}$) for the essentially irreversible binding between said multimeric receptor binding reagent M2 and said target cell is in the range of $1 \times 10^{-5}$ sec$^{-1}$ or less.

Item 52. The method of any one of items 4 to 48, wherein the wherein the dissociation rate constant ($k_{off}$) for the essentially irreversible binding between said irreversible receptor binding reagent I2 and said receptor molecule R is in the range of $1 \times 10^{-5}$ sec$^{-1}$ or less.

Item 53. The method of any one of the preceding items, wherein the dissociation rate constant ($k_{off}$) of a receptor molecule R on a target cell and a first receptor binding site B1 is suspected to be in a range of $10^0$ sec$^{-1}$ to $10^{-4}$ sec$^{-1}$.

Item 54. The method of any one of the preceding items, wherein contacting the cell with the first receptor binding reagent is carried out at a temperature of ≤15° C.

Item 55. The method of item 54, wherein said contacting is carried out at a temperature of ≤4° C.

Item 56. A cell comprising at least three receptor molecules R, wherein the cell has bound to at least two receptor molecules R (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; and wherein a first detectable label is bound to said first receptor binding reagent; and wherein a second detectable label is essentially irreversibly attached to at least one receptor molecule R.

Item 57. The cell of item 56, wherein the cell has further bound to at least two receptor molecules R (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; and wherein said second detectable label is bound to said second multivalent binding complex.

Item 58. The cell of item 56, wherein the cell has further bound to at least two receptor molecules R (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said cell via said at least two receptor molecules R, wherein said second detectable label is bound to said multimeric receptor binding reagent M2.

Item 59. The cell of item 56, wherein the cell has further bound to a receptor molecule R (iii'') an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2.

Item 60. The cell of any one of items 56 to 59, wherein said target cell is a mammalian cell.

Item 61. The cell of item 60, wherein said mammalian cell is a lymphocyte or a stem cell.

Item 62. The cell of item 61, wherein the lymphocyte is a T cell, a T-helper cell, a B cell or a natural killer cell.

Item 63. The cell of item 62, wherein the T-cell is selected from the group of a CMV-specific CD8+ T-lymphocyte, a cytotoxic T-cell a, memory T-cell and a regulatory T-cell.

Item 64. The cell of any one of items 56 to 63, wherein said receptor molecule R is a T cell receptor (TCR).

Item 65. A reagent kit for determining the dissociation rate constant ($k_{off}$) of a receptor molecule R on a target cell and a first receptor binding site B1, wherein the kit comprises (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) form a first multivalent binding complex that binds to said target cell, the first multivalent binding complex comprising at least two of said first receptor binding reagents bound to one said first multimerization reagent; wherein said first detectable label is bound or capable of binding to said first receptor binding reagent; and (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent; and (iv) a second multimerization reagent, the second multimerization reagent comprising at least two second binding sites Z2 for the stable binding of the second binding partner C2 of the second receptor binding reagent; wherein the second receptor binding reagent (iii) and the second multimerization reagent (iv) form a second multivalent binding complex that binds to said target cell, the second multivalent binding complex comprising at least two of second receptor binding reagents bound to one said second multimerization reagent; wherein a second detectable label is bound to said second multivalent binding complex; or (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein a second detectable label is bound to said multimeric receptor binding reagent M2; or (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein a second detectable label is bound to said irreversible receptor binding reagent I2; wherein the first detectable label is not the second detectable label.

Item 66. The kit of item 65, further comprising a competition reagent CR, wherein the competition reagent CR is capable of competing with first binding partner C1 for the binding to the first binding site Z1 on the first multimerization reagent.

Item 67. The kit of item 65, further comprising a metal chelating reagent, wherein the metal chelating reagent is preferably of EDTA or EGTA.

Item 68. An apparatus comprising a first container containing a target cell comprising a receptor molecule R, and (i) a first receptor binding reagent, the first receptor binding reagent comprising at least one first receptor binding site B1, wherein the first receptor binding site B1 specifically binds to said receptor molecule R, the first receptor binding reagent further comprising at least one first binding partner C1, wherein the first binding partner C1 is capable of being reversibly bound to a first binding site Z1 of a first multimerization reagent, and (ii) a first multimerization reagent, the first multimerization reagent comprising at least two first binding sites Z1 for the reversible binding of the first binding partner C1 of the first receptor binding reagent, wherein the first receptor binding reagent (i) and the first multimerization reagent (ii) are capable of forming a first multivalent binding complex that binds to said target cell, the first multivalent binding complex comprising at least two of said first receptor binding reagents bound to one said first multimerization reagent; and wherein a first detectable label is bound or capable of binding to said first receptor binding reagent; and wherein a second detectable label is essentially irreversibly attached to said receptor molecule R, wherein the first detectable label is not the second detectable label; and a second container containing a fluid comprising a) a competition reagent CR, wherein the competition reagent CR is capable of competing with first binding partner C1 for the binding to the first binding site Z1 on the first multimerization reagent; or b) a metal chelating reagent, wherein the metal chelating reagent is preferably EDTA or EGTA, wherein the first container and a second container are connected such that a fluid can be transferred from the second container to the first container.

Item 69. The apparatus of item 68, wherein the first container further contains (iii) a second receptor binding reagent, the second receptor binding reagent comprising at least one second receptor binding site B2, wherein the second receptor binding site B2 specifically binds to said receptor molecule R, the second receptor binding reagent further comprising at least one second binding partner C2, wherein the second binding partner C2 is capable of being stably bound to a second binding site Z2 of a second multimerization reagent, and (iv) a second multimerization reagent, the second multimerization reagent comprising at least two second binding sites Z2 for the stable binding of the second binding partner C2 of the second receptor binding reagent, wherein the second receptor binding reagent (iii) and the second multimerization reagent (iv) are capable of forming a second multivalent binding complex that binds to said target cell, the second multivalent binding complex comprising at least two of second receptor binding reagents bound to one said second multimerization reagent; and wherein said second detectable label is bound to said second multivalent binding complex.

Item 70. The apparatus of item 68, wherein the first container further contains (iii') a multimeric receptor binding reagent M2, the multimeric second receptor binding reagent comprising at least two second receptor binding sites B2, wherein the second receptor binding site B2 specifically binds to said receptor molecule R, wherein the multimeric receptor binding reagent M2 essentially irreversibly binds to said target cell via said receptor molecule R, wherein said second detectable label is bound to said multimeric receptor binding reagent M2.

Item 71. The apparatus of item 68, wherein the first container further contains (iii") an irreversible receptor binding reagent I2, wherein the irreversible receptor binding reagent I2 specifically binds to said receptor molecule R, wherein the irreversible receptor binding reagent I2 essentially irreversibly binds to said receptor molecule R, wherein said second detectable label is bound to said irreversible receptor binding reagent I2.

Item 72. The apparatus of any one of items 68 to 71 being comprised in an apparatus for flow cytometry.

Item 73. The apparatus of any one of items 68 to 72, wherein the first container is connected to the sample inlet of an apparatus for flow cytometry.

Item 74. The apparatus of any one of items 68 to 73, wherein said first container and said second container are connected via a cannula or a tubing.

Item 75. The apparatus of any one of items 68 to 74, comprising a valve arranged within the connection between said first container and said second container.

Item 76. The apparatus of item 75, wherein the valve is a three-way valve.

Item 77. A method of isolating a high-avidity T cell comprising a) determining the dissociation rate constant ($k_{off}$) of a T cell in a sample obtained from a subject using the method according to any one of items 1 to 56.b) isolating said T cell from a sample obtained from said subject.

Item 78. The method of item 77, wherein the determined dissociation rate constant has a value that is equal or below a given threshold value.

Item 79. The method of item 77, wherein the threshold value is in the range of about $10^{-1}$ $sec^{-1}$ to about $10^{-3}$ $sec^{-3}$.

Item 80. The method of any one of items 77 to 79, wherein the sample is a peripheral blood sample or a PBMC sample.

Item 81. The method of any one of items 77 to 80, wherein the subject is a mammal, preferably a human.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.) are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

EXAMPLES

Cells

Human CMV-specific T cell clones and murine T cell lines were generated as described in Nauerth M, Weißbrich B, Knall R, Franz T, Dössinger G, Bet J, Paszkiewicz P J, Pfeifer L, Bunse M, Uckert W and others. TCR-ligand $k_{off}$ rate correlates with the protective capacity of antigen-specific CD8+ T cells for adoptive transfer. Sci Transl Med 2013; 5:192ra87-192ra87. Peripheral blood was obtained from a healthy adult donor (male). Written informed consent was obtained from the donor, and usage of the blood samples was approved according to national law by the local Institutional Review Board (Ethikkommission der Medizinischen Fakultät der Technischen Universität München) in accordance with the Declaration of Helsinki. Whole blood was diluted 1:1 with PBS (pH 7.4) and PBMCs were obtained by density gradient centrifugation for 20 min at 2000 rpm on a layer of Ficoll.

Multimer and Antibody Staining pMHC molecules for generation of reversible multimers carrying a Twin-Strep-Tag were refolded and multimerized as described in Nauerth et al 2013. All pMHC molecules used for the $k_{off}$-rate assays in this report were conjugated to Alexa488 maleimide fluorophore (Thermo Fisher) and multimerized Streptactin APC (IBA). Biotinylated pMHC molecules for the generation of non-reversible multimers were refolded according to the protocol described in Busch D H, Pilip I M, Vijh S, Pamer E G. Coordinate regulation of complex T cell populations responding to bacterial infection. Immunity 1998; 8:353-62. For multimerization, 1 μg biotinylated pMHC molecules were incubated with 1.25 μg Streptavidin BV421 or Streptavidin PE (Biolegend) in a total volume of 50 μl for 45 min. For the $k_{off}$-rate assay, up to 5*10⁶ cells were incubated for 45 min with the reversible multimers. If indicated, CD8 antibodies (CD8 eF450, eBioscience or CD8 PeCy7, Beckman Coulter) were added after 25 min and incubated for additional 20 min. For live/dead discrimination, 0.2 μg propidium iodide solution was added and incubated for 5 min. Cell were subsequently washed and either used directly for the $k_{off}$-rate assay or additionally stained with for 10 min (unless otherwise indicated) with the nonreversible multimer. For titration of the non-reversible multimer, cells were either stained with 50 μl of the non-reversible multimer (1:1), with 25 μl diluted with 25 μl FACS buffer (1:2) or with 12.5 μl of the non-reversible multimer diluted with 37.5 μl FACS buffer (1:4).

FACS Analysis and Sorting

Samples were analyzed using a CyanLx 9 color flow cytometer (Beckman Coulter). For the $k_{off}$-rate assay, computed parameters of the analyzed samples were saved to enable analysis of dissociation kinetics. Cell sorting was performed on a MoFlo (Beckman Coulter). FACS data was analyzed with FlowJo v9.5.2 software (Tree Star, Inc.).

Flow Cytometry Based $k_{off}$-Rate Assay

For the performance of the $k_{off}$-rate assay, cells were diluted to 1*10⁶-1*10⁷ cells/ml and 100 μl of the cells were added to precooled $k_{off}$-rate FACS tubes containing 900 μl FACS buffer. The $k_{off}$-rate FACS tube was mounted together with the cooling device (qutools) on the flow cytometer and analysis was initiated. After 30 s, 1 ml 2 mM D-biotin was added over the three-way valve to the cells during ongoing analysis. Cells were analyzed for a total of 15 min. For analysis of the $k_{off}$-rate, fluorescence data of specific T cells were exported from FlowJo into a spreadsheet program (GraphPad Software, San Diego, Calif., USA). Data points for analysis of the $k_{off}$-rate were selected as described in the text and an one-phase exponential decay curve fitted into the data points.

Microscopic $k_{off}$-Rate Assay

Performed as described in detail in Nauerth et al. 2013.

Figure 1:
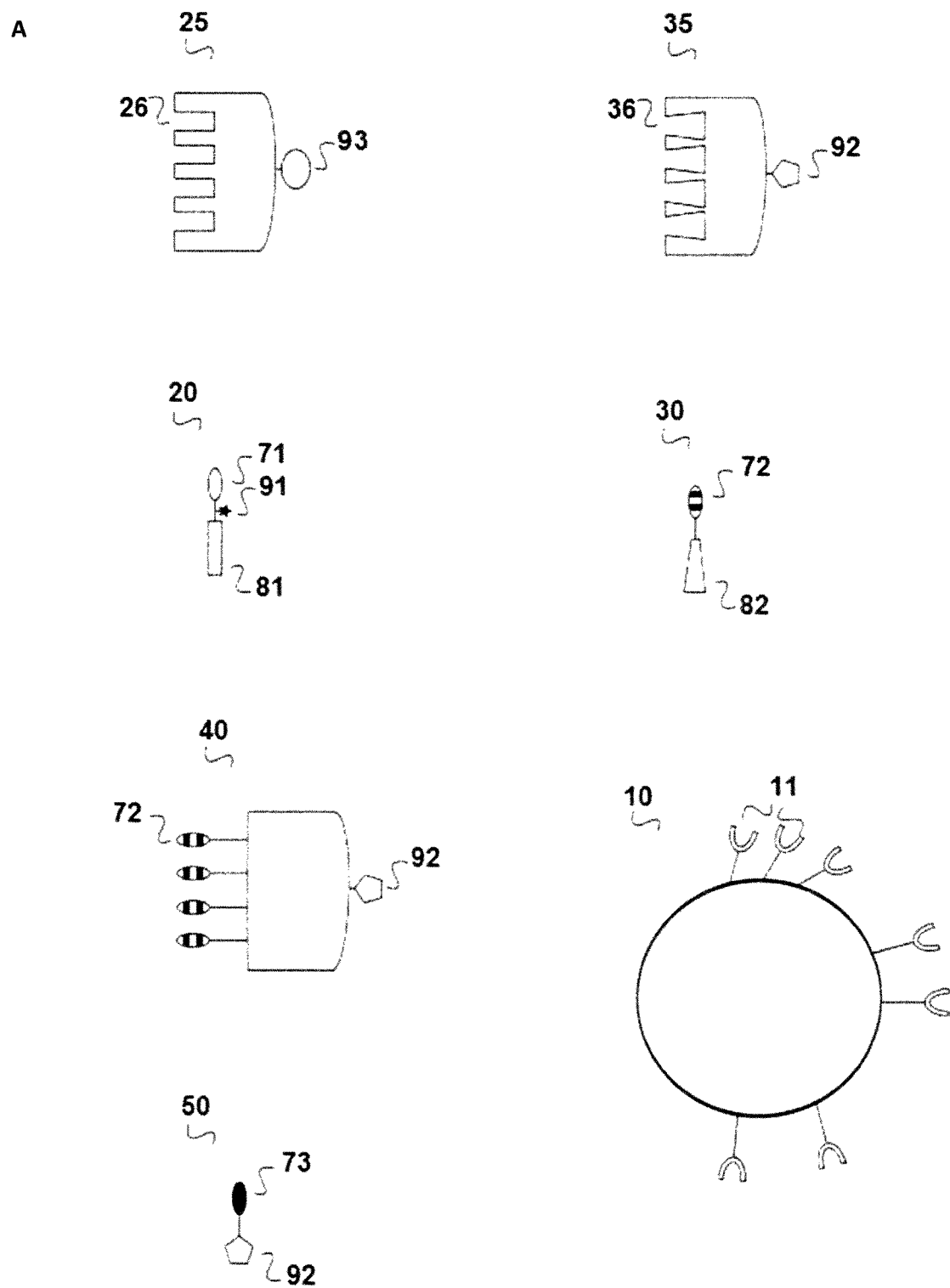
FIG. 1
Figure 1:
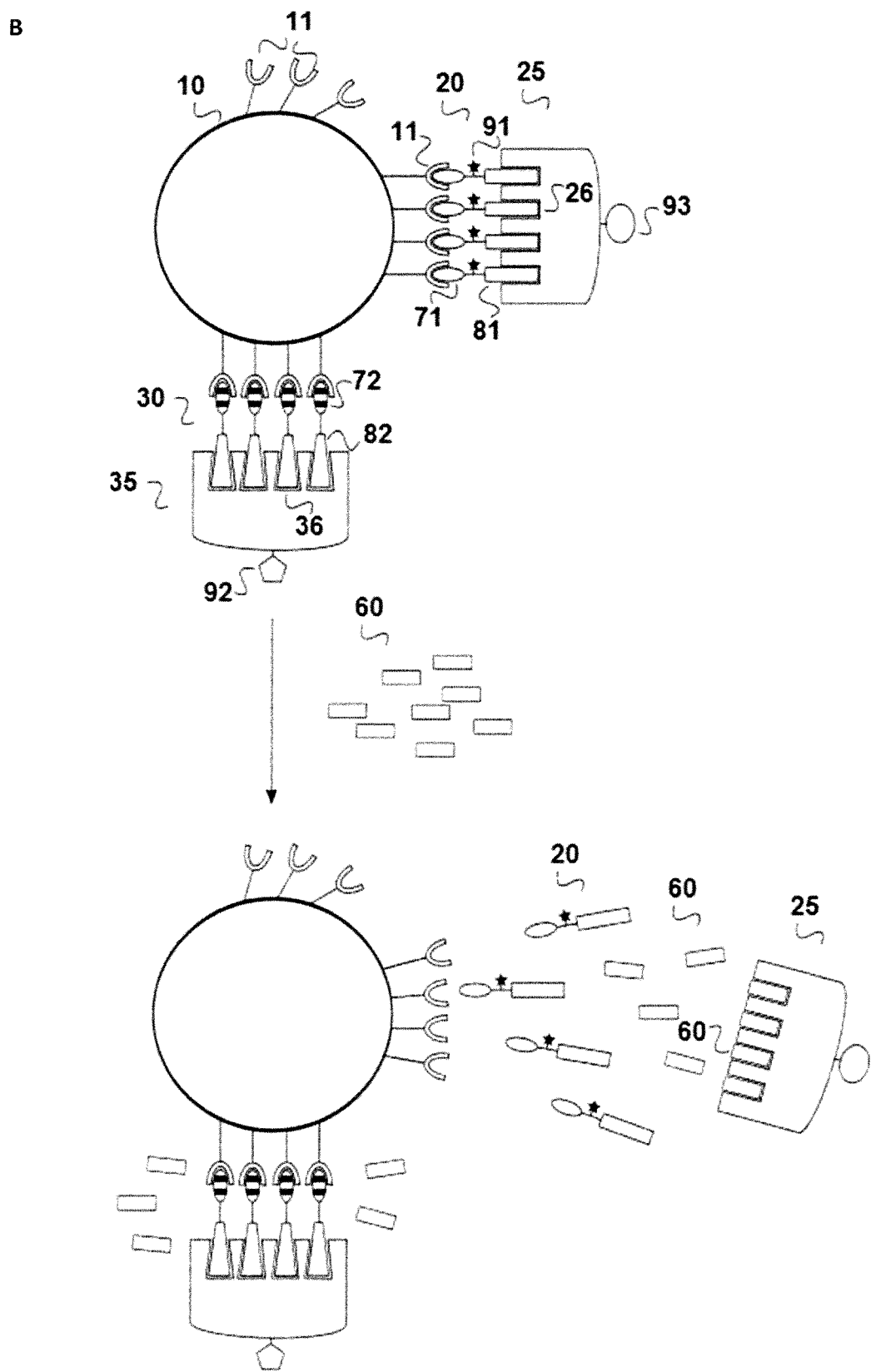
Figure 1:
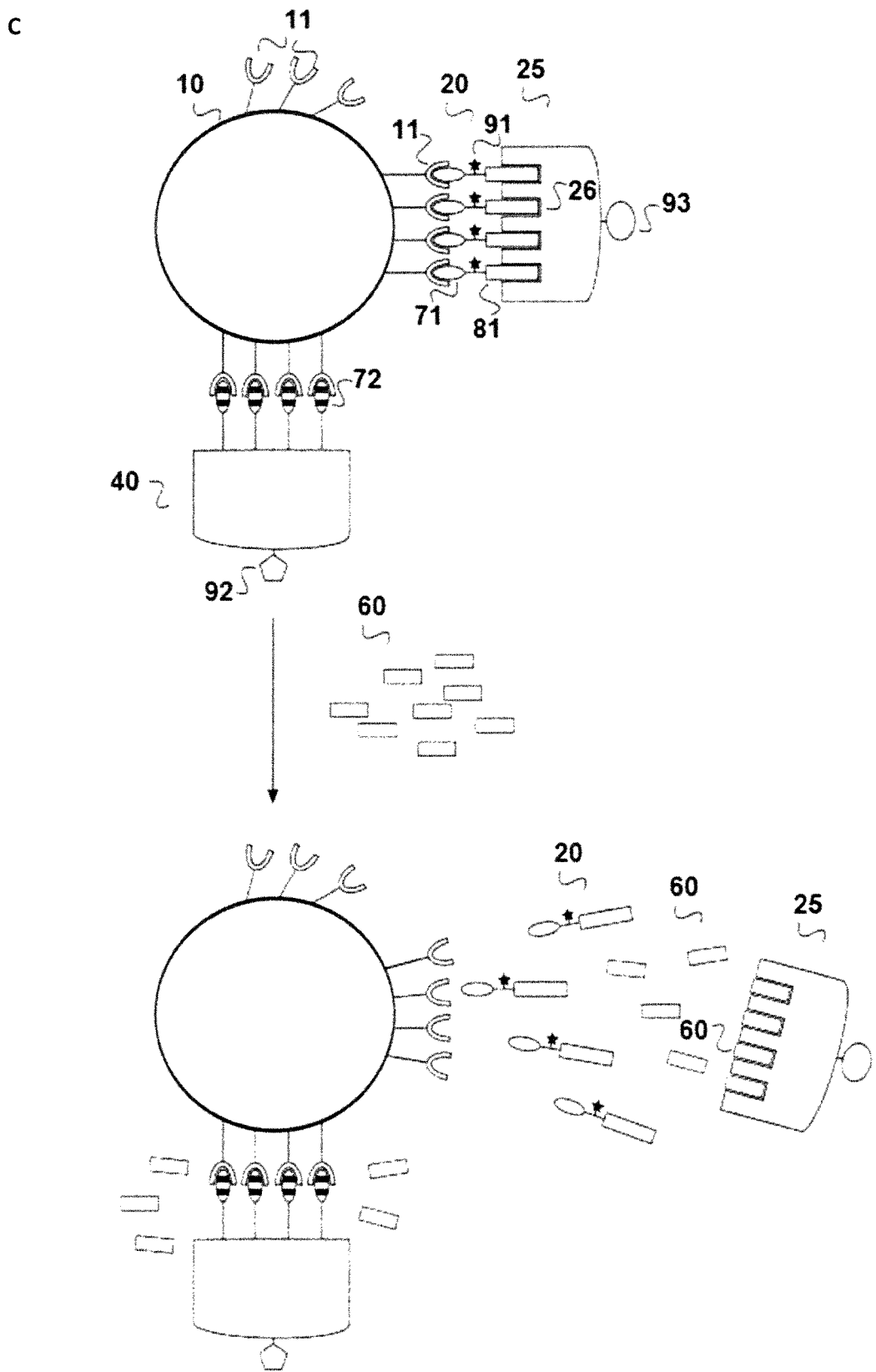
Figure 1:
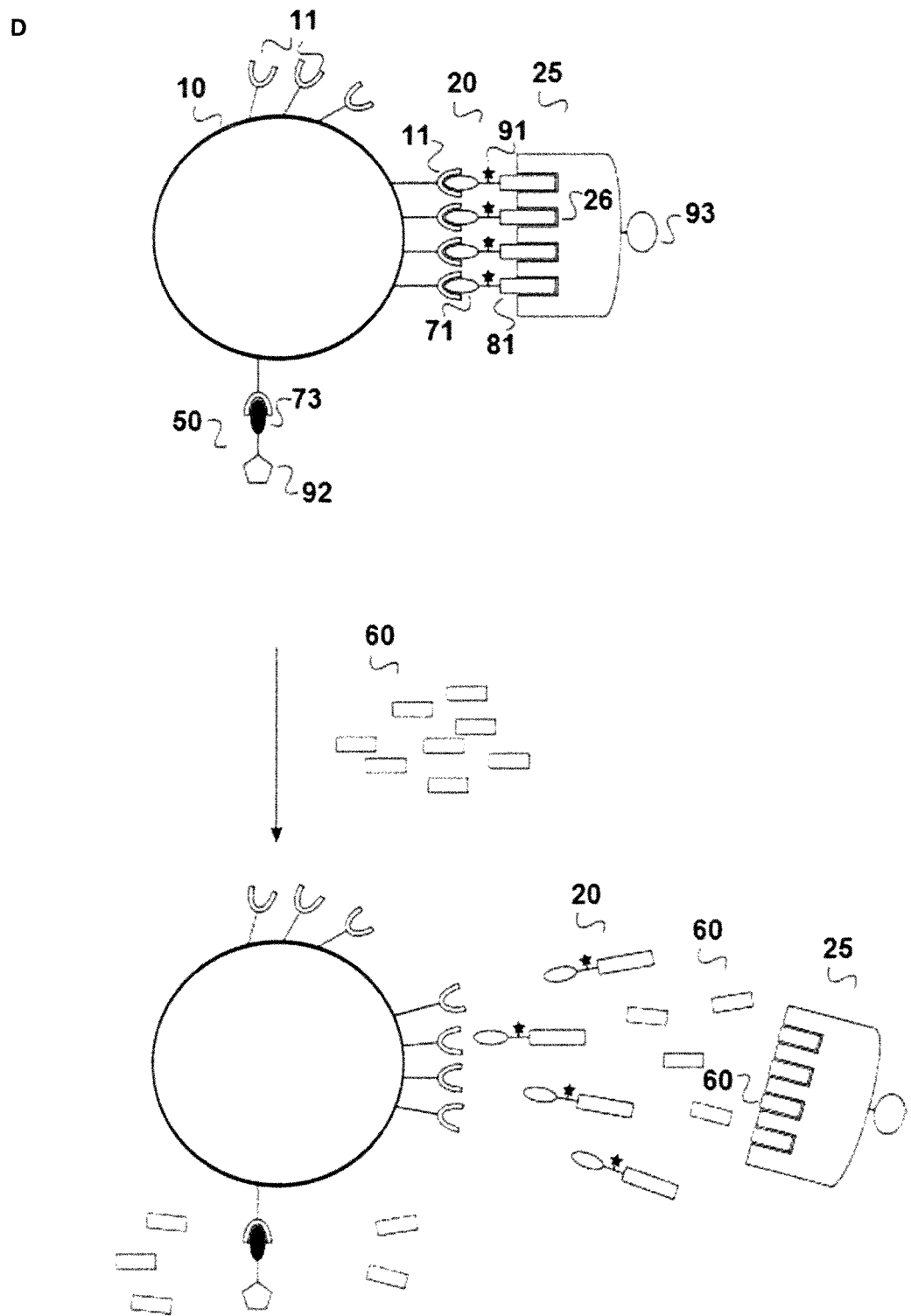
Figure 2:
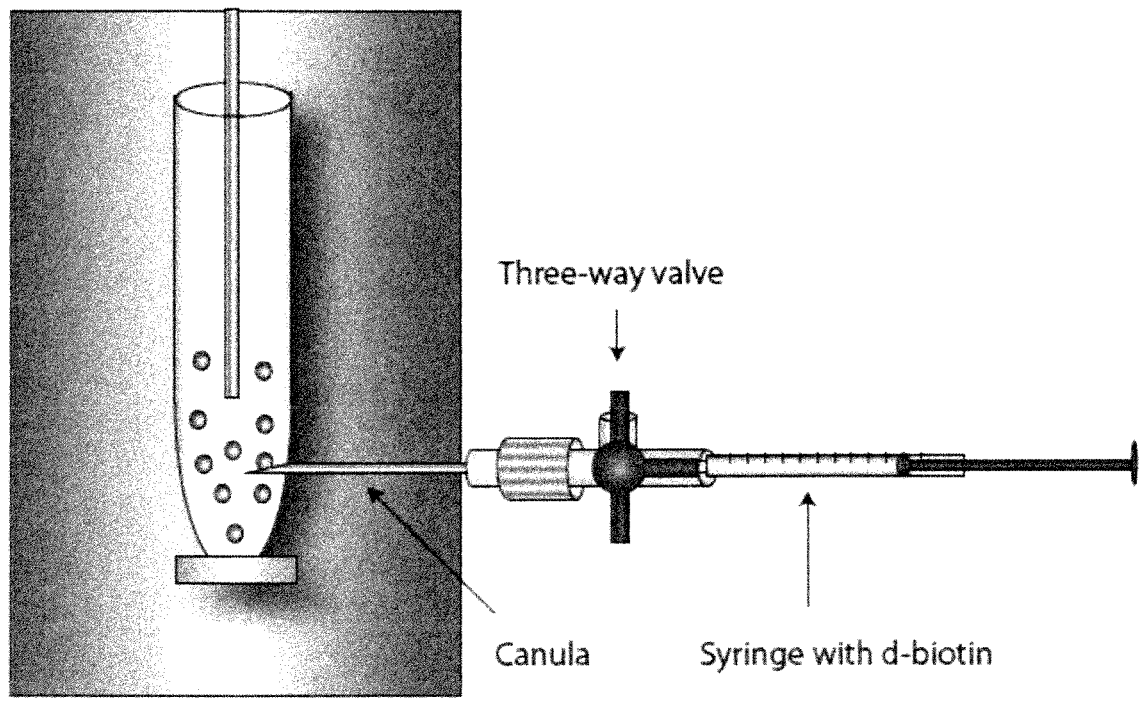
FIG. 2: Setup and Analysis of the Flow Cytometry Based $k_{off}$-Rate Assay
Figure 2:
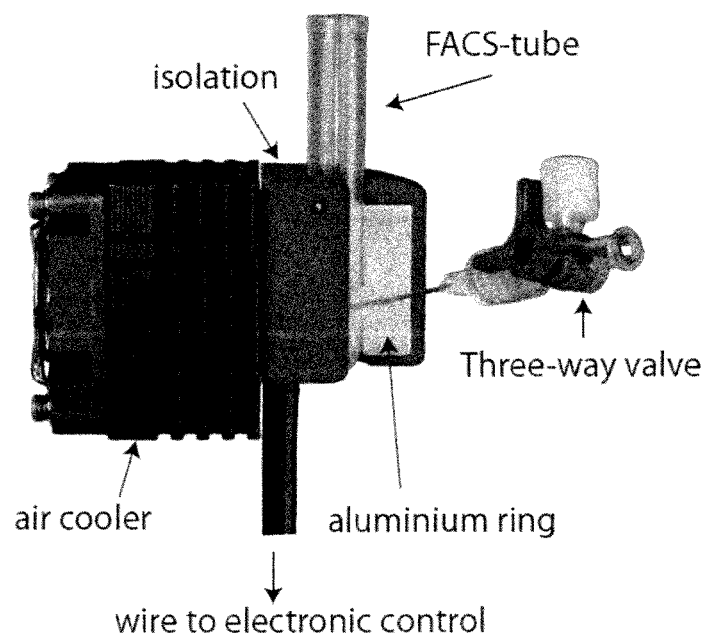
Figure 2:
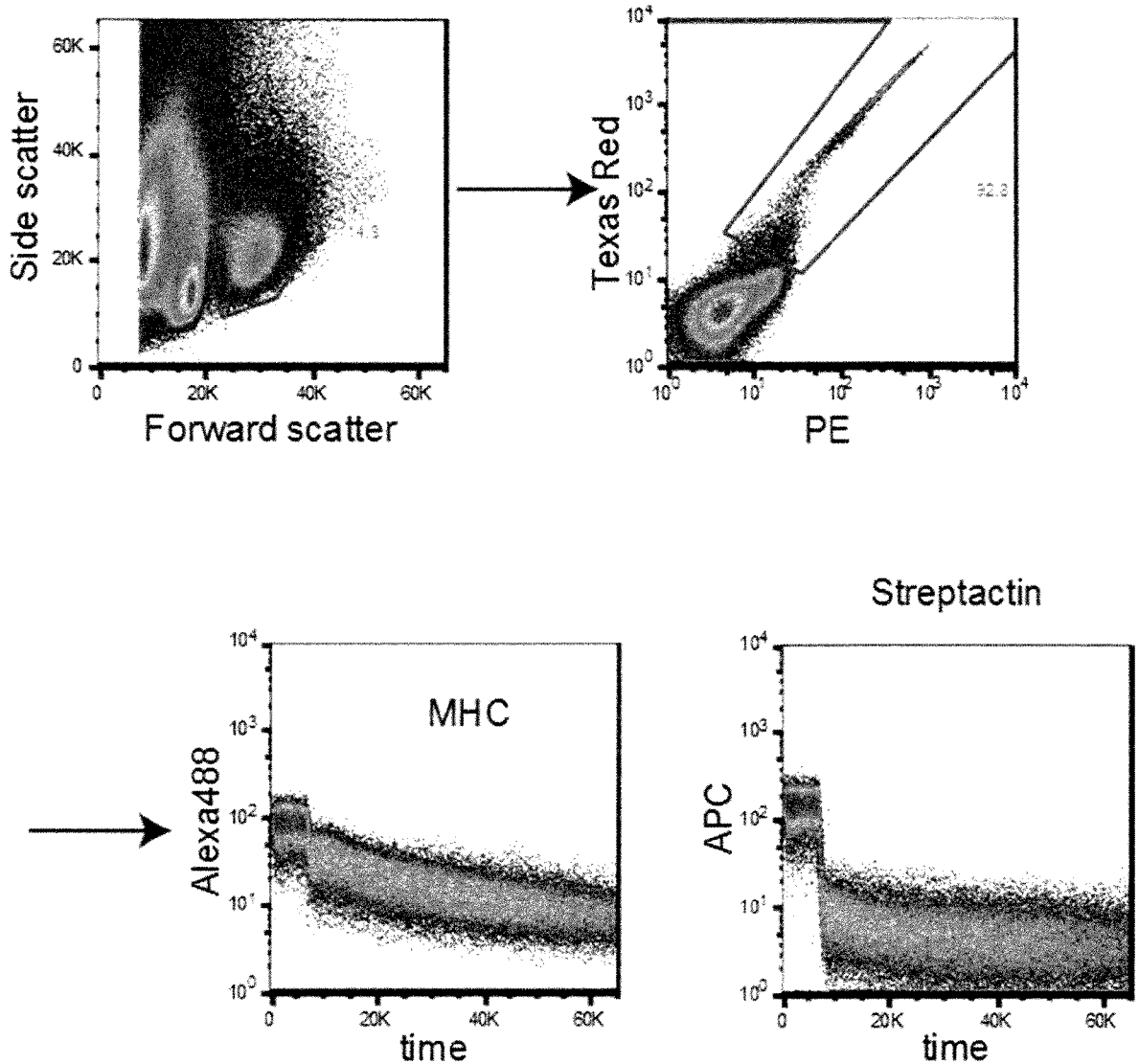
Figure 2:
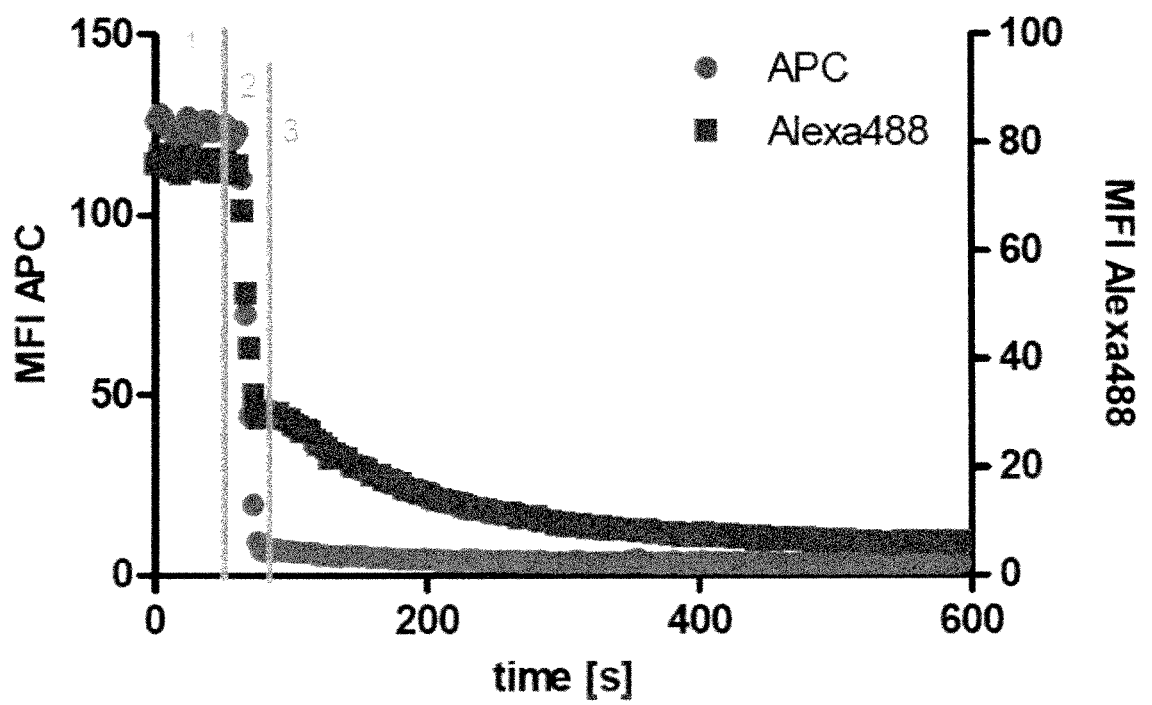
Figure 2:
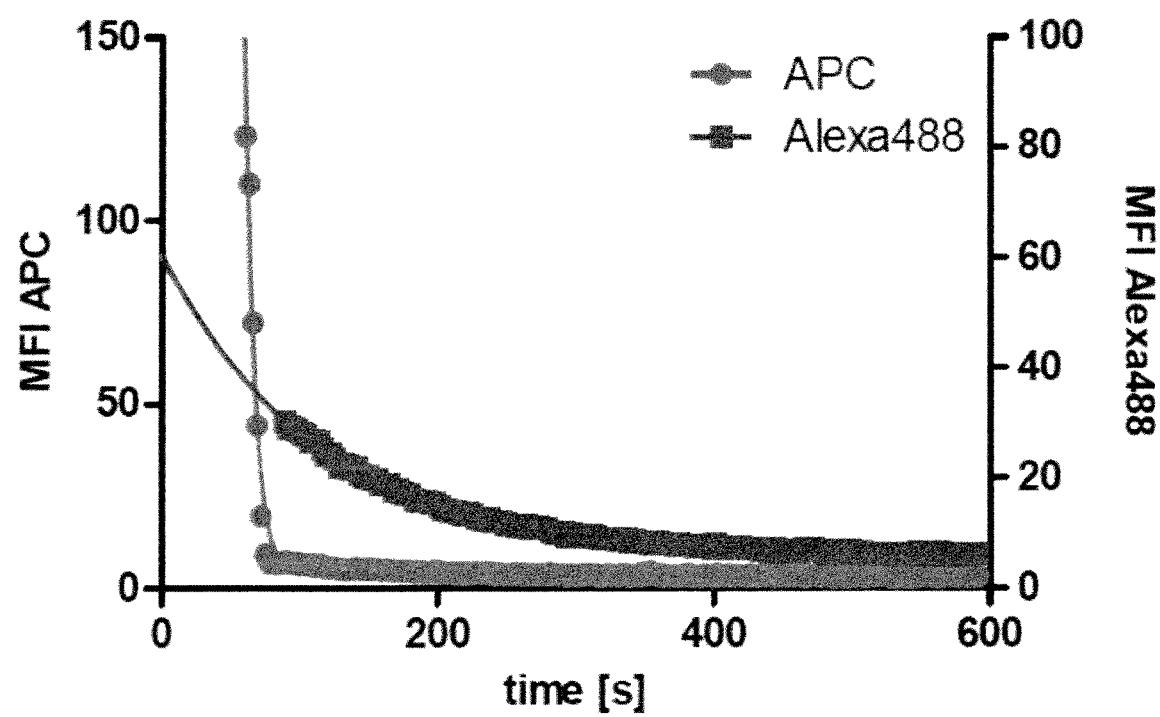
Figure 2:
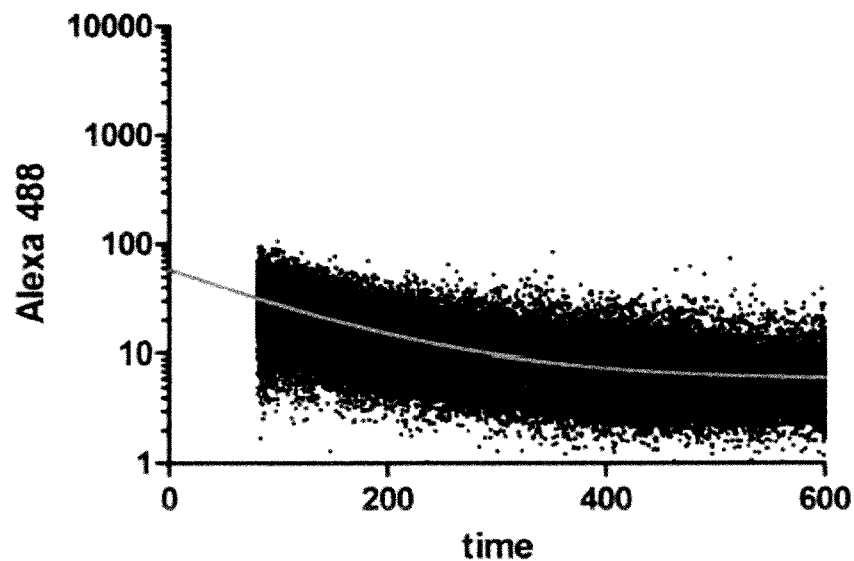
Figure 2:
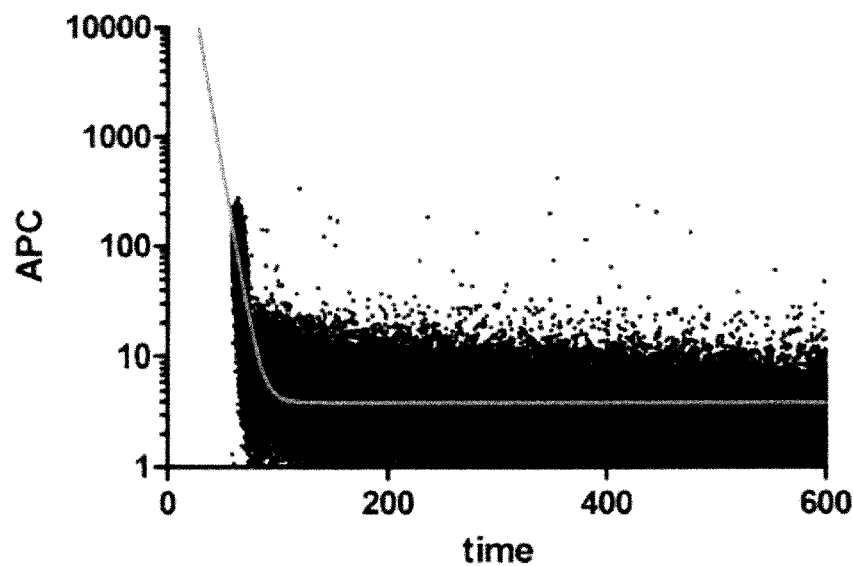

Example 1: Setup and Analysis of the Flow Cytometry-Based TCR-Ligand $k_{off}$-Rate Assay In order to transfer the principle of the TRC-ligand $k_{off}$-rate assay to flow cytometry, the basic components for data analysis need to be acquired in analogy to the original microscopy-based application: first, the initial pMHC/Streptactin multimer staining has to be determined; then, D-biotin needs to be added to the sample and subsequently the dissociation of the Streptactin backbone and the pMHCs has to be followed until a minimum level of ligand binding is reached. Since the inventors knew already from the microscopy-based assay that for some T cell receptors $k_{off}$-rate kinetics can be quite fast, they designed an experimental setup for flow cytometry where d-biotin can be added to the probe without interrupting the online measurement. For this purpose, the inventors penetrated standard polyethylene FACS tubes with a sharp injection needle that was connected via a three-way valve to a syringe containing D-biotin solution (FIG. 2A). This setting allows to acquire initial staining values (usually 30 seconds) followed by D-biotin injection and subsequent acquisition of the dissociation phase (usually 15 min) without the need to take the probe out of the sample holder at any time-point.

$K_{off}$-rate assays are preferably to be performed at defined temperatures in order to obtain reproducible results that can be compared between different samples. For TCR-ligand interactions, the assay was performed at low temperatures (preferably at 4° C.). For this purpose, the inventors designed a peltier-controlled cooling device tightly surrounding the sample tube while still leaving a small opening for the D-biotin injection system (FIG. 2B).

With this experimental setup, the inventors next acquired a full $k_{off}$-rate sequence using a T cell line expressing the 2C TCR. The inventors stained the cells with reversible MHC multimers based on Alexa488-labeled pMHC (H2Kb-SIYRYYGL (SEQ ID NO: 10)) and APC-conjugated Streptactin as backbone. Additional PI staining was performed to identify dead cells. Data analysis of the dissociation was performed by gating on the population of interest (in this case living lymphocytes) and subsequent display of the Streptactin-APC fluorescence and the MHC-Alexa488 fluorescence over the time of analysis (FIG. 2C). To visualize the underlying dissociation kinetics, the inventors first drew 200 gates over the time of analysis and calculated the MFI of MHCAlexa488 and Streptactin-APC for each gate. This reduction of data allows for the plotting the MHCAlexa488 and the Streptactin-APC fluorescence values in one graph and therefore the direct comparison of both dissociation kinetics (FIG. 2D). At the start of the analysis, the initial staining intensity of both fluorochromes is visible and stays constant. Upon addition of D-biotin, a fast decay of the APC fluorescence is detectable, caused by the dissociation of the detached Streptactin backbone. Interestingly, also the Alexa488 fluorescence shows in the beginning a fast decay, simultaneously to the Streptactin-APC dissociation. After complete dissociation of Streptactin-APC, a second and slower decay of Alexa488 becomes detectable. These two kinetics of MHC-Alexa488 decay can be explained by different binding states of the multimerized MHC molecules. Only a part of the MHC molecules multimerized on the Streptactin backbone is likely to be bound to surface expressed TCRs. Several MHC molecules are only bound to Streptactin and dissociate therefore simultaneously with the backbone after the addition of D-biotin, showing a very fast kinetic. The following slower kinetic of Alexa488 decay results from the dissociation of monomeric TCR-bound MHC molecules from the T cell surface and is the basis for the calculation of the TCR-ligand $k_{off}$-rate. These findings indicate that the $k_{off}$-rate can only be correctly calculated after the complete dissociation of the non-cell bound components, as overlaying kinetics of TCR bound and unbound MHC-Alexa488 molecules are interfering. Therefore, the inventors decided to use the time-point of complete dissociation of Streptactin-APC as starting-point for the $k_{off}$-rate calculation of the MHC-Alexa488 dissociation.

For the final calculation of the $k_{off}$-rate, the inventors directly exported the fluorescence and time values for each analyzed cell to a spreadsheet software and generated dot plots for Streptactin-APC and MHC-Alexa488 fluorescence over the time of analysis (FIG. 2E). The inventors then selected the data points for Streptactin-APC after addition of D-biotin and for MHC-Alexa488 after complete dissociation of the Streptactin backbone. As the exponential decay is then fitted directly into the dot plot of all cells, no reduction of information is performed by calculating MFIs in a limited number of gates, which is especially important when only limited numbers of cells can be analyzed.

In summary, the transfer of the TCR-ligand $k_{off}$-rate assay to the application on the flow cytometer allows for fast analysis of T cells under temperature controlled conditions and accurate calculation of $k_{off}$-rates.

Figure 3:
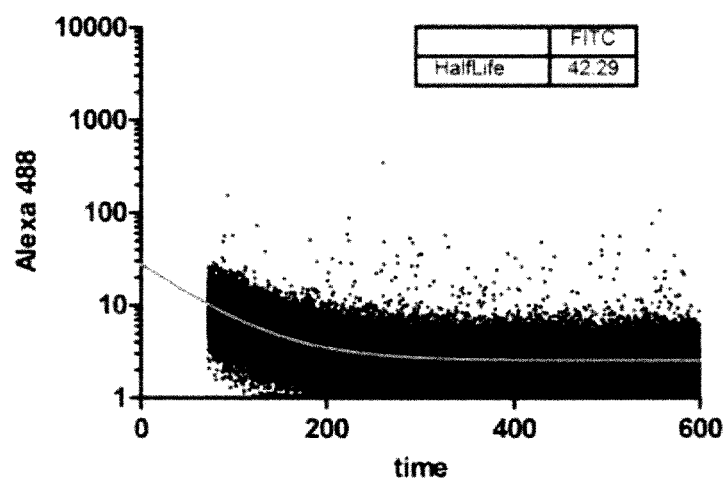
FIG. 3: Flow Cytometry Based Koff-Rate Assay with CMV-Specific T Cell Clones
Figure 3:
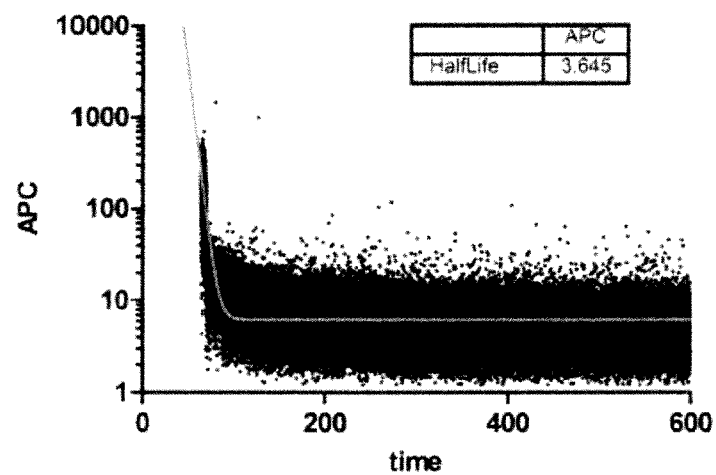
Figure 3:
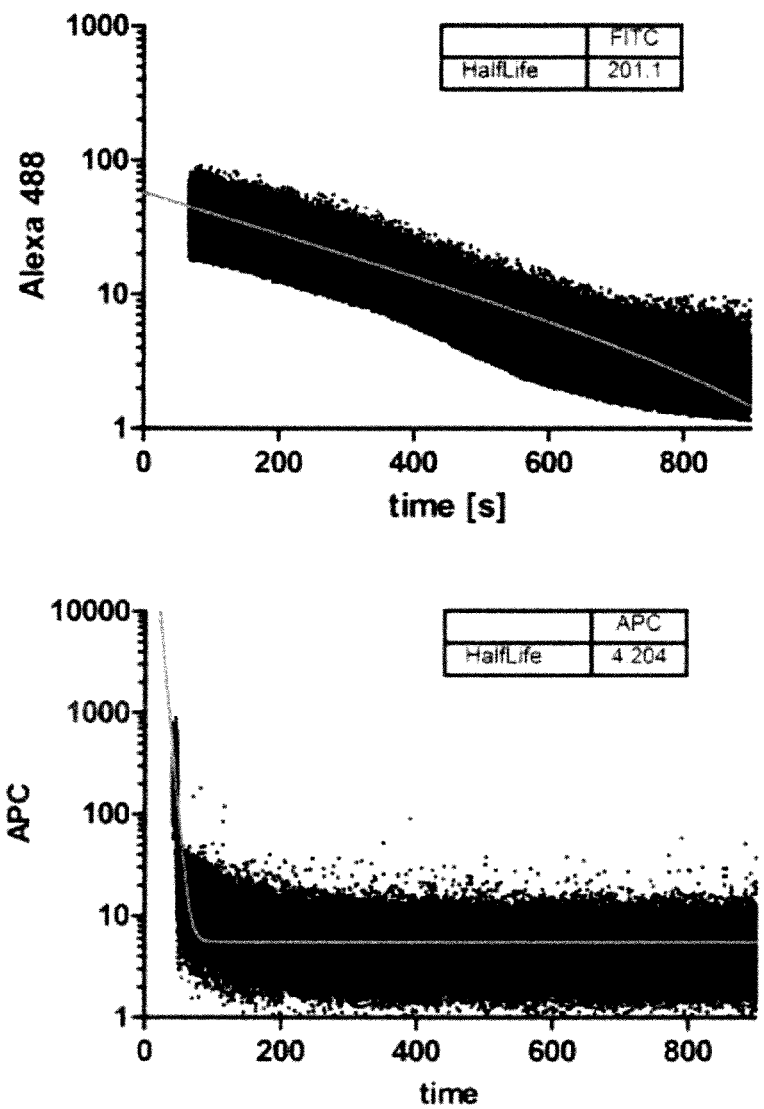
Figure 3:
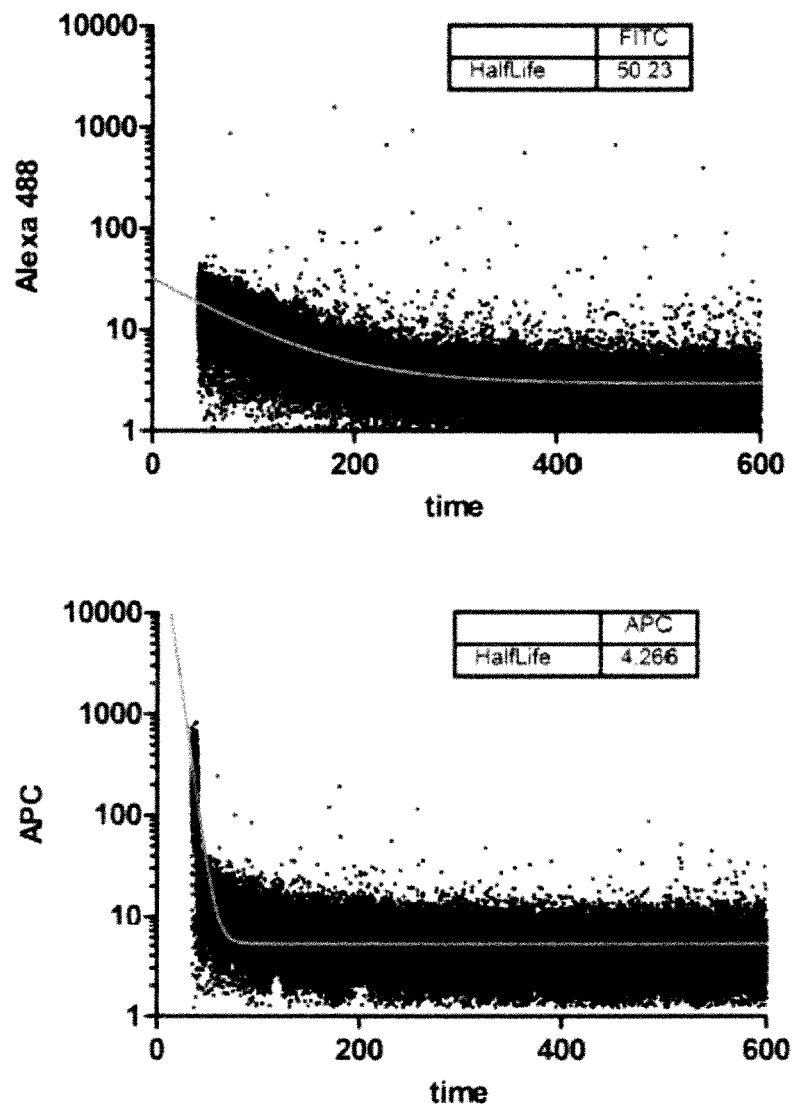
Figure 3:
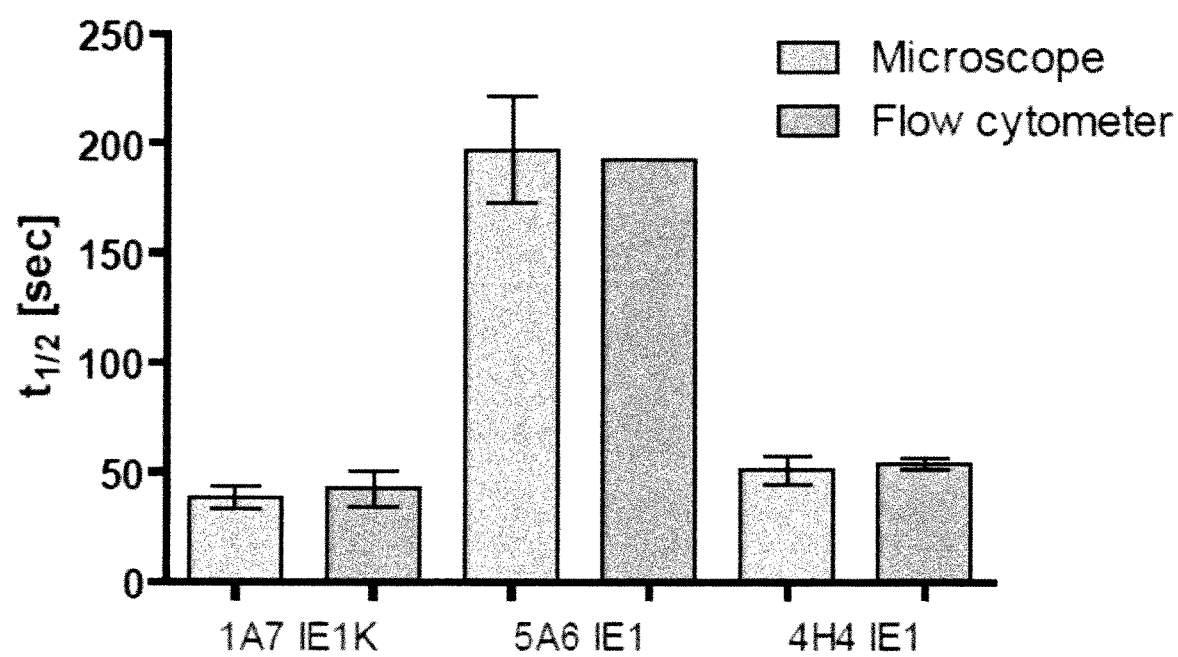

Example 2: The Flow Cytometry Based- and the Microscopy-Guided TCR-Ligand $k_{off}$-Rate Assay Provide Comparable Values With the microscopy-guided TCR-ligand $k_{off}$-rate assay, Nauert et al. 2013 demonstrated a clear correlation between the $k_{off}$-rate and the functionality of analyzed T cells. Thereby, experimental setup could be standardized the determination of highly reproducible and truly quantitative $k_{off}$-rate values could be ensured. In order to test whether results obtained from the novel flow cytometry based setting provide comparable values, the inventors analyzed the $k_{off}$-rates of CMV-specific T cell clones in parallel with both methods. Three clones of different specificities and avidities were analyzed (FIG. 3A-C) and in all cases the obtained $k_{off}$-rates were highly comparable (FIG. 3D). These data demonstrate that similar robustness, reproducibility and precision can be achieved with the novel flow cytometry based setup as compared to the previously described microscopy-guided approach.

Figure 4:
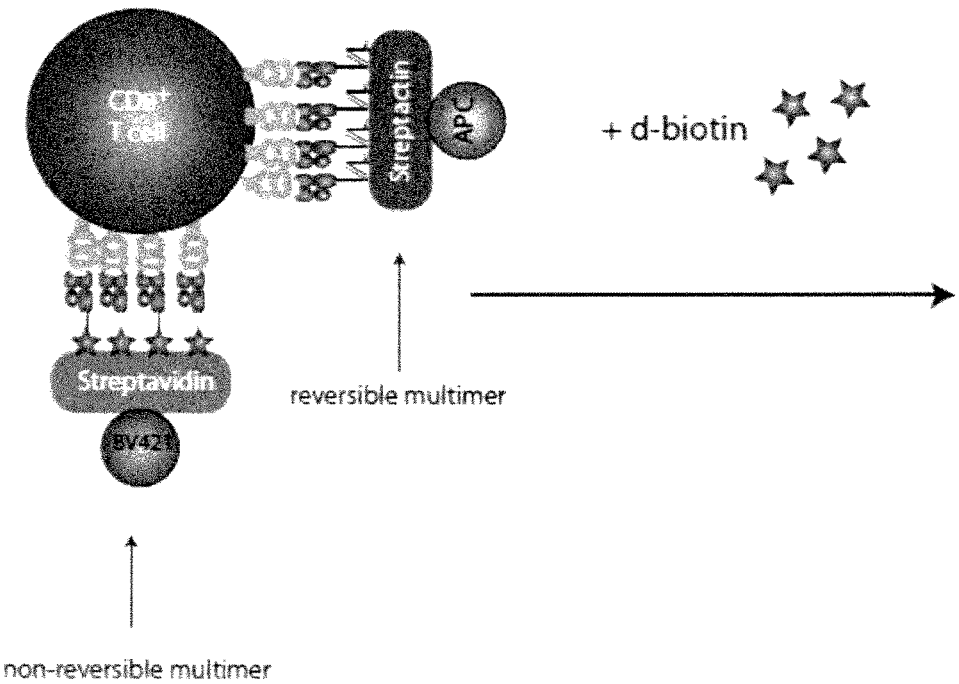
FIG. 4: Principle of Double Staining with Reversible and Non-Reversible Multimers
Figure 4:
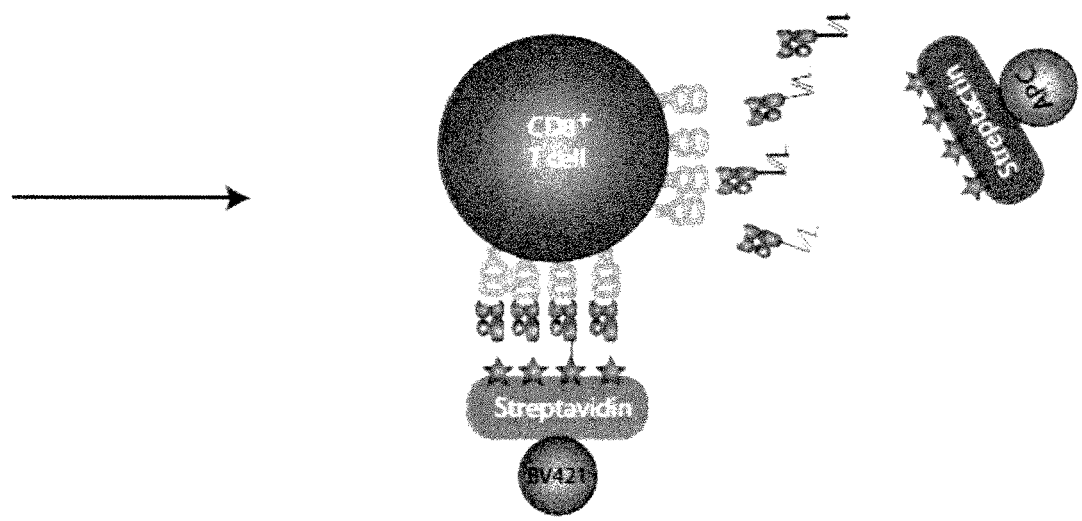
Figure 4:
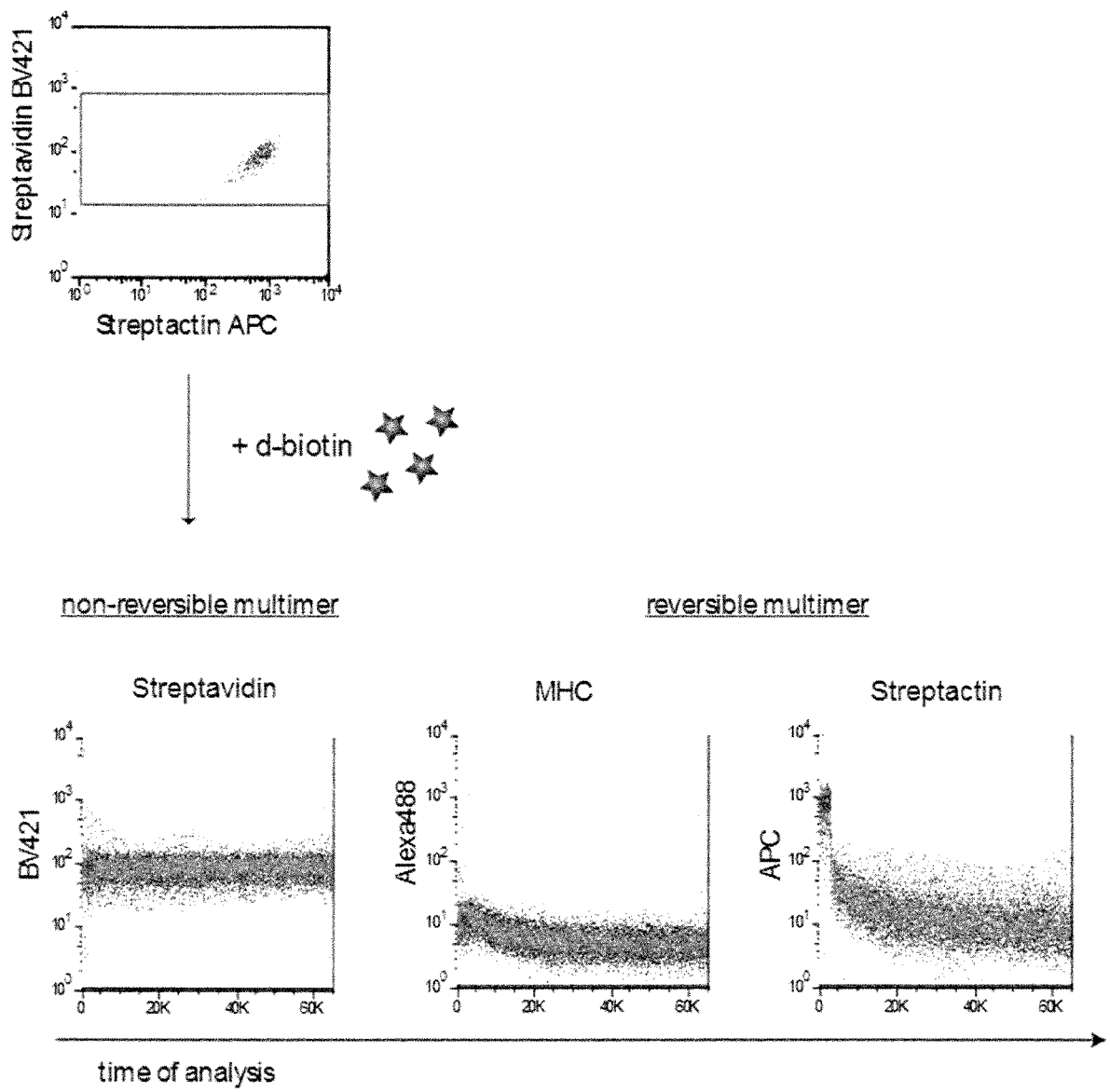

Example 3: Principle of Double Staining with Reversible and Non-Reversible MHC Multimers With the experimental setup for a flow cytometry-based $k_{off}$-rate assay described above, analysis can only be performed with highly purified antigen specific T cell populations, T cell clones or TCR-transduced T cells. In these cases, gating on living cells should be sufficient to identify the cell population of interest throughout the acquisition of ligand dissociation kinetics. However, the analysis of antigen-specific T cell populations directly ex vivo without previous sorting or cloning steps also requires stable identification of the target population during the $k_{off}$-rate assay. Therefore, the inventors tested whether this can be achieved by an additional antigen specific non-reversible staining (FIG. 4A). Conventional MHC-multimers consist of recombinant pMHCs that are biotinylated at the C-term and bind with these domains with very high affinity to Streptavidin. These bindings are not disrupted in significant amounts by the addition of D-biotin, and conventional multimers therefore provide a quasi-non-reversible staining of antigen-specific T cells. FIG. 4B shows principle of double staining of antigen-specific T cells with non-reversible multimers containing Streptavidin BV421 and reversible multimers with Alexa488 conjugated MHCs bound to a Streptactin APC backbone. It has been described previously by others that MHC multimer double staining for the same specificity is generally possible, and this approach is now frequently used to increase the sensitivity antigen-specific T cell identification (Hadrup et al., 2009, Nat Methods, 6:520-6). However, double staining with two different types of multimer reagents has not been tested so far. Therefore, the inventors stained a T cell clone specific for the CMV-derived HLA-B8 restricted epitope IE188-96 with reversible and non-reversible specific multimers. As shown in FIG. 4B (dot plot to the top left), both multimers accumulate with similar staining characteristics on the cell surface of labeled cells as indicated by a directly correlating double staining pattern. Very similar results were generated with other T cell clones with other epitope specificities and HLA-restrictions (data not shown), pointing towards the general feasibility of this approach. After addition of D-biotin, the BV421 staining remains stable over time of analysis, while the MHC-Alexa488 and the Streptactin APC staining decay (FIG. 4B, bottom panels). These data show that combined staining with conventional and reversible MHC multimers represents a suitable tool to constantly trace the cell population of interest during the TCR-ligand $k_{off}$-rate assay.

Figure 5:
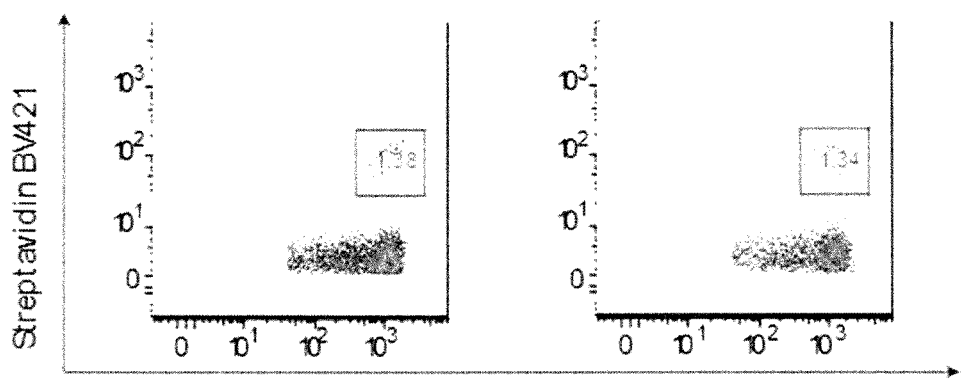
FIG. 5: Reversible Multimer Staining Intensity and $k_{off}$-Rate after Double Staining
Figure 5:
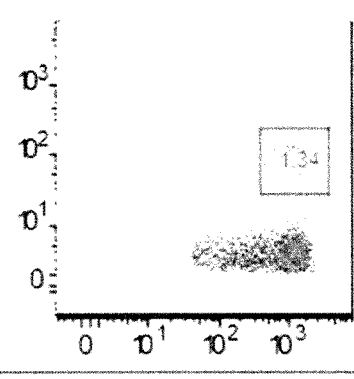
Figure 5:
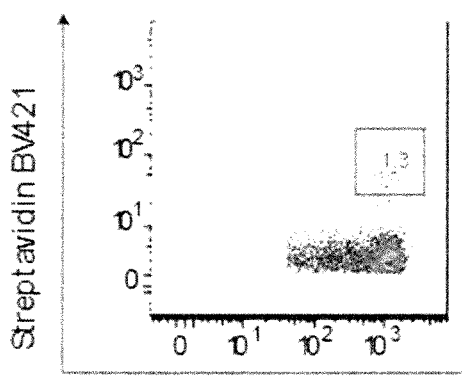
Figure 5:
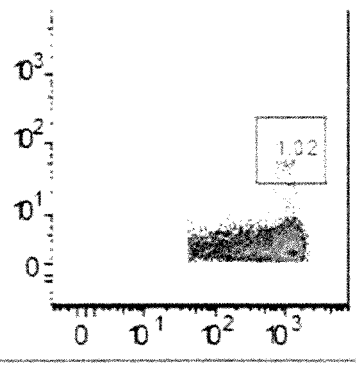
Figure 5:
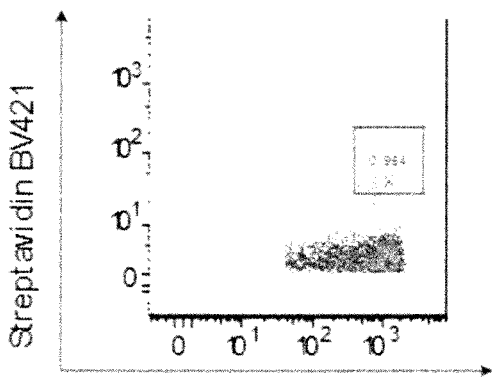
Figure 5:
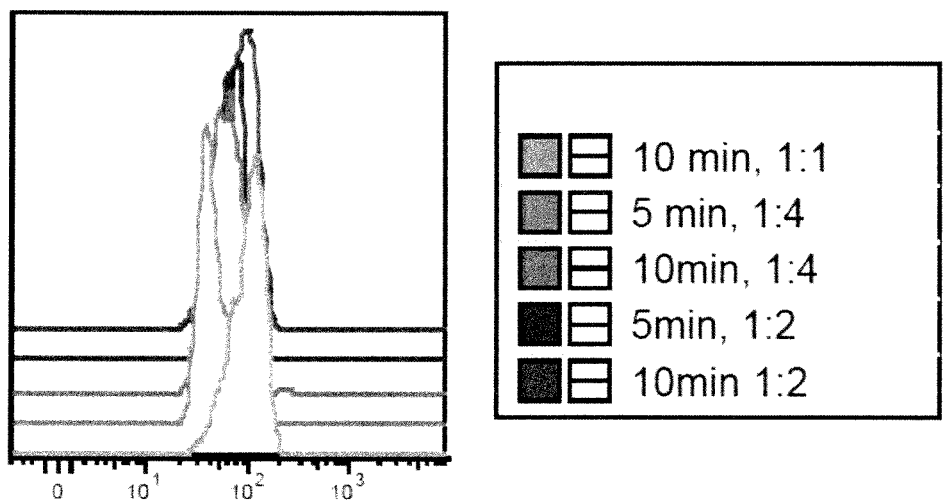
Figure 5:
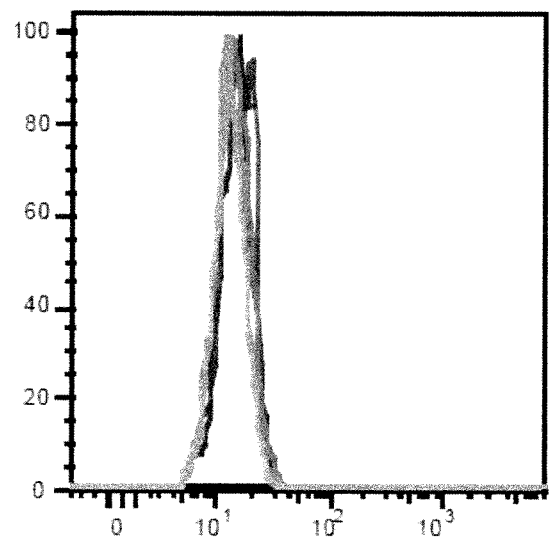
Figure 5:
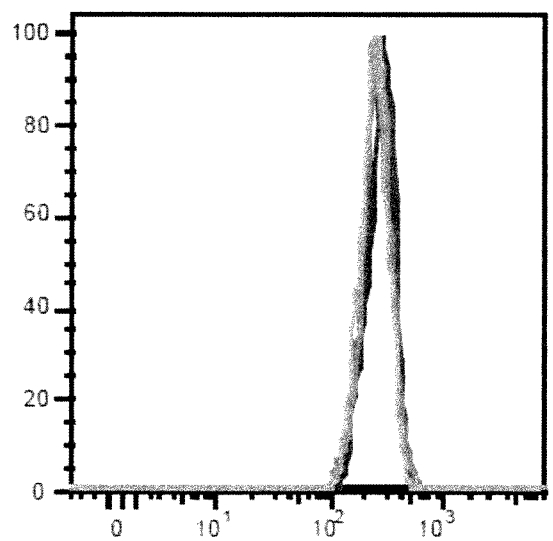
Figure 5:
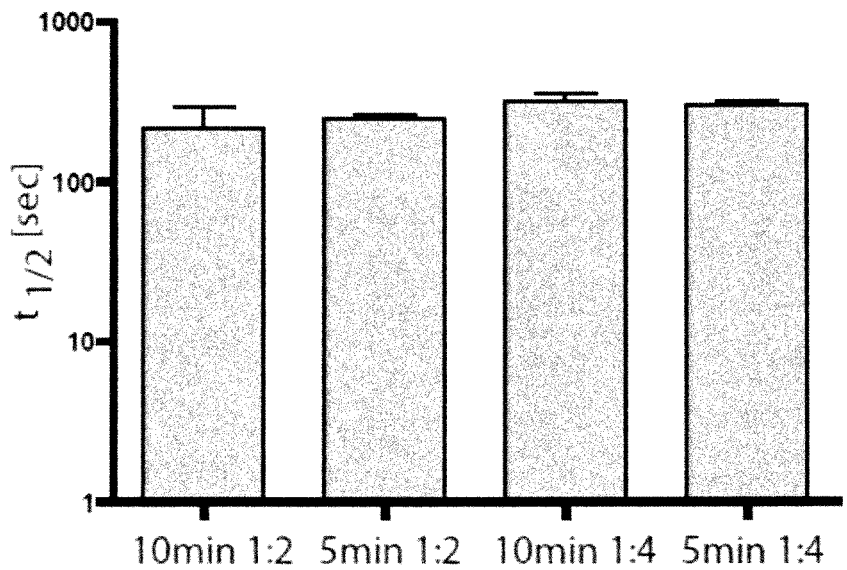
Figure 5:
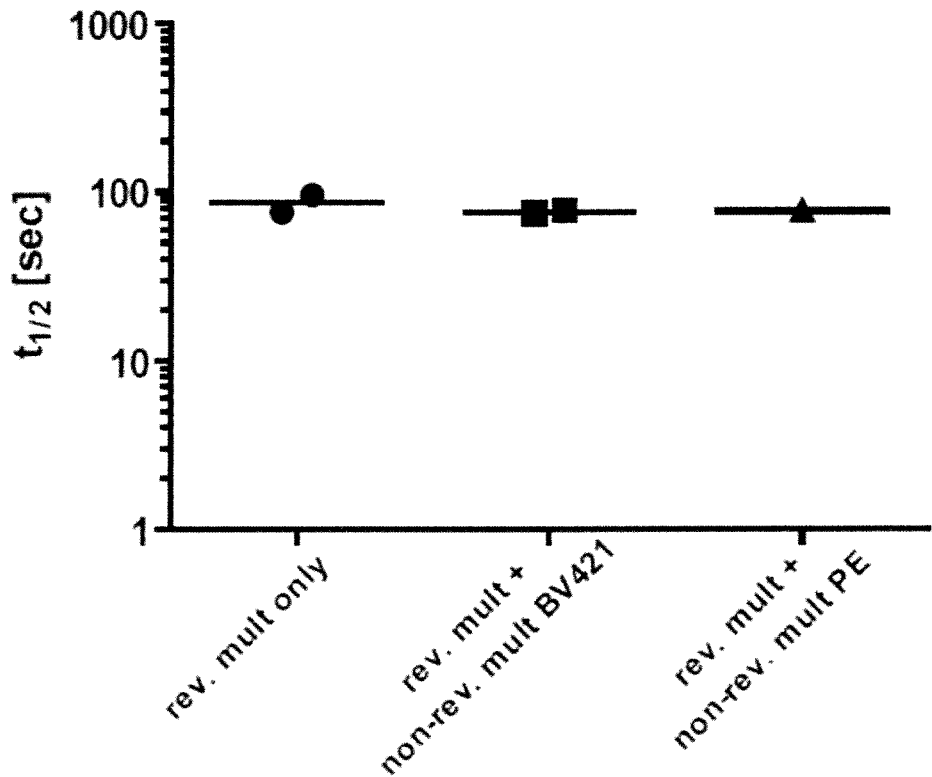
Figure 5:
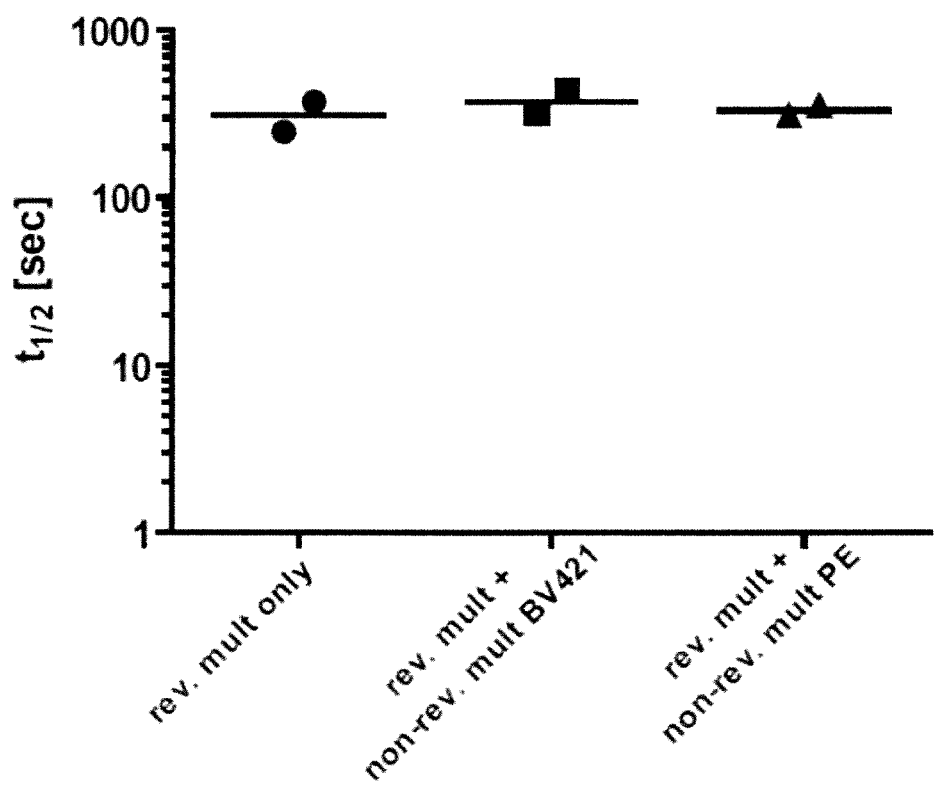

Example 4: Double Staining has No Influence on Reversible Multimer Staining Intensity and $k_{off}$-Rate To further analyze the suitability of double staining with non-reversible and reversible multimers for the $k_{off}$-rate assay in more detail, the inventors tested if additional staining with a non-reversible reagent of the same specificity interfered with reversible multimer staining and subsequent $k_{off}$-rates. Therefore, the inventors stained PBMCs from a CMV+ donor with a B7pp65 specific T cell population first with the specific reversible multimer according to the established protocol to achieve optimal MHC-Alexa488 staining intensity. After washing off unbound reagents, the inventors added in an additional staining step non-reversible multimers. The inventors titrated both concentration and incubation time over a similar initial non-reversible multimer staining procedure. As shown in FIG. 5A and FIG. 5B, increasing concentration of the non-reversible multimer only slightly affected the staining intensity of the non-reversible multimer (FIG. 5B). More importantly, across different concentration of non-reversible multimer staining, the subsequently determined $k_{off}$-rates were identical under all conditions (FIG. 5C, D). Increasing the incubation time had also no detectable effects on reversible MHC multimer staining or subsequent $k_{off}$-rate measurements (FIG. 5D). These data demonstrate that the double staining approach with reversible and non-reversible MHC multimer reagents is robust, meaning that slight changes in the staining conditions (incubation time, multimer concentration) do not affect subsequent $k_{off}$-rate results. In order to evaluate whether MHC multimer double staining could somehow affect $k_{off}$-rate kinetics, the inventors compared $k_{off}$-rate measurements of T cells stained only with the reversible multimer or stained with the non-reversible multimer in addition. These experiments were performed with well characterized high and low avidity CMV-specific T cell clones, in order to control for potential differences depending on TCR avidity. As shown in FIG. 5E and FIG. 5F, both T cell clones revealed highly comparable $k_{off}$-rates after single or double staining. This clearly demonstrates that the double staining approach did not influence resulting $k_{off}$-rate values and that this observation holds true for T cells with very different avidities.

Figure 6:
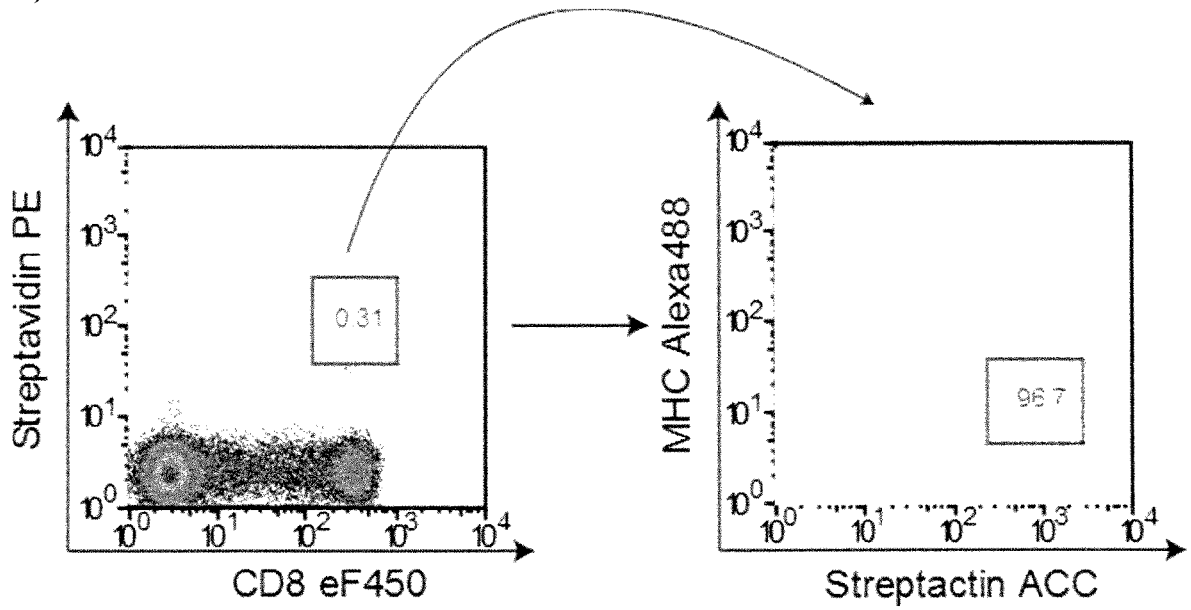
FIG. 6: Double Staining and Sort of B7 pp65 Specific T Cell Population
Figure 6:
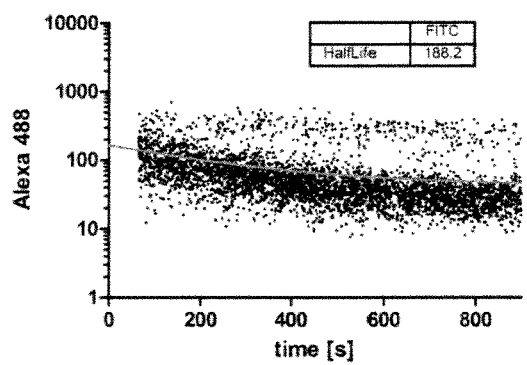
Figure 6:
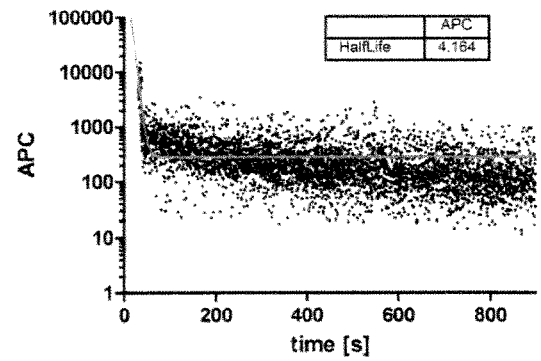
Figure 6:
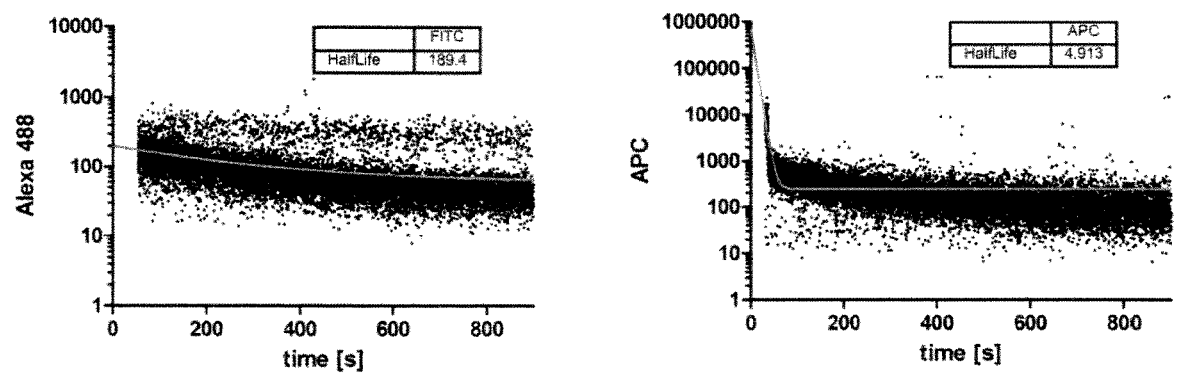
Figure 6:
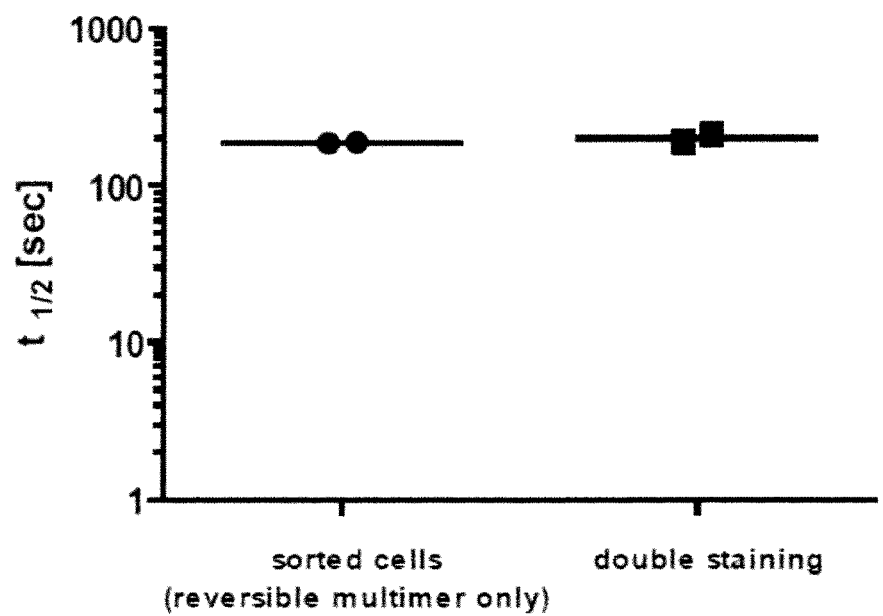

Example 5: Double Staining Enables $k_{off}$-Rate Measurement of CD8+ T Cell Populations Directly Ex Vivo As the additional staining with conventional non-reversible multimers is a suitable tool to stably stain epitope-specific T cells during the $k_{off}$-rate assay, the inventors next investigated if the direct analysis of antigen specific T cell populations from PBMCs would be possible with this setup. For this purpose, the inventors took blood from a CMV-positive donor with a readily detectable B7pp65-specific T cell population of 0.31% of all lymphocytes (FIG. 6A). The inventors purified the PBMCs by density centrifugation and stained the cells with the reversible multimer as well as a CD8 antibody, and subsequently with the non-reversible multimer. As control, a part of the cells were only stained with the reversible multimer and CD8 antibody, and the $k_{off}$-rate was analyzed after FACS sorting for Streptactin APC+ CD8+ T cells. The gating strategy for the $k_{off}$-rate measurement of the B7pp65-specific T cell population directly ex vivo is shown in FIG. 6A. After gating for singlets and living lymphocytes, a gate was set for CD8+ non-reversible multimer+ T cells. This gate was used in the analysis to display Streptactin-APC and MHC Alexa488 fluorescence over time and to calculate $k_{off}$-rates. Direct export of fluorescent values of each measured cell was chosen by analyzing this small population to prevent loss of information. This strategy demonstrated the existence of at least one high avidity T cell clone within the population that had a slow decay in MHC488 fluorescence over time (FIG. 6 B, C). The $k_{off}$-rates of the directly analyzed cells compared to previously sorted cells were similar, demonstrating the reliability of direct analysis (FIG. 6D). Altogether, these data show that double staining with non-reversible and reversible multimers enables $k_{off}$-rate measurements of epitope-specific T cell populations directly ex vivo and provides highly comparable results to previously sorted T cells.

Figure 7:
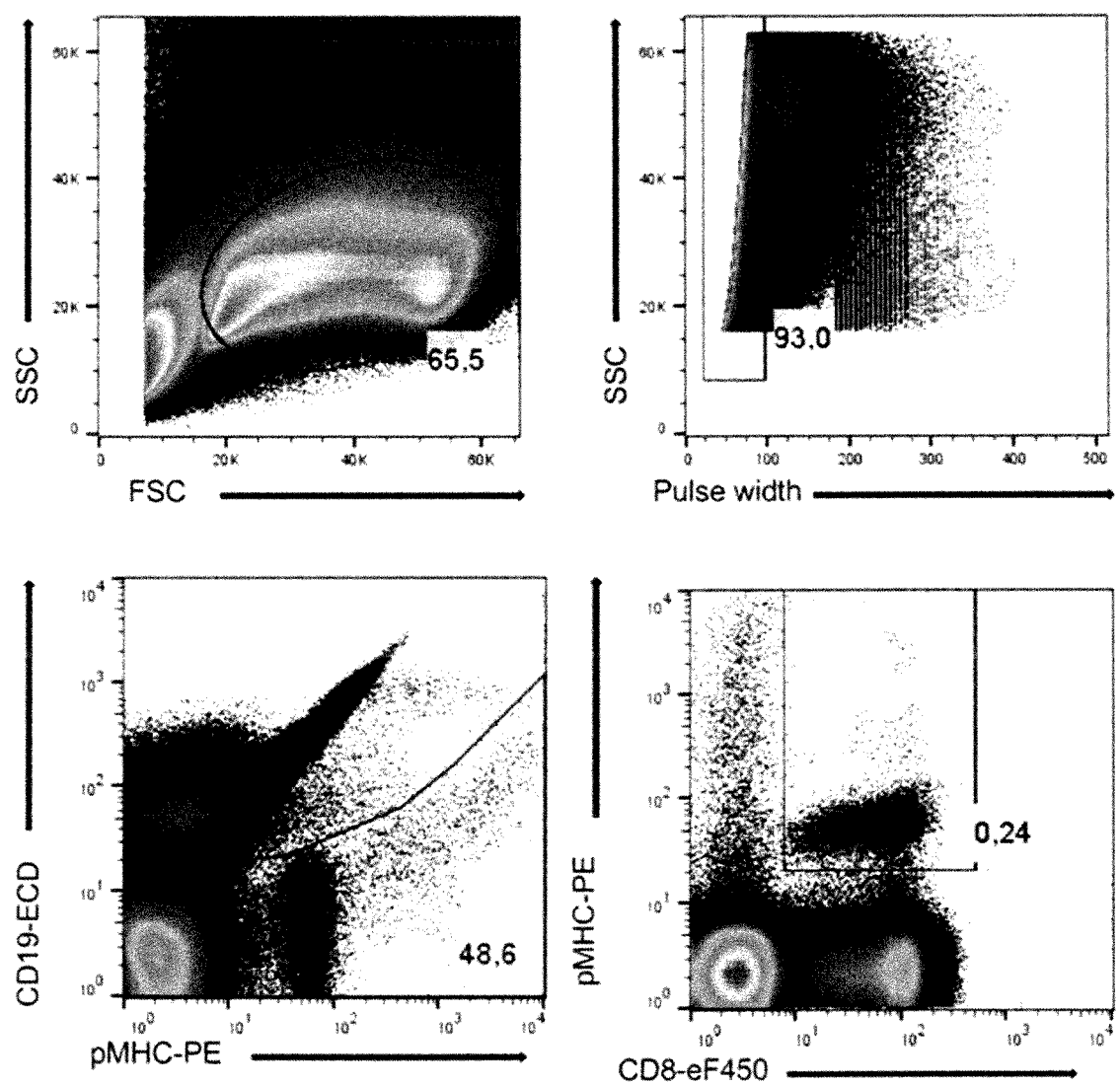
FIG. 7: Ex Vivo $k_{off}$ Rate Measurement of an Oligo Clonal HLA*07 02/CMVpp65 Specific CD8 T Cell Population.
Figure 7:
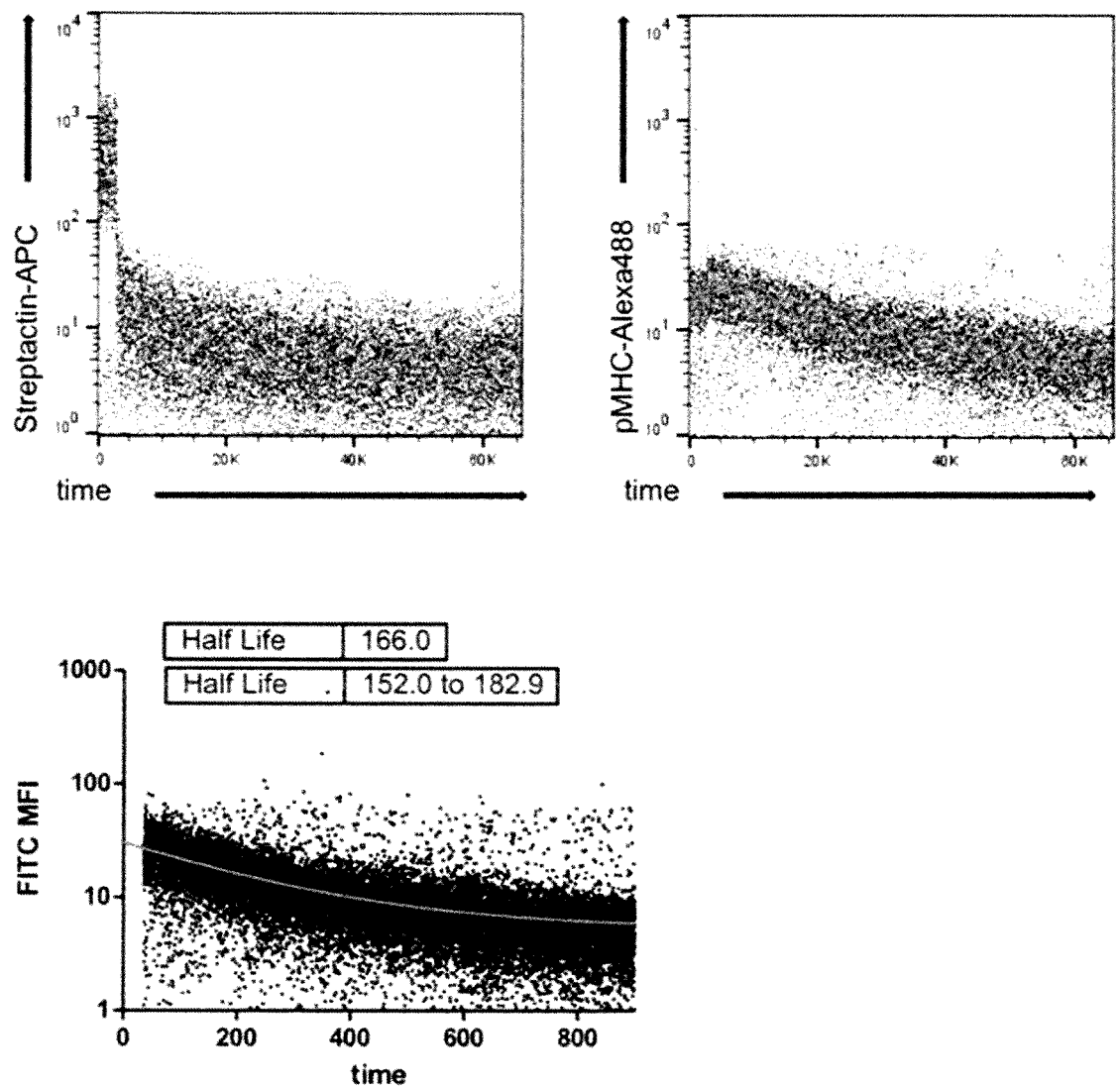

Example 6: Ex Vivo $k_{off}$ Rate Measurement of Oligoclonal Human CMV-Specific CD8+ T Cells Further ex vivo $k_{off}$ rate measurement of oligoclonal human CMV-specific CD8+ T cells from different donors were carried out as described in Example 1. Here, only a fraction of the cells comprised in the samples were CMV-specific. FIG. 7 shows ex vivo $k_{off}$ rate measurement of an oligoclonal HLA*07 02/CMVpp65 specific CD8 T cell population. PBMCs were isolated by Ficoll gradient centrifugation from fresh blood of a healthy donor. Boolean gating on single living CD19– CD8+ non-reversible pMHC-PE+ T cells was performed. Data of Streptactin APC and reversible pMHC-Alexa488 over time were exported to GraphPad PRISM to fit an exponential decay curve to determine the $k_{off}$ rate. FIG. 8 shows Ex vivo $k_{off}$ rate measurement of an oligo clonal HLA*02 01/CMVpp65 specific CD8 T cell population (donor HZ961). $k_{off}$ rate measurement was carried out on cryopreserved PBMCs isolated by Ficoll gradient centrifugation from fresh blood of a healthy donor. Boolean gating on single living CD19– CD8+ non-reversible pMHC-PE+ T cells was performed. Data of Streptactin APC and reversible pMHC-Alexa488 over time were exported to GraphPad PRISM to fit an exponential decay curve to determine the $k_{off}$ rate. FIG. 9: Ex vivo $k_{off}$ rate measurement of an oligo clonal HLA*02 01/CMVpp65 specific CD8 T cell population (donor HZ510). $k_{off}$ rate measurement was carried out on cryopreserved PBMCs isolated by Ficoll gradient centrifugation from fresh blood of a healthy donor. Boolean gating on single living CD19-CD8+ non-reversible pMHC-PE+ T cells was performed. Data of Streptactin APC and reversible pMHC-Alexa488 over time were exported to GraphPad PRISM to fit an exponential decay curve to determine the $k_{off}$ rate. These experiments demonstrate that $k_{off}$ rate determination of target specific CD8+ T cells can be carried out directly on blood or PBMC samples and that reliable results are achieved with cells from different donors.

Example 7: Functional Characterization of Isolated TCRs Using $k_{off}$ Rate Measurement on CD8+ J76 Tumor Cells Two HLA*02 01/CMVpp65 specific TCRs were isolated using single clone PCR. To analyze their structural avidity, TCRs were transduced into CD8+ J76 tumor cells lacking an endogenous TCR. $K_{off}$ rate measurement was carried out as described in Example 1. Boolean gating on single living CD8+ non-reversible pMHC-PE+ T cells was performed. Data of Streptactin APC and reversible pMHC-Alexa488 over time were exported to GraphPad PRISM to fit an exponential decay curve to determine the $k_{off}$ rate (FIG. 10). Although only a small portion of J76 tumor cells recombinantly expressed the respective TCR, the $k_{off}$ values of the two TCRs were reliably determined. This experiment shows again that the $k_{off}$ rate of a receptor that is only present in a small portion of cells within a complex population can be determined using the methods described herein Example 8: $k_{off}$ Rate Measurement in a Murine Model System for High and Low Avidity TCR pMHC Interaction FIG. 11 shows $k_{off}$ rate determination of murine T cells which was carried out as described in Example 1. For this purpose, reversible and non-reversible murine MHC multimers were generated according to the method described in Example 1. The H2-KB multimers were generated using the following epitopes: SIIQFEKL:H2kb (SEQ ID NO:14), SIYNFEKL:H2kb (SEQ ID NO: 15), and SIINFEKL:H2kb (SEQ ID NO: 15). These results show that the methods described herein can be carried out on cells of different species.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method of determining the dissociation rate constant ($k_{off}$) of binding between a receptor R expressed on a surface of a target cell and a first receptor binding site B1, comprising:
    providing said target cell comprising a first detectable label and a second detectable label attached to the target cell by contacting the target cell with
        (i) a first receptor binding reagent comprising said first detectable label, and at least one said first receptor binding site B1, wherein the first receptor binding site B1 specifically binds to said receptor R, the first receptor binding reagent further comprising at least one first binding partner C1, wherein the first binding partner C1 is capable of being reversibly bound to a first binding site Z1 of a first multimerization reagent,
        (ii) said first multimerization reagent comprising at least two said first binding sites Z1,
    wherein the first receptor binding reagent and the first multimerization reagent form a first multivalent binding complex that reversibly attaches to receptor R on said target cell, the first multivalent binding complex comprising at least two of said first receptor binding reagents bound to one said first multimerization reagent, and
        (iii) said second detectable label that stably attaches to said receptor R on said target cell, wherein the first detectable label and the second detectable label are different from each other, and wherein said first detectable label and said second detectable label are simultaneously attached to the target cell through different receptors R;
    detaching the first detectable label from the target cell by competitively disrupting binding between the first receptor binding reagent and the first multimerization reagent, wherein said second detectable label remains stably attached to said receptor R on said target cell; and
    identifying said target cell by detecting the second detectable label stably attached thereto and determining the dissociation rate constant as a function of said detaching of the first detectable label from the target cell determined from loss of the first detectable label from the identified target cells.

2. The method of claim 1, wherein the cell has further been contacted with
    a second receptor binding reagent comprising at least one second receptor binding site B2, wherein the second receptor binding site B2 specifically binds to said receptor R, the second receptor binding reagent further comprising at least one second binding partner C2, wherein the second binding partner C2 is capable of stably attaching to a second binding site Z2 of a second multimerization reagent, and
    said second multimerization reagent comprising at least two said second binding sites Z2,
    wherein the second receptor binding reagent and the second multimerization reagent form a second multivalent binding complex that binds to said target cell, the second multivalent binding complex comprising at least two of second receptor binding reagents bound to one said second multimerization reagent.

3. The method of claim 1, wherein
    said second detectable label is a component of a multimeric receptor binding reagent M2 comprising at least two second receptor binding sites B2, wherein the second receptor binding site B2 specifically binds to said receptor R,
    wherein the multimeric receptor binding reagent M2 stably attaches to said target cell via said receptor R, thereby stably attaching said second detectable label to said receptor R on said target cell.

4. The method of claim 1, wherein
    said second detectable label is a component of an irreversible receptor binding reagent I2 that specifically binds to said receptor R, wherein the irreversible receptor binding reagent I2 stably attaches to said receptor R, thereby stably attaching said second detectable label to said receptor R on said target cell.

5. The method of claim 1, wherein said receptor R is a T cell receptor (TCR).

6. The method of claim 1, wherein said first receptor binding site B1 is a MHC protein.

7. The method of claim 1, wherein
a. said first binding partner C1 comprises a streptavidin or avidin binding peptide and said first multimerization reagent comprises streptavidin, or avidin, or a streptavidin analog, or avidin analog that reversibly binds to said streptavidin or avidin binding peptide; or
b. said first binding partner C1 comprises a biotin analog that reversibly binds to streptavidin or avidin and said first multimerization reagent comprises streptavidin, or avidin, or a streptavidin analog, or an avidin analog that reversibly binds to said biotin analog.

8. The method of one of claims 1-3, comprising
contacting said target cell comprising said receptor R with said first receptor binding reagent and said first multimerization reagent and contacting said target cell with the second receptor binding reagent and the second multimerization reagent,
or
contacting said target cell with the multimeric receptor binding reagent M2;
or
contacting said target cell with the irreversible receptor binding reagent I2.

9. The method of claim 8, further comprising
(c) disrupting the binding between the first receptor binding reagent and the first multimerization reagent.

10. The method of claim 9, wherein the binding between the first receptor binding reagent and the first multimerization reagent is disrupted with a competition reagent CR, wherein the competition reagent CR is capable of competing with first binding partner C1 for the binding to the first binding site Z1 on the first multimerization reagent.

11. The method of claim 8, further comprising detecting the first detectable label attached to the target cell and detecting the second detectable label attached to the target cell.

12. A cell comprising:
receptor R expressed on a surface thereof, wherein the cell has bound to at least two receptor R molecules
(i) a first receptor binding reagent comprising a first detectable label, and at least one first receptor binding site B1, wherein the first receptor binding site B1 specifically binds to said receptor R, the first receptor binding reagent further comprising at least one first binding partner C1, wherein the first binding partner C1 is capable of being reversibly bound to a first binding site Z1 of a first multimerization reagent,
(ii) a first multimerization reagent comprising at least two first binding sites Z1,
wherein the first receptor binding reagent and the first multimerization reagent form a first multivalent binding complex that is reversibly attached to said at least two receptors R on said cell, the first multivalent binding complex comprising at least two of said first receptor binding reagents bound to one said first multimerization reagent, and
wherein the cell has bound to at least one receptor R molecule a second detectable label that is stably attached to said at least one receptor R molecule on said cell,
wherein the first detectable label and the second detectable label are different from each other, and wherein said first detectable label and said second detectable label are simultaneously attached to the target cell through receptors R.

13. The cell of claim 12, wherein the cell has further bound to at least two receptor R molecules a second receptor binding reagent comprising at least one second receptor binding site B2, wherein the second receptor binding site B2 specifically binds to said receptor R, the second receptor binding reagent further comprising at least one second binding partner C2, wherein the second binding partner C2 is capable of stably attaching to a second binding site Z2 of a second multimerization reagent, and said second multimerization reagent comprising at least two said second binding sites Z2, wherein the second receptor binding reagent and the second multimerization reagent form a second multivalent binding complex that binds to said target cell, the second multivalent binding complex comprising at least two of second receptor binding reagents bound to one said second multimerization reagent.

14. The cell of claim 12, wherein the cell has further bound to at least two receptor R molecules said second detectable label is a component of a multimeric receptor binding reagent M2 comprising at least two second receptor binding sites B2, wherein the second receptor binding site B2 specifically binds to said receptor R, wherein the multimeric receptor binding reagent M2 stably attaches to said target cell via said receptor R, thereby stably attaching said second detectable label to said receptor R on said target cell.

15. The cell of claim 12, wherein said second detectable label is a component of an irreversible receptor binding reagent I2 that specifically binds to said receptor R, wherein the irreversible receptor binding reagent I2 stably attaches to said receptor R, thereby stably attaching said second detectable label to said receptor R on said target cell.

16. The cell of claim 12, wherein said receptor R is a T cell receptor.

17. An apparatus comprising
a first container containing a target cell comprising a receptor R expressed on a surface thereof, and
(i) a first receptor binding reagent comprising a first detectable label, and at least one said first receptor binding site B1, wherein the first receptor binding site B1 specifically binds to said receptor R, the first receptor binding reagent further comprising at least one first binding partner C1, wherein the first binding partner C1 is capable of being reversibly bound to a first binding site Z1 of a first multimerization reagent,
(ii) said first multimerization reagent comprising at least two said first binding sites Z1,
wherein the first receptor binding reagent and the first multimerization reagent form a first multivalent binding complex that reversibly attaches to receptor R on said target cell, the first multivalent binding complex comprising at least two of said first receptor binding reagents bound to one said first multimerization reagent; and
wherein a second detectable label stably attaches to said receptor R on said target cell, wherein the first detectable label and the second detectable label are different from each other, and wherein said first detectable label and said second detectable label are simultaneously attached to the target cell through receptors R; and a second container containing a fluid comprising
   a. a competition reagent CR, wherein the competition reagent CR is capable of competing with first binding partner C1 for the binding to the first binding site Z1 on the first multimerization reagent; or
   b. a metal chelating reagent,
wherein the first container and a second container are operably connected such that a fluid transferred from the second container to the first container such that the competition reagent CR or metal chelating reagent competitively disrupts binding between the first receptor binding reagent and the first multimerization reagent, wherein said second detectable label remains stably attached to said receptor R on said target cell.

18. The apparatus of claim 17, wherein the first container further contains
   a second receptor binding reagent comprising at least one second receptor binding site B2, wherein the second receptor binding site B2 specifically binds to said receptor R, the second receptor binding reagent further comprising at least one second binding partner C2, wherein the second binding partner C2 is capable of stably attaching to a second binding site Z2 of a second multimerization reagent, and
said second multimerization reagent comprising at least two said second binding sites Z2,
wherein the second receptor binding reagent and the second multimerization reagent form a second multivalent binding complex that binds to said target cell, the second multivalent binding complex comprising at least two of second receptor binding reagents bound to one said second multimerization reagent.

19. A method of isolating a high-avidity T cell comprising
   a) determining the dissociation rate constant ($k_{off}$) of a T cell in a sample obtained from a subject using the method according to claim 1 to identify said high-avidity T cell, wherein said receptor R is a T cell receptor (TCR), and
   b) isolating said T cell from the sample.

\* \* \* \* \*

UNITED STATES PATENT AND TRADEMARK OFFICE
CERTIFICATE OF CORRECTION

| | |
|---|---|
| PATENT NO. | : 11,320,431 B2 |
| APPLICATION NO. | : 16/314126 |
| DATED | : May 3, 2022 |
| INVENTOR(S) | : Magdalena Nauerth, Dirk Busch and Lothar Germeroth |

It is certified that error appears in the above-identified patent and that said Letters Patent is hereby corrected as shown below:

In the Claims

<u>Column 51</u>
Line 12, delete:
"8. The method of one of claims 1-3, comprising"
And replace it with:
-- 8. The method of any one of claims 1-3, comprising --

Signed and Sealed this
Twenty-eighth Day of March, 2023

Katherine Kelly Vidal
*Director of the United States Patent and Trademark Office*

SEQUENCE LISTING

```
<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: streptavidin-binding peptide

<400> SEQUENCE: 1

Trp Ser His Pro Gln Phe Glu Lys
1               5

<210> SEQ ID NO 2
<211> LENGTH: 4
<212> TYPE: PRT
<213> ORGANISM: Artificial Sequence
<220> FEATURE:
<223> OTHER INFORMATION: streptaviding analog (aa44-47)

<400> SEQUENCE: 2

Val Thr Ala Arg
1

<210> SEQ ID NO 3
<211> LENGTH: 4
<212> TYPE: PRT
<213> ORGANISM: Artificial Sequence
<220> FEATURE:
<223> OTHER INFORMATION: streptaviding analog (aa44-47)
```

```
<400> SEQUENCE: 3

Ile Gly Ala Arg
1

<210> SEQ ID NO 4
<211> LENGTH: 8
<212> TYPE: PRT
<213> ORGANISM: Artificial Sequence
<220> FEATURE:
<223> OTHER INFORMATION: FLAG-tag

<400> SEQUENCE: 4

Asp Tyr Lys Asp Asp Asp Asp Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Myc-tag

<400> SEQUENCE: 5

Glu Gln Lys Leu Ile Ser Glu Glu Asp Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: HA-tag

<400> SEQUENCE: 6

Tyr Pro Tyr Asp Val Pro Asp Tyr Ala
1               5

<210> SEQ ID NO 7
<211> LENGTH: 11
<212> TYPE: PRT
<213> ORGANISM: Artificial Sequence
<220> FEATURE:
<223> OTHER INFORMATION: VSV-G-tag

<400> SEQUENCE: 7

Tyr Thr Asp Ile Glu Met Asn Arg Leu Gly Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: HSV-tag

<400> SEQUENCE: 8

Gln Pro Glu Leu Ala Pro Glu Asp Pro Glu Asp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: V5-tag

<400> SEQUENCE: 9
```

```
Gly Lys Pro Ile Pro Asn Pro Leu Leu Gly Leu Asp Ser Thr
1               5                   10

<210> SEQ ID NO 10
<211> LENGTH: 8
<212> TYPE: PRT
<213> ORGANISM: Artificial Sequence
<220> FEATURE:
<223> OTHER INFORMATION: peptide in complex with H2Kb

<400> SEQUENCE: 10

Ser Ile Tyr Arg Tyr Tyr Gly Leu
1               5

<210> SEQ ID NO 11
<211> LENGTH: 28
<212> TYPE: PRT
<213> ORGANISM: Artificial Sequence
<220> FEATURE:
<223> OTHER INFORMATION: di-tag3

<400> SEQUENCE: 11

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25

<210> SEQ ID NO 12
<211> LENGTH: 24
<212> TYPE: PRT
<213> ORGANISM: Artificial Sequence
<220> FEATURE:
<223> OTHER INFORMATION: di-tag2

<400> SEQUENCE: 12

Trp Ser His Pro Gln Phe Glu Lys Gly Gly Gly Ser Gly Gly Gly Ser
1               5                   10                  15

Trp Ser His Pro Gln Phe Glu Lys
            20

<210> SEQ ID NO 13
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 13

Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25

<210> SEQ ID NO 14
<211> LENGTH: 8
<212> TYPE: PRT
<213> ORGANISM: Artificial Sequence
<220> FEATURE:
<223> OTHER INFORMATION: peptide in complex with H2kb

<400> SEQUENCE: 14

Ser Ile Ile Gln Phe Glu Lys Leu
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: peptide in complex with H2kb

<400> SEQUENCE: 15

Ser Ile Tyr Asn Phe Glu Lys Leu
1               5

<210> SEQ ID NO 16
<211> LENGTH: 8
<212> TYPE: PRT
<213> ORGANISM: Artificial Sequence
<220> FEATURE:
<223> OTHER INFORMATION: peptide in complex with H2kb

<400> SEQUENCE: 16

Ser Ile Ile Asn Phe Glu Lys Leu
1               5
```